(12) United States Patent
Schepis et al.

(10) Patent No.: US 11,446,498 B2
(45) Date of Patent: Sep. 20, 2022

(54) DEVICE AND METHOD TO SELECTIVELY AND REVERSIBLY MODULATE A NERVOUS SYSTEM STRUCTURE TO INHIBIT PAIN

(71) Applicant: Avent, Inc., Alpharetta, GA (US)

(72) Inventors: Eric A. Schepis, Alpharetta, GA (US); David M. Page, Alpharetta, GA (US); Phillip A. Schorr, Alpharetta, GA (US); Shyamy R. Sastry, Alpharetta, GA (US); Leah Roldan, Alpharetta, GA (US); Natalia Alexeeva, Alpharetta, GA (US); Ryan Caldwell, Alpharetta, GA (US); Amol Soin, Dayton, OH (US)

(73) Assignee: Avent, Inc., Alpharetta, GA (US)

( * ) Notice: Subject to any disclaimer, the term of this patent is extended or adjusted under 35 U.S.C. 154(b) by 74 days.

(21) Appl. No.: 16/676,202

(22) Filed: Nov. 6, 2019

(65) Prior Publication Data

US 2020/0179690 A1 Jun. 11, 2020

Related U.S. Application Data

(60) Provisional application No. 62/776,908, filed on Dec. 7, 2018.

(51) Int. Cl.
*A61N 1/36* (2006.01)
*A61N 1/05* (2006.01)
*A61N 1/04* (2006.01)

(52) U.S. Cl.
CPC ....... *A61N 1/36071* (2013.01); *A61N 1/0456* (2013.01); *A61N 1/0551* (2013.01); *A61N 1/3614* (2017.08); *A61N 1/36021* (2013.01); *A61N 1/36062* (2017.08); *A61N 1/36135* (2013.01); *A61N 1/36139* (2013.01);
(Continued)

(58) Field of Classification Search
CPC ............ A61N 1/36071; A61N 1/36062; A61N 1/3614; A61N 1/0456; A61N 1/0551; A61N 1/36021; A61N 1/36135; A61N 1/36139; A61N 1/36153; A61N 1/36171; A61N 1/36175; A61N 1/36192; A61N 1/36132
See application file for complete search history.

(56) References Cited

U.S. PATENT DOCUMENTS 6,246,912 B1 * 6/2001 Sluijter ............... A61N 1/36021
607/100
6,293,943 B1 * 9/2001 Panescu ................. A61N 1/403
606/41

(Continued)

OTHER PUBLICATIONS

Search Report under Section 17(5) dated Aug. 26, 2020, from related GB Application No. 1916156.1, 4 pages.

*Primary Examiner* — Lindsey G Wehrheim
(74) *Attorney, Agent, or Firm* — Meunier Carlin & Curfman LLC

(57) ABSTRACT

The present disclosure is directed to a system and method for selectively and reversibly modulating targeted neural and non-neural tissue of a nervous system for the treatment of pain. An electrical stimulation is delivered to the treatment site that selectively and reversibly modulates the targeted neural- and non-neural tissue of the nervous structure, inhibiting pain while preserving other sensory and motor function, and proprioception.

24 Claims, 19 Drawing Sheets
(13 of 19 Drawing Sheet(s) Filed in Color)

(52) U.S. Cl.
CPC ..... *A61N 1/36153* (2013.01); *A61N 1/36171* (2013.01); *A61N 1/36175* (2013.01); *A61N 1/36192* (2013.01); *A61N 1/36132* (2013.01)

(56) References Cited

U.S. PATENT DOCUMENTS

| | | | |
|---|---|---|---|
| RE41,045 E | 12/2009 | Sluijter et al. | |
| 8,060,208 B2 | 11/2011 | Kilgore et al. | |
| 8,352,026 B2 | 1/2013 | Diubaldi | |
| 8,700,180 B2 | 4/2014 | Bradley | |
| 8,843,209 B2 | 4/2014 | Wacnik et al. | |
| 8,731,676 B2 | 5/2014 | Fang et al. | |
| 8,983,612 B2 | 3/2015 | Fang et al. | |
| 9,037,261 B2 | 5/2015 | Bradley | |
| 9,174,053 B2 | 11/2015 | Zhu | |
| 9,526,889 B2 | 12/2016 | Chang et al. | |
| 9,700,725 B2 | 7/2017 | Zhu | |
| 9,713,711 B2 | 7/2017 | Hershey et al. | |
| 10,035,012 B2* | 7/2018 | North | A61N 1/0553 |
| 10,086,201 B2 | 10/2018 | Chang et al. | |
| 10,105,541 B2 | 10/2018 | Kishawi et al. | |
| 10,118,040 B2 | 11/2018 | Zhu | |
| 10,384,060 B2 | 8/2019 | Hershey et al. | |
| 10,413,717 B2 | 9/2019 | Inui et al. | |
| 10,549,099 B2 | 2/2020 | Kluger et al. | |
| 10,828,491 B2 | 11/2020 | Schepis et al. | |
| 2005/0222642 A1* | 10/2005 | Przybyszewski | A61N 1/36142 607/48 |
| 2012/0203304 A1 | 8/2012 | Alataris et al. | |
| 2012/0310140 A1 | 12/2012 | Kramer et al. | |
| 2013/0085548 A1 | 4/2013 | Mironer | |
| 2013/0245711 A1 | 9/2013 | Simon et al. | |
| 2013/0261695 A1* | 10/2013 | Thacker | A61N 1/36171 607/46 |
| 2015/0297892 A1* | 10/2015 | Tol | A61N 1/37217 600/378 |
| 2016/0287112 A1 | 10/2016 | McFarlin et al. | |
| 2017/0080232 A1 | 3/2017 | Torgerson | |
| 2017/0095666 A1 | 4/2017 | Imran | |
| 2017/0224989 A1 | 8/2017 | Schepis et al. | |
| 2017/0348049 A1* | 12/2017 | Vrba | A61B 18/1492 |
| 2018/0154139 A1* | 6/2018 | Howard | A61N 1/0551 |
| 2018/0200506 A1 | 7/2018 | Fang et al. | |
| 2019/0282809 A1 | 9/2019 | Schepis | |
| 2019/0282810 A1 | 9/2019 | Schepis | |
| 2021/0052899 A1 | 2/2021 | Schepis et al. | |

* cited by examiner

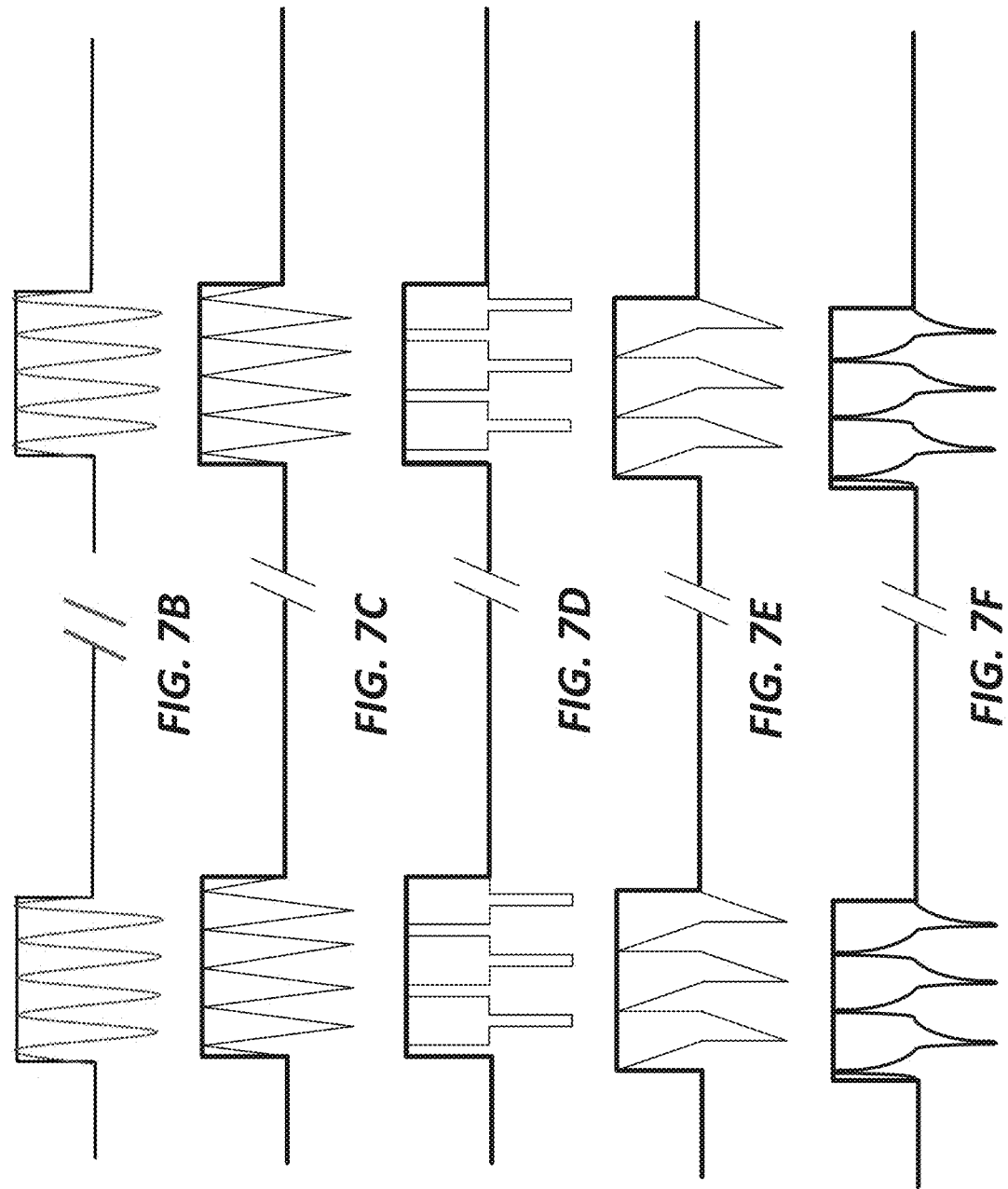

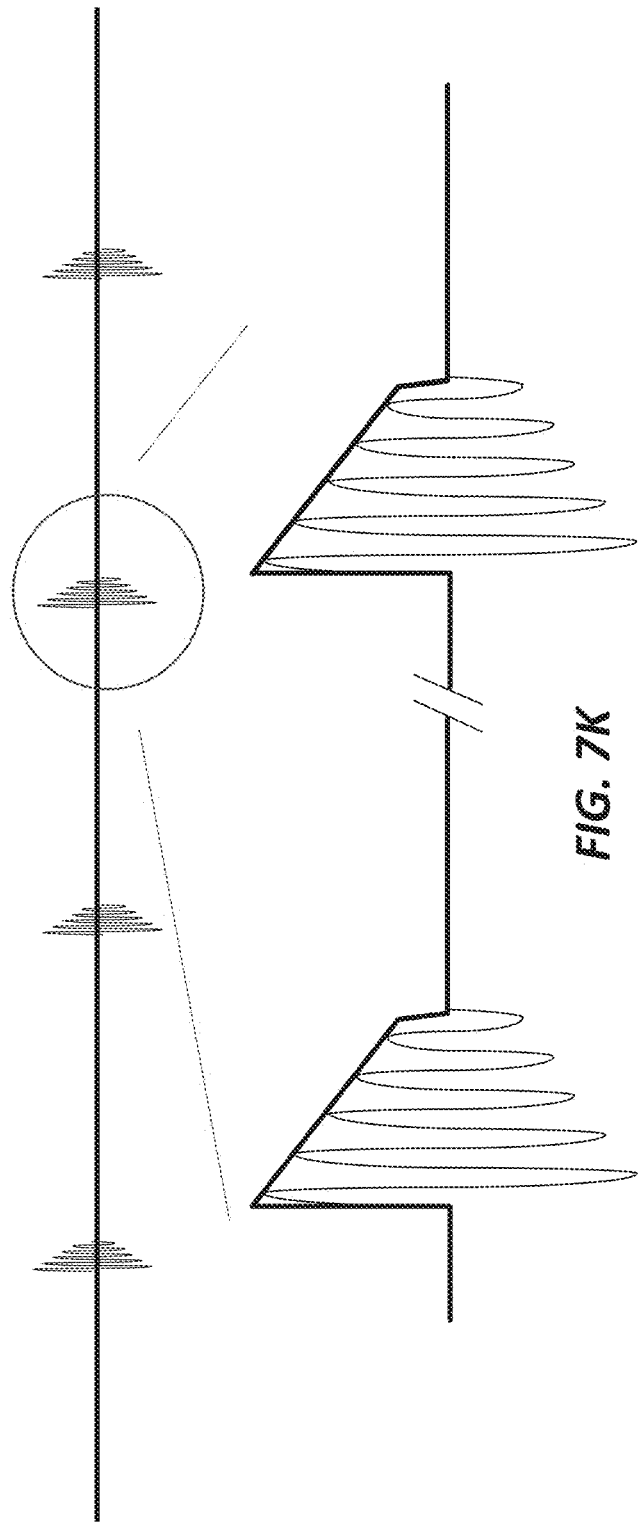
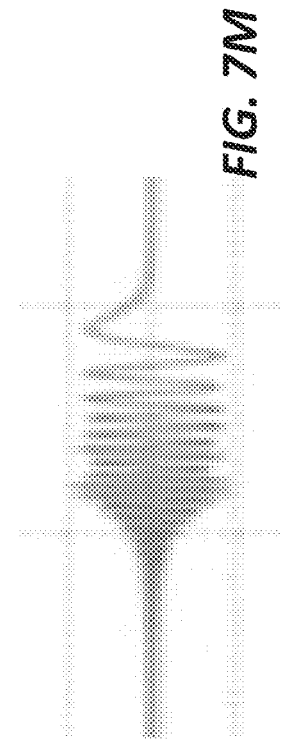
FIG. 7K
FIG. 7M
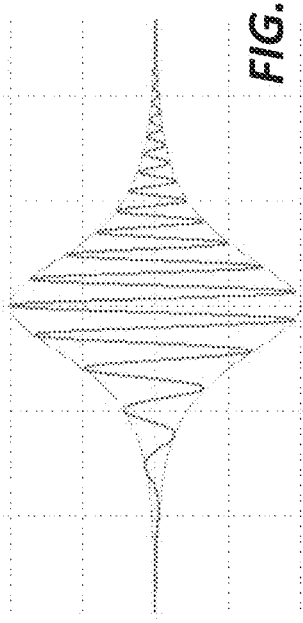
FIG. 7L

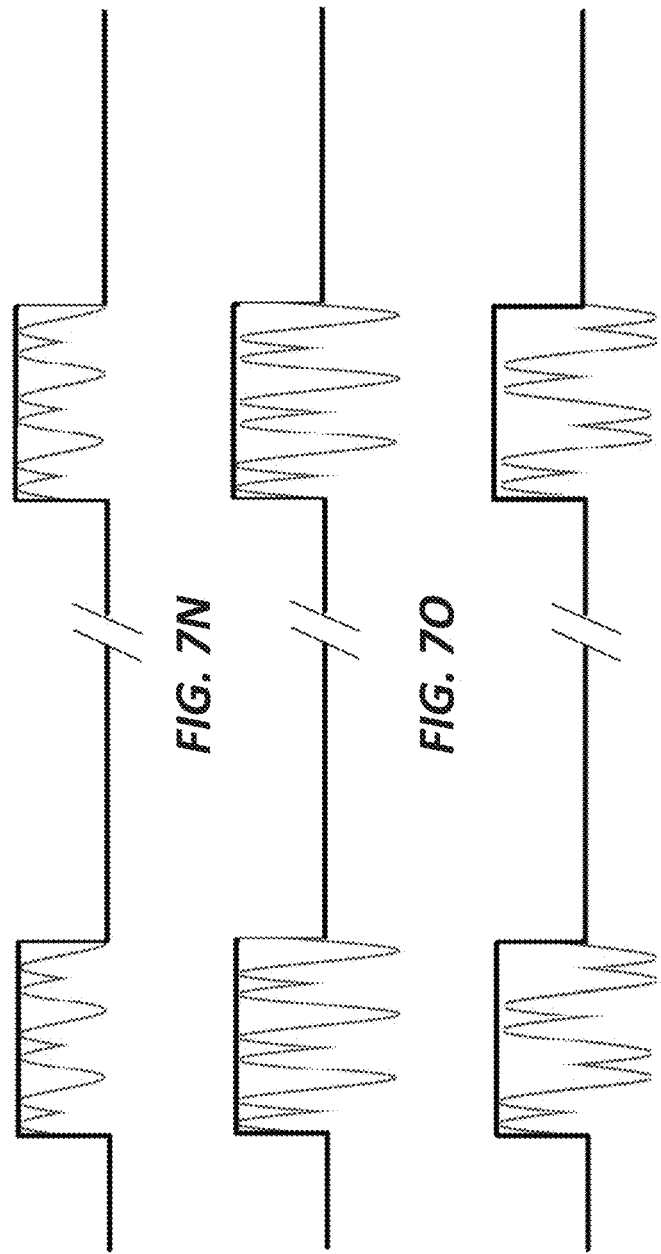

DEVICE AND METHOD TO SELECTIVELY AND REVERSIBLY MODULATE A NERVOUS SYSTEM STRUCTURE TO INHIBIT PAIN

CROSS-REFERENCE TO RELATED APPLICATIONS

This application claims priority to U.S. Provisional Application No. 62/776,908, filed Dec. 7, 2018, which is herein incorporated by reference in its entirety.

TECHNICAL FIELD

The present invention relates generally to a device and method to modulate neural and non-neural tissue activity to treat pain. In particular, a device and method to selectively and reversibly modulate neural- and non-neural tissue of a nervous structure to inhibit pain while preserving other sensory and motor function, and proprioception.

BACKGROUND OF THE INVENTION

Pain can be treated by both destructive and non-destructive methods by disrupting the transmission of pain signals that originate in the body from reaching the brain. Destructive methods are routinely used to treat chronic pain indications, and include thermal ablation, cryoablation, chemical ablations (e.g., via phenols, lidocaine, Botox™, ultrasonography ablation and mechanical transection). However, destruction of the nervous structure causes an immediate loss of functionality in the nerve and may lead to long-term atrophy, neuropathy and ultimately more pain. Additionally, mixed nerves and ganglia are typically not targeted using destructive interventions for chronic pain because of the desire to maintain motor and non-painful sensory function. Further, destruction of a nervous structure is not conducive to post-operative and peri-operative pain management, where motor and non-painful sensory function is desired to be preserved. Consequently, destructive methods for disrupting pain signals are generally not used for acute pain applications such as post-surgical pain.

Non-destructive methods to treat pain include the use of prescription pain medications (e.g., opioids), local anesthetic injections, topical or injected cocktails consisting of steroids and other anti-inflammatory agents, continuous infusion of local anesthetics, electrical blocking, electrical stimulation, and the application of pulsed radiofrequency energy. Each of these methods have a unique set of challenges that compromise treatment efficacy and usability. For instance, prescription pain medications come with unwanted side effects and can lead to addiction. Meanwhile, local anesthetic and cocktail injections have a short effective duration that only lasts for a few hours, while continuous infusion of anesthetics requires an external device be tethered to the patient for long-term treatment (days). Additionally, the use of local anesthetics presents a risk of nerve toxicity, vascular toxicity and allergic reactions. Lastly, these agents are not selective to the type of nerve activity that they block (e.g., they block both nerve fiber activity associated with pain and nerve fiber activity associated with motor function).

Electrical neuromodulation techniques pose a lower risk of side-effects than chemical interventions and provide adjustable, regional management of pain. However, existing electrical blocking technologies are only being used to treat chronic post-amputation pain and require an internal pulse generator and nerve cuff be implanted in the patient for long-term blocking. As such, the need for surgical implantation considerably burdens the use of electrical blocking for acute pain applications in both small and large nerves, as well electrical blocking of acute head and face pain. Moreover, even though electrical stimulation devices are commonly used to mitigate pain, their efficacy thus far has not been sufficient to manage moderate to severe pain levels, such as the pain levels experienced by a patient suffering from severe or chronic migraine, peri-operative pain and/or post-operative pain experience in the days to weeks following surgery. Electrical nerve stimulation devices have also been used in peripheral nerves, on the dorsal root ganglia, and in the spinal cord to treat chronic pain, however, these devices are all burdened by the need for surgical implantation and may undesirably activate motor fibers or non-painful sensory fibers when applied to mixed nerves or ganglia. Further, although radiofrequency energy treatment is procedural-based, and the patient is not burdened by a take-home device, it cannot be used to treat large nerves, and the treatment outcomes are inconsistent for small nerves. Additionally, the selectivity and time-course of reversibility of radiofrequency energy treatment for acute pain is unknown.

As such, there is a need for an electrical device and method that can temporarily and selectively inhibit pain by modulating neural and non-neural activity in both small-diameter and large-diameter peripheral nerves, cranial nerves, ganglia, autonomic nerves, plexuses and the spinal cord, with effects that last for days-to-weeks, where the temporary and selective blocking does not run the risk of neural toxicity, vascular toxicity or allergy.

SUMMARY OF THE INVENTION

The present disclosure is directed to a system and method for selectively and reversibly modulating targeted neural and non-neural tissue of a nervous system for the treatment of pain. An electrical stimulation is delivered to the treatment site that selectively and/or reversibly modulates the targeted neural- and non-neural tissue of the nervous structure, inhibiting pain while preserving other sensory and motor function, and proprioception. In an aspect, a system is disclosed for selectively and/or reversibly modulating targeted neural- and non-neural tissue of a nervous system structure (e.g., to treat a medical condition of a patient). The system includes an electrical stimulation device comprising one or more electrodes (e.g., having a size-, shape-, and contact-surface-configuration suitable to deliver an electrical stimulation to the nervous system structure) (e.g., monopolar or bipolar) (e.g., a single electrode or an array of electrodes) that delivers an electrical stimulation to a treatment site proximate the targeted neural- and non-neural tissue of the nervous system structure; and a controller configured to connect to the one or more electrodes of the electrical stimulation device and to a power source for supplying electrical energy to the one or more electrodes, where the controller is configured to direct operation of the electrical stimulation device (e.g., via current controlled, voltage controlled, power controlled, and/or temperature controlled) and to apply the electrical stimulation to the treatment site through the electrode, and wherein the application of the electrical stimulation to the treatment site selectively modulates the targeted neural- and non-neural tissue inhibiting pain and preserving other sensory and motor function, and proprioception.

In some embodiments, the pain comprises at least one of acute pain, post-surgical pain, neuropathic pain, chronic pain, and head-and-face pain.

In some embodiments, a single application of the electrical stimulation to the treatment site selectively modulates the targeted neural- and non-neural tissue resulting in subsequent inhibition of pain (e.g., for a period of about 1 day to about 30 days, for a period of about 30 days to about 60 days, for a period of about 60 days to about 90 days, for a period of about 90 days to about 120 days, for a period of about 120 days to about 150 days, for a period of about 150 days to about 180 days, for a period of about 180 days to about 270 days, for a period of about 270 days to about 365 days) (e.g., where the pain is chronic pain, a single application of the electrical stimulation to the treatment site selectively modulates the targeted neural- and non-neural tissue resulting in subsequent inhibition of pain for a period of about 90 days to about 365 days).

In some embodiments, the single application of the electrical stimulation to the treatment site selectively modulates the targeted neural- and non-neural tissue resulting in subsequent inhibition of pain, for a period of about 5 days to about 30 days.

In some embodiments, the application of the electrical stimulation to the treatment site modulates (e.g., selectively modulates and/or reversibly modulates) the targeted neural- and non-neural tissue inhibiting nerve signal transmission through nerve fibers that are responsible for the transmission of pain (e.g., and for transmission of thermoception, autonomic activity and visceral function, wherein nerve signal transmission through nerve fibers is responsible for other sensory and motor function, and proprioception is preserved, and wherein the other sensory function is selected from the group consisting of touch, vision, audition, gustation, olfaction, and balance.

In some embodiments, the one or more electrodes are configured (e.g., suitably sized and shaped) to be positioned adjacent the nervous system structure comprising at least one of a peripheral nerve, a cranial nerve, a ganglia, and an autonomic nerve, a plexus, and a spinal cord (e.g., wherein the ganglia comprises at least one of dorsal root ganglia, a sympathetic ganglia, a parasympathetic ganglia, a sphenopalatine ganglia, a gasserian ganglion).

In some embodiments, the nervous system structure comprises a nerve or ganglia (e.g., a cranial nerve, autonomic nerve, plexus, and spinal cord) having a diameter greater than about 2.5 mm, wherein at least one of the one or more electrodes has a size and shape and contact surface configuration (e.g., surface area ranging from 1 mm$^2$ to about 100 mm$^2$) sufficient to deliver an electrical stimulation to the nerve or ganglia (e.g., wherein the controller is configured to generate a suitable waveform forming the electrical stimulation to modulate (e.g., selectively modulate or reversibly modulate) the targeted neural- and non-neural tissue of the nervous system structure).

In some embodiments, wherein the application of the electrical stimulation to the treatment site selectively inhibits nerve signal transmission through at least one of a myelinated Aδ fiber and an unmyelinated C fiber provided in the peripheral nerve while preserving nerve signal transmission through at least one of the Aβ and Aα fibers, and/or motor fibers.

In some embodiments, wherein the application of stimulation to the treatment site selectively inhibits nerve signal transmission through at least one of myelinated Aδ fiber and an unmyelinated C fiber provided in the peripheral nerve while preserving nerve signal transmission through at least one of the Aβ and Aα fibers, and/or motor fibers in a neighboring nerve or neighboring nerve fascicle.

In some embodiments, the controller is adjustable to vary the electrical stimulation (e.g., a parameter of the electrical stimulation) based on a measured feedback selected from the group consisting of: measured inhibition of nerve signal transmission, measured temperature (e.g., at the treatment site, at the one or more electrodes or a portion thereof, at the electrical stimulation device, at the patient's skin), input from the patient (e.g., regarding pain sensation), a feedback corresponding to at least one of the adjustable parameters of the electrical stimulation, a treatment setting associated with a time-course of recovery, electrode contact impedance, electrical field generated in the tissue, patient physiological response (e.g., blood flow, skin conductance, heart rate, muscle activity (e.g., such as electromyography)), and a combination thereof.

In some embodiments, the controller is configured to vary the duty cycle and/or stimulation waveform envelope duration of the electrical stimulation in real-time to maximize voltage delivered to the tissue, while not exceeding a target tissue temperature at the treatment site (e.g., modulate stimulation duty cycle and/or stimulation envelope to maximize voltage without exceeding a destructive tissue temperature at the treatment site).

In some embodiments, the controller is configured to vary the duty cycle and/or the stimulation waveform envelope duration of the electrical stimulation in real-time to maximize current delivered to the tissue, while not exceeding a target tissue temperature at the treatment site (e.g., modulate stimulation duty cycle or stimulation envelope to maximize current without exceeding a destructive tissue temperature.)

In some embodiments, the controller is adjustable to vary at least one parameter of the electrical stimulation to modulate (e.g., selectively inhibit and/or reversibly inhibit) nerve signal transmission through either i) at least one of the myelinated Aδ fibers and/or the unmyelinated C fibers or ii) a large nerve or large ganglia or large neural structure (e.g., a cranial nerve, a ganglia, an autonomic nerve, a plexus, a spinal cord, a dorsal root ganglia, a sympathetic ganglia, a parasympathetic ganglia, a sphenopalatine ganglion, a gasserian ganglion), wherein the at least one parameter is selected from the group consisting of a waveform shape, a waveform frequency, a waveform amplitude, waveform envelope duration, an electrical field strength generated at the electrode (e.g., as measured at the electrode or at the treatment site), a waveform DC offset, a waveform duty cycle, a tissue temperature, a cooling mechanism parameter (e.g., rate of cooling, flow rate of cooling medium, cooling medium pressure, measured temperature at treatment site or at portion of cooling mechanism), and a treatment duration.

In some embodiments, the nervous system structure comprises a peripheral nerve, wherein the controller is adjustable to apply the electrical stimulation to differentially inhibit function of the myelinated Aδ fibers or nerve fibers responsible for a sensation of sharp/stabbing pain (e.g., wherein the myelinated Aδ fibers and/or nerve fibers responsible for the sensation of sharp/stabbing pain have a larger percentage of fibers inhibited than the unmyelinated C fibers or nerve fibers responsible for a sensation of dull/aching pain).

In some embodiments, the nervous system structure comprises a peripheral nerve, wherein the controller is adjustable to apply the electrical stimulation to differentially inhibit function of the unmyelinated C fibers or nerve fibers responsible for a sensation of dull/aching pain (e.g., wherein the unmyelinated C fibers and/or nerve fibers responsible for the sensation of dull/aching pain have a larger percentage of fibers inhibited than the myelinated Aδ fibers).

In some embodiments, the controller is adjustable to vary at least one parameter of the electrical stimulation to modulate (e.g. selectively modulate and/or reversibly modulate) nerve signal transmission within a portion of the nervous system structure having a cross-section less than or equal to the complete cross-section of the nervous system structure.

In some embodiments, the controller is adjustable to vary at least one parameter of the electrical stimulation to reduce an onset response of the nervous system structure and/or an activation of the nervous system structure at the onset of inhibition of the nervous system structure.

In some embodiments, the controller is adjustable to deliver electrical stimulation to the treatment site having a frequency selected from the group consisting of about 100 kHz, about 200 kHz, about 300 kHz, about 400 kHz, about 500 kHz, about 600 kHz, about 700 kHz, about 800 kHz, about 900 kHz and about 1 MHz.

In some embodiments, the electrical stimulation delivered to the treatment site has an amplitude range between about 5 mA (e.g., peak-to-center, corresponding to 10 mA peak-to peak) and about 1.25 A (peak-to-center, corresponding to 2.5 A peak-to-peak).

In some embodiments, the electrical stimulation delivered to the treatment site has an amplitude range between about 10 V and about 500 V (peak-to-center, corresponding to 20-1000 V peak-to-peak).

In some embodiments, the electrical stimulation delivered to the treatment site has a power range between about 0.1 W and about 1,250 W.

In some embodiments, the electrical stimulation delivered to the treatment site generates or induces an electrical field strength at the target site and/or electrode between about 20 kV/m and about 2,000 kV/m.

In some embodiments, the electrical stimulation delivered to the treatment site has a waveform shape component (e.g., a continuously outputted waveform or an intermittently outputted waveform (e.g., pulsed for a predefined duration)) (e.g., as a charge-balanced waveform or as a non-charge-balanced waveform) including at least one of a sinusoidal waveform, a square waveform, a triangular waveform, an impulse waveform, a shape modulated waveform, a frequency modulated wave form, an amplitude modulated waveform that provides a continuous delivery of electrical stimulation (e.g., a chirp) at the treatment site and a combination (e.g., additive combination) thereof.

In some embodiments, the electrical stimulation delivered to the treatment site has a duty cycle between about 0.1% and about 99%.

In some embodiments, the electrical stimulation delivered to the treatment site has an inter-pulse width between about 1 ms and about 999 ms.

In some embodiments, the electrical stimulation is delivered to the treatment site for a duration up to 30 minutes.

In some embodiments, the controller is adjustable to apply the electrical stimulation while maintaining the tissue temperature between about 5° C. and about 60° C.

In some embodiments, the electrical stimulation device comprises a device body configured to be implanted within the patient at a location adjacent the treatment site (e.g., percutaneously placed or implanted).

In some embodiments, the controller comprises a stimulator (e.g., a function or waveform generator) (e.g., an external function or waveform generator), the stimulator being coupled to both the electrode and an interface of the controller, where operation of the stimulator is directed by the controller to provide the electrical stimulation to the electrode.

In some embodiments, the electrode comprises an electrode assembly in the form of a paddle, cuff, cylindrical catheter or needle, wire form, or thin probe.

In some embodiments, the one or more electrodes are sized and/or shaped (e.g., an electrical contact of the electrode has a surface area ranging from about 1 $mm^2$ to about 100 $mm^2$) to maximize and direct the electrical field toward the nervous system structure.

In some embodiments, the one or more electrodes comprise at least two electrical contacts (e.g., wherein the at least two electrical contacts are configured to be positioned near the nervous system structure during treatment) (e.g., wherein the controller is configured to independently operate (e.g., in a multipolar manner to direct current of the resultant electric field) each of the at least two electrical contacts).

In some embodiments, each of the electrical contacts are located on a single lead, forming a stimulation pair (e.g. cathode and anode).

In some embodiments, each of the electrical contacts are between about 1 and 50 mm in length (e.g., preferably between about 1 mm and about 30 mm, between about 2 mm and about 20 mm in length, between about 2 mm and about 15 mm in length, or about 5 mm and 10 mm in length).

In some embodiments, the length of each of the electrical contacts is the same.

In some embodiments, the length of each of the electrical contacts is different.

In some embodiments, where the at least two electrical contacts include a distal electrical contact adjacent a distal end of the electrode and a proximal electrical contact located along the electrode at a location between the distal electrical contact and a proximal end of the electrode, and wherein a length of the distal electrical contact is greater than a length of the proximal electrical contact (e.g. the length of the distal electrical contact may be about 10 mm in length, and the length of the proximal electrical contact may be about 4 mm in length).

In some embodiments, the one or more electrodes comprise an electrode assembly in the form of an elongated body, the distal end of the elongated body including a bend such that a distal tip portion of the elongated body extends at an angle with respect to a longitudinal axis of the elongated body, wherein the angle of the distal tip portion with respect to the longitudinal axis of the elongated body is between about 0 and about 50 degrees (e.g., preferably between about 5 and about 15 degrees).

In some embodiments, the distal tip portion of the elongated body is straight.

In some embodiments, the distal tip portion of the elongated body is curved.

In some embodiments, the electrode assembly includes at least two electrical contacts comprising a distal electrical contact provided on the distal tip portion of the elongated body and a proximal electrical contact provided along the elongated body between the distal tip portion and a proximal end of the electrode assembly.

In some embodiments, the distal electrical contact is sized and configured to interface with targeted neural- and non-neural tissue of the nervous system structure, and the proximal electrical contact is sized and configured to be positioned in subcutaneous tissue (e.g., fat, fascia, muscle).

In some embodiments, each of the one or more electrodes comprise at least two electrical contacts, where each of the electrical contacts are located on a same side of the elongated body of the electrode.

In some embodiments, the conductive regions of each of the electrical contacts are on the same side of the elongated body and do not deliver electrical energy circumferentially to a portion of a circumference of the elongated body without electrical contacts (e.g., the electrical contact do not deliver electrical energy circumferentially to a short-axis of the lead thereby providing voltage-field shaping and current steering).

In some embodiments, the system further includes a resistor positioned electrically in series an electrical contact included in the one or more electrodes.

In some embodiments, the electrical contacts provided on the one or more electrodes are formed from a material with higher impedance or with high levels of capacitance.

In some embodiments, the electrical contacts provided on the one or more electrodes have a smooth curvilinear shaped perimeter.

In some embodiments, the electrical contacts provided on the one or more electrodes have an oval shaped perimeter.

In some embodiments, the electrical contacts provided on the one or more electrodes have a rectilinear shaped perimeter.

In some embodiments, the system further includes temperature measuring device (e.g. thermocouple, thermistor) provided on the one or more electrodes for providing tissue temperature measurement.

In some embodiments, at least one of an electrical contact and a temperature measuring device provided on the one or more electrodes is printed from electrically and thermally conductive material.

In some embodiments, the electrical contacts provided on the one or more electrodes extend partially around a circumference of the corresponding electrode, where an arc length of the electrical contact is less than 180 degrees such that the electrical contact extends around less than half of the circumference of the electrode.

In some embodiments, the electrode is electrically coupled to the controller via a circumferentially-shaped contact surface provided on the electrode and a corresponding circumferentially-shaped contact surface provided on a lead electrically coupled to the controller.

In some embodiments, the circumferentially-shaped contact surface includes more than one circumferentially-shaped contact surfaces arranged concentrically around the longitudinal axis of the electrode (e.g., four circumferentially-shaped contact surfaces of varying diameter), wherein a lead electrically coupled between the electrode and the generator includes a corresponding more than one circumferentially-shaped contact surfaces arranged concentrically around a longitudinal axis of the lead (e.g., four circumferentially-shaped contact surfaces of varying diameter).

In some embodiments, the circumferentially-shaped contact surfaces of the electrode are separated by a dielectric layer (e.g., electrically insulating materials and/or air provided between adjacent conductive surfaces), wherein the circumferentially-shaped contact surfaces of the lead are separated by a dielectric layer (e.g., electrically insulating materials and/or air provided between adjacent conductive surfaces).

In some embodiments, the electrical circuitry of the electrodes extends within the electrode within the circumferentially-shaped contact surface.

In some embodiments, at least one of the one or more electrodes is a monopolar electrode configured to be positioned at a contact surface of the stimulation device, and a return electrode is positioned on an outer surface of the patient's skin.

In some embodiments, the stimulation device is reusable.

In some embodiments, the stimulation device is disposable.

In some embodiments, the system further comprises a user interface (e.g., comprising a display (e.g., to provide an indication of status of the controller, stimulation device, patient)), wherein the user interface is configured to receive an input from the user to direct the application of the electrical stimulation to the treatment site (e.g., to vary inhibition of pain (while preserving other sensory and motor function, and proprioception).

In some embodiments, the system further comprises a display coupled to at least one of the controller and the stimulation device, the display providing an indication of a status of the stimulation device.

In some embodiments, the system further comprises a temperature sensor (e.g., thermistor, thermocouple) coupled to the stimulation device for measuring a temperature of at least one of i) a contact surface of the stimulation device and ii) the patient's tissue adjacent the contact surface or electrode, the temperature sensor coupled to the controller and provides thermal feedback information regarding a measured temperature, wherein the controller is adjustable to vary at least one parameter of the electrical stimulation (e.g., by the controller or by the user) in response to the thermal feedback information received from the temperature sensor (e.g., to adjust a temperature of the contact surface and maintain the temperature of the patient's tissue below a destructive tissue temperature and/or maintain the temperature of the contact surface of the stimulation device below the destructive tissue temperature).

In some embodiments, the system further comprises a cooling mechanism configured to provide a cooling effect at the treatment site (e.g., contact surface of the stimulation device), wherein the cooling effect prevents damage (e.g., by pre-cooling or maintaining temperature when the electrical stimulation is delivered) at the treatment site (e.g., by preserving temperatures of the patient's tissue below a destructive tissue temperature).

In another aspect, a method is disclosed for selectively and reversibly modulating targeted neural- and non-neural tissue of a nervous system structure with the application of electrical stimulation (e.g., a single application of electrical stimulation) to treat a medical condition of a patient. The method comprises identifying a targeted nervous system structure; positioning an electrical stimulation device at a treatment site proximate the targeted neural- and non-neural tissue of the nervous system structure, the electrical stimulation device comprising an electrode that provides an electrical stimulation to the treatment site; delivering an electrical stimulation to the treatment site via the electrode; wherein the application of the electrical stimulation to the treatment site selectively modulates the targeted neural- and non-neural tissue of the nervous system structure inhibiting pain and preserving other sensory and motor function, and proprioception; and wherein the application of the electrical stimulation to the treatment site selectively modulates the targeted neural- and non-neural tissue and subsequent inhibition of pain (e.g., for a period of about 1 day to about 30 days, for a period of about 30 days to about 60 days, for a period of about 60 days to about 90 days, for a period of about 90 days to about 120 days, for a period of about 120 days to about 150 days, for a period of about 150 days to about 180 days, for a period of about 180 days to about 270 days, for a period of about 270 days to about 365 days).

In some embodiments, the nervous system structure comprises at least one of a peripheral nerve, a cranial nerve, a ganglia (e.g., wherein the ganglia comprises at least one of dorsal root ganglia, a sympathetic ganglia, a parasympathetic ganglia, sphenopalatine ganglion, gasserian ganglion, plexus, spinal cord), an autonomic nerve, and autonomic ganglia.

In some embodiments, the application of the electrical stimulation to the treatment site selectively modulates the targeted neural- and non-neural tissue inhibiting nerve signal transmission through nerve fibers that are responsible for the transmission of pain, wherein nerve signal transmission through nerve fibers responsible for other sensory and motor function, and proprioception is preserved, and wherein other sensory function includes at least one of touch, vision, audition, gustation, olfaction, and balance.

In some embodiments, the pain comprises at least one of acute pain, surgical pain, post-surgical pain, trauma pain, neuropathic pain, chronic pain, and head-and-face pain.

In some embodiments, the pain is acute pain, wherein the electrical stimulation is applied at least one of immediately prior to a surgical procedure, intraoperatively, and immediately following a surgical procedure or trauma.

In some embodiments, the electrical stimulation is delivered to the treatment site more than 24 hours prior to a surgical procedure.

In some embodiments, where the pain is post-surgical pain following a knee arthroplasty procedure, wherein the electrical stimulation is applied to the femoral nerve, the sciatic nerve, the obturator nerve, and the lateral cutaneous nerve and nerve branches, or a combination thereof.

In some embodiments, where the pain is shoulder pain, the electrical stimulation is applied to the brachial plexus, the axillary nerve, the suprascapular nerve and lateral pectoral nerve, or a combination thereof.

In some embodiments, where the pain is associated with a medical procedure and/or trauma to the arm and/or hand, the electrical stimulation is applied to the medial, ulnar and radial nerves individually or the brachial plexus, or a combination thereof.

In some embodiments, where the pain is associated with a medical procedure and/or trauma to the ankle and/or foot, the electrical stimulation is applied to the tibial, peroneal/sural and saphenous nerves, or a combination thereof.

In some embodiments, where the pain is associated with a hip arthroplasty, the electrical stimulation is applied to the femoral, sciatic, or obturator (e.g., common obturator before branching into anterior and posterior) nerves and/or plexus, or a combination thereof.

In some embodiments, where the pain is associated with repair of the anterior cruciate ligament (ACL), the electrical stimulation is applied to the femoral, or sciatic nerve, or a combination thereof.

In some embodiments, the pain is neuropathic pain or chronic pain, the electrical stimulation is used to provide an on-demand bolus of therapeutic treatment.

In some embodiments, the step of positioning the electrical stimulation device proximate the treatment site comprises: positioning the electrode adjacent the nervous system structure percutaneously through an opening in the patient's skin; or implanting the electrode within the patient at a location adjacent the treatment site.

In some embodiments, the step of positioning the electrical stimulation device proximate the treatment site further comprises: delivering an initial electrical stimulation to the treatment site via the electrode; measuring at least one of a voltage and a current at the electrode; and adjusting a position of the electrode at the treatment site until the measured voltage and current corresponding to a threshold voltage and a threshold current, respectively.

In some embodiments, the method further includes adjusting at least one parameter of the electrical stimulation to selectively inhibit nerve signal transmission through the targeted neural- and non-neural tissue, wherein the at least one parameter is selected from the group consisting of a waveform shape, a waveform frequency, a waveform amplitude, a waveform envelope duration, an electrical field strength generated at the electrode (e.g., measured at the electrode or at the treatment site), a waveform DC offset, a waveform duty cycle, a tissue temperature, a cooling mechanism parameter (e.g., rate of cooling, flow rate of cooling medium, cooling medium pressure, measured temperature at treatment site or at portion of cooling mechanism), and a treatment duration.

In some embodiments, the method further includes modulating the duty cycle or waveform envelope duration of the electrical stimulation in real-time to maximize voltage delivered to the treatment site while not exceeding a target tissue temperature at the treatment site (e.g., modulating the stimulation duty cycle or stimulation envelope to maximize voltage without exceeding a destructive tissue temperature at the treatment site).

In some embodiments, the method further includes modulating the duty cycle or waveform envelope duration of the electrical stimulation in real-time to maximize current delivered to the treatment site while not exceeding a target tissue temperature at the treatment site (e.g., modulate stimulation duty cycle or stimulation envelope to maximize current without exceeding an irreversible destructive tissue temperature).

In some embodiments, the method further includes slowly ramping a stimulation amplitude of the electrical stimulation to an amplitude plateau.

In some embodiments, the method further includes adjusting the controller to vary the electrical stimulation based on a measured feedback selected from the group consisting of: measured inhibition of nerve signal transmission, measured temperature (e.g., at the treatment site, at the one or more electrodes or a portion thereof, at the electrical stimulation device, at the patient's skin), input from the patient (e.g., input regarding pain), a feedback corresponding to at least one of the adjustable parameters, a treatment setting associated with a time-course of recovery, electrode contact impedance, electric field generated in the tissue, patient physiological response (e.g., blood flow, skin conductance, heart rate, muscle activity (e.g., such as electromyography)), and a combination thereof.

In some embodiments, the electrode comprises a first and second electrode that operate independently, wherein delivering an electrical stimulation to the treatment site via the electrode further comprises delivering a first electrical simulation via the first electrode and delivering a second electrical stimulation via the second electrode, where the first and second electrical stimulations are intermittently outputted, where the first electrical stimulation is interleaved with respect to the second electrical stimulation such that an on cycle of the first electrical stimulation occurs during an off cycle of the second electrical stimulation and an on cycle of the second electrical stimulation occurs during an off cycle of the first electrical stimulation.

In some embodiments, the method further includes measuring, at a temperature sensor (e.g., thermistor, thermocouple), a temperature of at least one of a contact surface of the stimulation device and the patient's tissue adjacent the contact surface during delivery of the electrical stimulation, wherein the temperature sensor provides thermal feedback information regarding a measured temperature to the stimulation device; and adjusting the electrical stimulation (e.g., adjusting a parameter of the electrical stimulation) in response to the thermal feedback information received from the temperature sensor to create a cooling effect at least one of the contact surface of the stimulation device and the patient's tissue adjacent the contact surface.

In some embodiments, the method further includes measuring, at a temperature sensor (e.g., thermistor, thermocouple), a temperature of at least one of a contact surface of the stimulation device and the patient's tissue adjacent the contact surface during delivery of the electrical stimulation, wherein the temperature sensor provides thermal feedback information regarding the measured temperature to the stimulation device; activating a cooling mechanism to cool the contact surface of the stimulation device in response to the thermal feedback information received from the temperature sensor, where cooling the contact surface prevents damage to the patient's tissue when the electrical stimulation is delivered by preserving temperatures of the patient's tissue below a destructive tissue temperature, and activating a cooling mechanism to maintain the temperature of the contact surface of the stimulation device below the destructive tissue temperature in response to thermal feedback information regarding the measured temperature received from the temperature sensor.

In another aspect, a non-transitory computer readable medium is disclosed. The computer readable medium having instructions stored thereon, wherein execution of the instructions by a processor causes the processor to perform any of the above-recited methods.

The details of one or more embodiments of the invention are set forth in the accompanying drawings and description below. Other features, objects, and advantages of the invention will be apparent from the description and drawings, and from the claims

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 7B, 7C, 7D, 7E, 7F, 7G, 7H, 7I, 7J, 7K, 7L, 7M, 7N, 7O, and 7P each show a waveform shape for an electrical stimulation;

Like reference symbols in the various drawings indicate like elements.

Definitions

Figure 1:
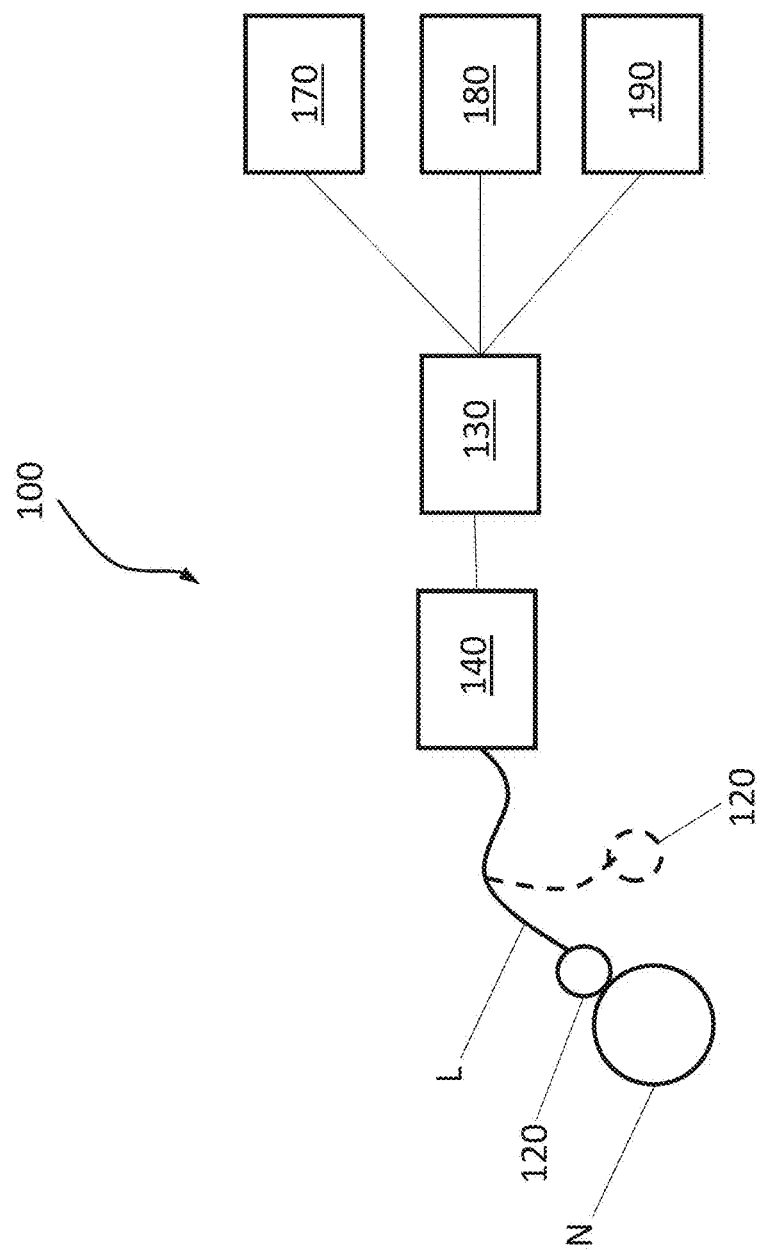
FIG. 1 is a schematic representation of an example electrical stimulation device.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

The terms "proximal" and "distal" are used herein as relative terms that refer to regions of a nerve, positions of nerves, or regions of a stimulation device. "Proximal" means a position closer to the spinal cord, brain, or central nervous system, whereas "distal" indicates a position farther from the spinal cord, brain, or central nervous system. When referring to the position on a neural structure in the peripheral nervous system or along an appendage, proximal and distal refer to positions either closer to the central nervous system or further from the central nervous system along the pathway followed by that neural structure or appendage. When referring to the position on a neural structure in the spinal cord, proximal and distal refer to positions either closer to the brain or further from the brain along the pathway followed by the neural structure.

Throughout the description and claims of this specification, the word "comprise" and variations of the word, such as "comprising" and "comprises," means "including but not limited to," and is not intended to exclude, for example, other additives, components, integers or steps. "Exemplary" and "e.g." means "an example of" and is not intended to convey an indication of a preferred or ideal aspect. "Such as" is not used in a restrictive sense, but for explanatory purposes.

As used herein, the term "nervous structure" or "neural structure" refers to a structure including neural and non-neural tissue. In addition to neural tissue (such as neurons and components of neurons including axons, cell bodies, dendrites and synapses of neurons), nervous structures may also include non-neural tissue such as glial cells, Schwann cells, myelin, immune cells, connective tissue, epithelial cells, neuroglial cells, astrocytes, microglial cells, ependymal cells, oligodendrocytes, satellite cells, cardiovascular cells, blood cells, etc.

As used herein, the term "stimulating electrode," also referred to in the case of monopolar stimulation as "the cathode", refers to an electrode responsible for delivering the therapeutic energy to the nerve. In the case of bipolar or multipolar stimulation, all of the electrical contacts are considered to be stimulating electrodes.

As used herein, "return electrode," also referred to in the case of monopolar stimulation as "the anode," refers to an electrode responsible for providing a return path for current that flows through the body. For example, the return electrode provides a return path for the current which is delivered to the target neural structure via the stimulating electrode.

As used herein, "electrical signal," "electric signal," "electrical simulation," "stimulation electric signal," "stimulation electrical signal" and "stimulation waveform" refer to the electrical signal delivered by the controller to the tissue by means of the stimulating electrodes or, in the case of monopolar stimulation by means of the stimulating electrode and the return electrode. For example, the electrical signal may be described as a temporally-varying voltage, current, power, or other electrical measure. The delivery of the electrical signal to the target tissue is referred to as an electrical treatment, an electrical therapy, or simply a treatment or a therapy. The electrical signal creates an electrical field in the tissue such that control of the electrical signal strongly influences control of the electrical field in the tissue.

As used herein, "treatment site" refers to the site on the neural and non-neural structure to which the electrical signal is delivered by means of the electrode(s).

As used herein, "modulate" refers to modifying or changing the transmission of information. For example, this includes both excitation, pacing, and inhibition/interruption of the passage of impulses along a neuron's axon within a nerve. Modulating nerve fiber activity includes inhibiting nerve signal transmission to the point of creating a blocking effect, including a partial and a complete blocking effect. Modulating nerve activity also includes modifying the trafficking of molecules such as macromolecules along the nerve fiber. Modulating nerve activity also includes changing downstream function of the neuron (for example at cell bodies and synapses), modifying signaling in a way that changes signaling in other neurons (for example neurons in the central nervous system such as the spinal cord or the brain), modifying the function of non-neural tissue in the neural structure, or otherwise modifying the processes, function, or activity in the target neural or non-neural tissue.

As used herein, the terms "inhibit" and "attenuate" refer to any level of reduction, including partial reduction or complete reduction of nerve signal activity through a nervous structure, e.g., the reduction of the passage of impulses along a neuron's axion within a nerve.

As used herein, "percutaneous" refers to electrical stimulation applied utilizing one or more electrodes penetrating through the surface of the skin so an electrode delivering electrical stimulation to a target nerve beneath the skin is also located beneath the skin. For percutaneous electrical stimulation, it is contemplated that return electrodes or anodes may be located beneath the skin or on the surface of the skin. The term "percutaneous electrode" refers to electrode assemblies inserted through the skin and directed into the vicinity of the nerve (mm to cm distance) in a minimally invasive fashion to electrically affect the physiology of the neural structure.

As used herein, the terms "pain sensation" or "painful sensation" refer to a disagreeable sensation generated, for example, by the activation of sensory nociceptors. Nociception describes the perception of acute pain and is generally caused by activation of sensory nociceptors or by disruption of nociceptor pathways (e.g. severed neurons or disrupted nociceptors). Chronic pain sensation can also be generated by activation of nerve fibers which result in a disagreeable perception similar in nature to that generated by activation of nociceptors (for example, neuropathic pain). In some cases, such as following a surgery intended to treat chronic pain, both acute pain sensation and chronic pain sensation may contribute in a mixed manner to the overall pain sensation.

As used herein, the term "target nerve" is synonymous with "neural structure" or "nervous structure", and refers, for example, to mixed nerves containing motor nerve fibers and sensory nerve fibers. It may additionally refer to sensory nerves containing only sensory nerve fibers and/or to motor nerves containing only motor nerve fibers.

As used herein, the terms "transmucosal" refers to electrical stimulation applied to the mucosal tissue overlaying a targeted nervous structure using one or more electrodes. The electrical stimulation passes through the mucosal tissue to the targeted nervous structure.

As used herein, the terms "preserve" or "preserving" refer to cases where nerve function is partially but not completely maintained, as well as cases where a function is completely maintained. In comparative cases, one function may be inhibited while another function is preserved, suggesting that, in a comparative sense, the inhibited function has experienced a magnitude of reduction greater than the magnitude of reduction experienced by the preserved function. Specifically, in comparative cases, inhibition of one function and preservation of another function does not require complete preservation or complete inhibition of either function or both functions.

DETAILED DESCRIPTION

Anatomy and Physiology

As provided above and as will be explained in more detail below, the present invention is directed to a device and method to selectively and reversibly modulate targeted neural- and non-neural tissue of a nervous structure by the application of an electrical signal to inhibit pain while preserving other sensory and motor function, and proprioception. The device and method can be used to treat acute pain (such as surgical pain, post-surgical pain, trauma pain), neuropathic pain, chronic pain, and head-and-face pain (such as migraine headache, cluster headache, an occipital neuralgia, tension headache, sinus headache, cervicogenic headache, postherpetic neuralgia, post-traumatic pain, chronic daily headache (transformed migraine)) via the application of an electrical signal to a targeted neural- and non-neural tissue of a nervous structure to modulate or inhibit nerve signaling.

Pain is a noxious perception generated in the conscious mind. In healthy humans, perception of pain is generated by activation of sensory nociceptors and subsequent transmission of nociceptive signaling to the brain along one or more neural pathways. Pain can be created by activation of a neural pathway, at any point along that neural pathway, that results in perception of pain. In healthy humans, pain-generating neural pathways are generally activated via sensory nociceptors, which are sensory nerve endings tuned to detect and signal noxious events (e.g. noxious mechanical or thermal damage to tissue). This type of pain generally represents a genuine noxious condition, and this type of pain subsides when the noxious condition is resolved. In cases where the noxious event is not a chronic tissue dysfunction, this type of pain is referred to as acute pain. In contrast, chronic pain represents conditions where pain-generating neural pathways are persistently modulated due to chronic tissue dysfunction or neural dysfunction. This may be due to genuine activation of sensory nociceptors at a site of chronically dysfunctional tissue or due to dysfunction of the neural tissue or tissue supporting the neural tissue that results in modulation at any point along pain-generating neural pathways.

Interventions to treat pain can be designed to either directly or indirectly modulate nerve signal transmission via pain-generating neural pathways at any level along these pathways. For example, direct blocking of axonal conduction in nerve fibers attached to sensory nociceptors can block perception of pain. As an additional example, indirect modulation of synaptic transmission in the spinal cord or nerve ganglia can be achieved by activating or blocking other inputs to the spinal cord or ganglia and may result in modulation along a pain-generating neural pathway. As another example, inhibition of parasympathetic outflow in the sphenopalatine ganglion can indirectly influence head and face pain, such as migraine, by modulating sensory input to the brain (for example via the superior salivatory nucleus). Thus, it is desired to target a variety of nervous structures when modulating and treating acute and chronic pain.

Targeted nervous structures include peripheral nerves (small diameter and large diameter), cranial nerves, ganglia, autonomic nerves, plexuses, and spinal cord. Ganglia comprise at least one of dorsal root ganglia, a sympathetic ganglia, a parasympathetic ganglia, a sphenopalatine ganglion, a gasserian ganglion, and autonomic ganglia in general. Generally, large peripheral nerves are those peripheral nerves having a diameter greater than about 2.5 mm. Example large peripheral nerves include, for example, the femoral nerve, sciatic nerve, vagus nerve, tibial nerve, peroneal nerve, median nerve, radial nerve, and ulnar nerve. Example small peripheral nerves include, for example, the saphenous nerve, sural nerve, genicular nerves, cranial nerves (such as trigeminal nerve and occipital nerve), obturator nerve, and distal portions of larger nerves (such as distal portions of the vagus, tibial, peroneal, median, radial, and ulnar nerves). Targeted ganglia can include dorsal root ganglia, sympathetic ganglia, parasympathetic ganglia, a sphenopalatine ganglion (SPG), a gasserian ganglion, plexuses, and the spinal cord. Each of these nervous structures includes neural tissue as well as non-neural tissue which supports the neural tissue and can influence transmission of information along pain-generating neural pathways. Example non-neural tissue can include, for example, glial cells, Schwann cells, myelin, immune cells, connective tissue, epithelial cells, neuroglial cells, astrocytes, microglial cells, ependymal cells, oligodendrocytes, satellite cells, cardiovascular cells, blood cells, etc. Neural tissue generally refers to neurons which include components such as axons, cell bodies, dendrites, receptor endings, receptors, and synapses.

Importantly, in the context of the present invention, modulation of neural tissue (neurons including components such as axons, cell bodies, dendrites, receptor endings, receptors, and synapses) and/or non-neural tissue (such as glial cells, Schwann cells, myelin, immune cells, connective tissue, neuroglial cells, astrocytes, microglial cells, ependymal cells, oligodendrocytes, satellite cells, cardiovascular cells, and blood cells, etc.) may be responsible in part or in whole for the therapeutic inhibition of perception of pain.

Peripheral nerves are primarily composed of axons, while other neural structures, such as ganglia and the spinal cord, include many components including axons, cell bodies, dendrites, and synapses. Within a nervous structure there is variability in the nature of these components, including, for example, variability in the size, shape, and interface with supporting non-neural tissue. For example, peripheral nerves often contain both large-diameter and small-diameter axons. Schwann cells are non-neural supporting cells which surround some axons and comprise an insulating cover rich in layers of lipid bilayers referred to as the myelin sheath. Some axons are surrounded by a myelin sheath, and some axons are not surrounded by a myelin sheath. Generally, the structure of different neural components is related to their function. For example, large-diameter axons typically transmit neural signals more-quickly than small-diameter axons due to the relatively large increase in axial conductance relative to a modest increase in membrane conductance as a function of diameter. Similarly, the presence of a myelin sheath on large-diameter axons further increases the speed of conduction velocity of the action potential by increasing the resistance to trans-membrane current flow between unmyelinated areas of the axon, referred to as nodes of Ranvier. Nodes of Ranvier are brief un-myelinated portions of the fibers; action potentials are relayed along the axon by a burst of trans-membrane current flow at each subsequent node of Ranvier. Peripheral nerve axons which generally transmit information from the periphery toward the central nervous system (e.g. sensory information including pain) are often referred to as afferent fibers, while axons which generally transmit information from the central nervous system toward the periphery (e.g. motor information) are often referred to as efferent fibers.

As used herein, the term "A fiber" refers to myelinated afferent or efferent peripheral axons of the somatic nervous system. Generally speaking, A fibers are associated with proprioception, somatic motor function, sensations of touch and pressure and also sensations of pain and temperature. A fibers generally have a diameter of about 1 to 22 micrometers (μm) and conduction velocities between about 2 meter per second (m/s) to more than 100 m/s. Each A fiber has dedicated Schwann cells forming the myelin sheath around the fiber. As described above, the myelin sheath has a high content of lipids, increasing the electrical resistance to trans-membrane current flow and contributes to the high conduction velocity of action potentials along the nerve fiber. A fibers include the alpha, beta, delta, and gamma fibers. The alpha, beta, and gamma A fibers have diameters ranging from 5 micrometers to 20 micrometers (μm) and are associated with motor function, low-threshold sensory function, and proprioception, but not pain. Delta A fibers are associated with pain, and have smaller diameters ranging from 1 micrometer to 5 micrometers (μm).

As used herein, the term "C-fiber" refers to non-myelinated peripheral axons of the somatic nervous system with conduction velocities of less than about 2 m/s. C fibers have a diameter of about 0.2 to 1.5 micrometers (μm) and include the dorsal root and sympathetic fibers and are primarily associated with sensations like pain and temperature, some limited mechanoreception, reflex responses, autonomic effector activity, and visceral function.

In a peripheral nerve, pain sensation that is perceived as dull and persistent is often referred to as 'slow pain' and is transmitted in peripheral nerves by C fibers which conduct neural signals relatively slowly. Pain sensation that is perceived as sharp and rapid is often referred to as 'fast pain' and is transmitted in peripheral nerves by Aδ fibers which have a higher conduction velocity than C fibers. Aδ fibers generally comprise small diameter sensory axons that are lightly myelinated, compared to the non-myelinated C fibers. Acute and chronic pain can involve both Aδ and C fibers.

In addition to the examples given for peripheral nerve axons, above, similar principles of structure and function for components of neural structures, such as axons, cell bodies, dendrites, receptor endings, receptors, and synapses apply for different neural structures including peripheral nerve, a cranial nerve, a ganglion, and an autonomic nerve, a plexus, and a spinal cord. The sub-cellular structures within components of non-neural and neural tissue, such as cell membranes, lipid bilayers, ion channels, mitochondria, microtubules, nucleus, vacuoles, and other components of the cytoplasm are also related to the function of such components of neural structures. Additionally, downstream structures (e.g. cellular and subcellular structures that are downstream from the site of treatment) can also be functionally and structurally impacted in a primary or secondary manner by nerve treatments (for example downstream modulation of gene transcription, synaptic transmission, epigenetics, or modulation along any one of a number of molecular signaling cascades in a neuron). The downstream molecular and cellular machinery, and even the between-cell connectivity and communication, can be vastly different for pain pathways vs. motor, non-painful sensory, and proprioceptive pathways.

As another example, the sphenopalatine ganglion consists of parasympathetic neurons, sympathetic neurons, and sensory neurons. Within the sympathetic ganglion, cell bodies and synapses are present for the parasympathetic neurons, but not for the sympathetic or sensory neurons. Rather, only axons of the sympathetic and sensory neurons pass through the sphenopalatine ganglion. The present device and method can be used to selectively and/or reversibly modulate nerve signal transmission in one of the neural structure types (e.g. cell bodies, synapses, axons) while not modulating the other neural structures present in the ganglion. For example, modulation or inhibition of transmission via the parasympathetic neuron pathway, for example by inhibiting transmission of signals via the cell bodies or synapses in the sphenopalatine ganglion, can be achieved while preserving signaling via the sympathetic pathways and at least some of the sensory pathways. As an additional example, modulation or inhibition of transmission via the small-diameter sensory neurons can be achieved while preserving signaling via the sympathetic, parasympathetic, and other sensory fiber pathways. As another example, modulation of the parasympathetic pathway and the small-diameter sensory pathway can be achieved while preserving signaling via all other pathways in the ganglion. Notably, each type of neural component within a neural structure can have its own unique supporting non-neural tissue which contributes to the ability to selectively target modulation via specific pathways As will be described in more detail below, the present device and method can be used to selectively and reversibly modulate nerve signal transmission, for example by inhibiting or blocking nerve signal transmission, to inhibit pain. This selective and reversible inhibition of pain does not present risk of neural toxicity, vascular toxicity or injectable-chemical allergy. The present device is non-destructive of the target nervous structure and is suitable to treat chronic pain indications without the risks of atrophy, neuropathy and pain, and lends itself nicely to acute pain indications where nerve(s) are treated before, during, or soon after surgery so that the patient can go home without a device yet still experience pain relief for a period of day to weeks post-operatively, such as after a joint replacement or other orthopedic procedure. In other words, a device in which long-term, direct contact with the target area or nerve to be treated (e.g., via an implantable generator and a nerve cuff) is not required. However, if desired and especially for chronic pain indications, the device may still be implanted or partially implanted and/or carried home with the patient.

Example Device

FIG. 1 provides a schematic representation of an example electrical stimulation device 100. The electrical stimulation device 100 can be used to selectively and reversibly modulate a targeted neural- and non-neural tissue of a nervous structure with application of an electrical signal to treat a medical condition of a patient. The stimulation device 100 comprises an electrode 120 that delivers electrical stimulation to the treatment site, e.g., delivers the electrical stimulation to the targeted neural and non-neural tissue of the nervous structure. The electrical stimulation can be delivered by a percutaneously-placed lead (L) and electrode 120, by an implanted lead (L) and electrode 120, or by an electrode 120 advanced through a body opening and positioned adjacent (e.g., near or in contact with) the mucosal tissue overlying the targeted nervous structure (e.g., sphenopalatine ganglion, gasserian ganglion). Example wherein the mucosal tissues include an oral mucosa, a nasal oral mucosa, a gastrointestinal (GI) tract mucosa, a bowel mucosa, a bladder mucosa. The electrode 120 generates an electric field at the treatment site that results in selective and reversible modulation of the nerve fiber activity to inhibit pain. As provided above, the "modulation" of nerve fiber activity includes both the excitation and inhibition/interruption the passage of impulses along a neuron's axon within a nerve and can include inhibiting nerve signal transmission to the point of creating a blocking effect.

The delivery of the electrical signal stimulation includes interactions with other nearby tissues. For example, in the case of percutaneous application and positioning of the electrode, the electrical signal stimulation is delivered via the electrode 120 which has penetrated and navigated through the patient's outer tissues, including their skin, fat, bone, and muscle, in order to provide placement of the electrode 120 proximate a target nervous structure. In this example, the electrical stimulation influences not only the target neural structure, but also surrounding tissue such as connective tissue, supporting tissues of the nervous structure, fat, bone, muscle, and cardiovascular tissues and cells such as those present in and around blood vessels. In the case of transmucosal application, the electrical signal stimulation is delivered via the electrode 120 which is placed adjacent (e.g., near or in contact with) the overlying mucosal tissue. The electrical stimulation may affect targeted nervous structure, as well as the tissues beneath and surrounding the electrode 120, the tissues interposed between the electrode 120 and the target nervous structure, as well as other surrounding tissues (including skin, fat, muscle, bone, cartilage, connective tissue, supporting tissues of the nervous structure, cardiovascular tissues and cells such as those present in and around blood vessels, as well as other tissues present in the epidermis, dermis, as well as nerve receptors, hair follicles, sweat glands, sebaceous glands, apocrine glands, and lymphatic vessels). While application of the electrical stimulation to treatment site, in both the percutaneous and transnasal application, will modulate (e.g., selectively and/or reversibly, the targeted neural- and non-neural tissue of the nervous system structure to inhibit the perception of pain, the electrical stimulation and stimulation device 100 are designed such that no damage is caused to the nervous system structure and/or the surrounding tissue (e.g., the overlying mucosal tissue).

Figure 2A:
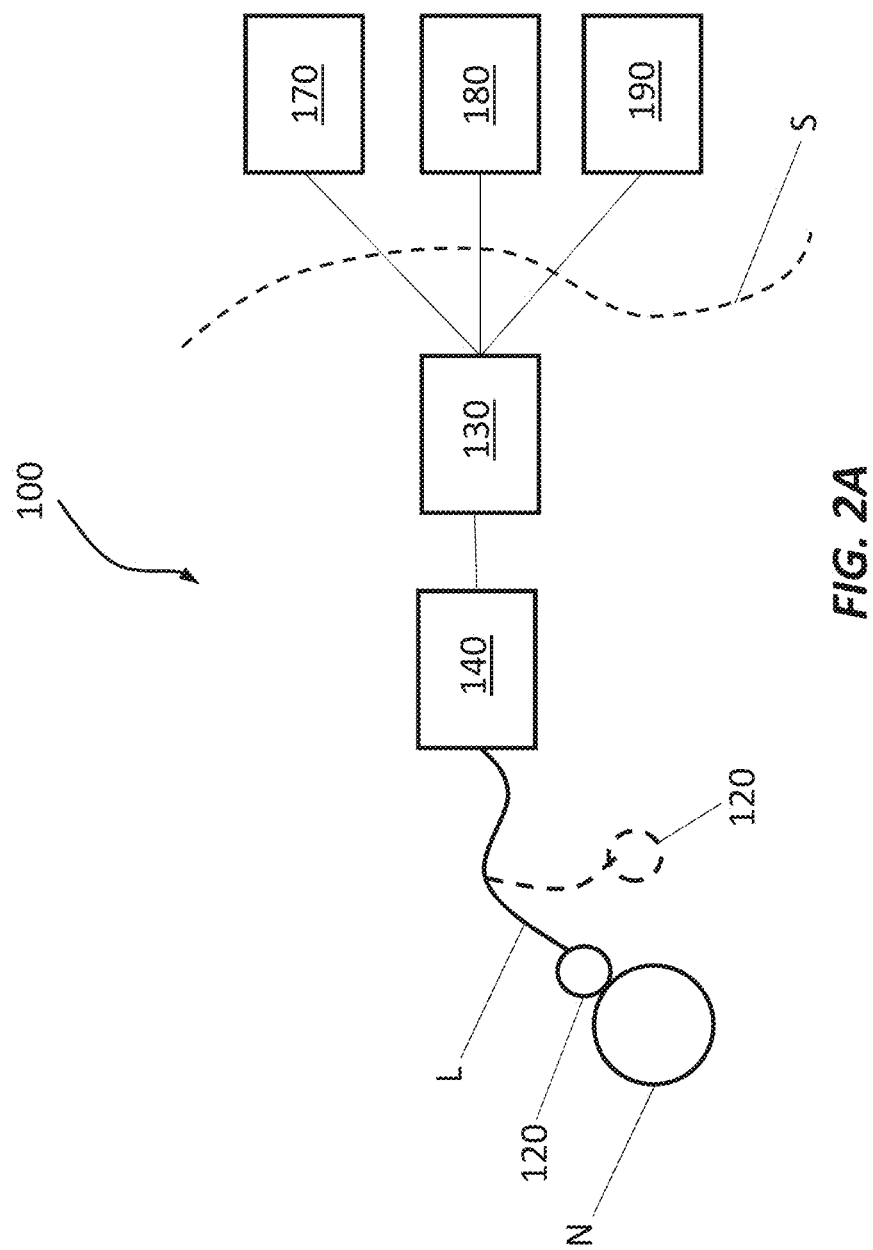
FIG. 2A is a schematic representation of the electrical stimulation device of FIG. 1.
Figure 2B:
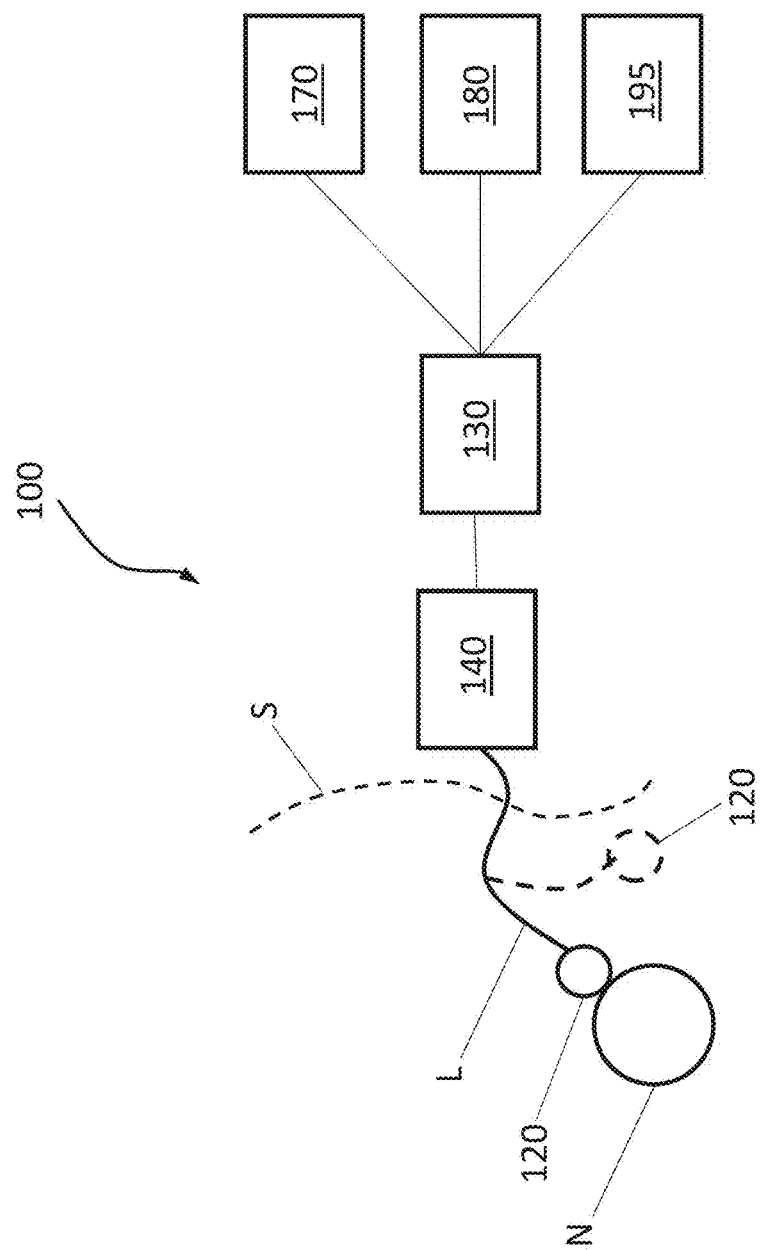
FIG. 2B is a schematic representation of the electrical stimulation device of FIG. 1.

As schematically illustrated in FIG. 1, the stimulation device 100 and electrode 120/leads L may be either reusable or disposable. Desirably, the nervous structure can be modulated via a disposable lead L and electrode 120, and driven by a reusable external stimulator/signal generator 140 and controller 130. It is contemplated that the stimulation device 100, in its entirety, can be sized and configured for implantation within the patient (under the patient's skin (S)) at a location adjacent the targeted nervous structure (N), represented schematically in FIG. 2A. The power source 180, providing electrical energy to the controller 130/signal generator 140 can be positioned internal or external to the patient. It is also contemplated that only the leads/electrode 120 be implanted within the patient and the remaining components, including signal generator 140 and controller 130 are embodied in a handheld device that can be easily manipulated to deliver the therapy, represented schematically in FIG. 2B. It is further contemplated that the stimulation device 100, including signal generator 140, controller 130, and leads/electrodes 120 may be embodied in a larger, non-handheld device designed to remain on a stationary surface or on a cart that can be moved between rooms at a medical clinic, any only the electrodes 120/leads (L) are advanced percutaneously through an opening in the patient's skin or other opening in the patient's body (e.g., via the nasal cavity).

The simulation device 100 can be used to reversibly and/or selectively inhibit pain while preserving other sensory function. Specifically, the electrical stimulation provided by the stimulation device 100 may reversibly and/or selectively modulate nerve signal transmissions through nerve fibers that are responsible for the transmission of pain while preserving nerve signal transmission through nerve fibers responsible for other sensory and motor function, and proprioception.

With respect to the reversibility of the modulated nerve function, the stimulation device 100 can reversibly inhibit pain, for example by inhibiting or blocking nerve signal transmission for a period of about 1 day to about 30 days. Preferably, pain perception is inhibited for a period of about 5 days to about 30 days. For chronic pain, the perception of pain is inhibited for a period of about 90 days to about 356 days. Reversibility of nerve signal transmission and subsequent recovery of function after the appropriate duration of time from treatment is important, particularly for post-surgical acute pain. The parameters of the stimulation waveform can be adjusted to tune the expected duration of pain inhibition and to ensure that pain inhibition does not last for longer than is desired. For example, in patients undergoing knee replacement surgery, it is important for pain perception to return 15-30 days post-surgery because acute pain sensations serve an important protective signal to help patients regulate their physical activity during recovery.

With respect to the selectively of the modulated nerve function, the stimulation device 100 can selectively modulate the neural- and non-neural tissue inhibiting the perception of pain and preserving other sensory and motor function, and proprioception. This produces a scenario in which the electrical neuromodulation treatment is selective to a subset of functions of a nervous structure while preserving other functions of the nervous structure. Pain perception is inhibited, while other sensory and motor function, and proprioception is preserved. For example, the electrical signal disrupts the transmission of pain signals that originate in the periphery from reaching the brain by inhibiting nerve signal transmission through nerve fibers that are responsible for the transmission of pain. This includes direct inhibition of transmission of pain signals in the neurons of the target neural structure, or can be achieved by indirect inhibition of other downstream neurons responsible for transmitting pain signals to the brain, such as neurons of the central nervous system (e.g. spinal cord and the brain).

Preserved sensory function includes, for example, non-painful touch sensation (low-threshold sensory function), vision, audition, gustation, olfaction, and balance. It is also contemplated that the disclosed electrical signal can modulate nerve signal transmission through nerve fibers responsible for the transmission of thermoreception, autonomic activity and visceral function.

Selective modulation of perception of pain is particularly useful in cases where the modulation is desired to be applied to mixed nervous structures, such as peripheral nerves containing motor and sensory axons. For example, in many surgical interventions, it is desirable to modulate pain transmitted via mixed nerves to treat acute surgical pain, while preserving motor and sensory and proprioceptive function of the nerve. Preservation of motor and sensory and proprioceptive function while treating pain is particularly important in cases where physical therapy or other movement of an appendage needs to be performed during recovery from surgery. For example, many post-surgical care programs include steps to help patients avoid muscle atrophy or other stagnation of function after surgical procedures. Preservation of motor control and sensory and proprioceptive function while treating pain can enable and enhance such programs.

As is described in more detail below, one or more parameters of the electrical stimulation can be adjusted to selectively block nerve signal transmission through a select type of nerve fiber and/or through a select region of the nervous structure. Adjustable parameters of the electrical stimulation include, for example, a waveform shape, a waveform frequency, a waveform amplitude, an electrical field strength generated at the electrode 120 (e.g., measured at the electrode or at the treatment site), a waveform DC offset, a waveform duty cycle (e.g., a continuous delivery and/or intermittent delivery through the electrode), a tissue temperature, a cooling mechanism parameter (e.g., a rate of cooling, flow rate of cooling medium, cooling medium pressure, measured temperature at treatment site or a portion of cooling mechanism), and a treatment duration. These parameters are adjustable and controllable by means of the controller 130, the user interface 170, and a cooling mechanism that may be incorporated into the stimulation device 100, as is described in more detail below.

For example, where the targeted nervous structure is a peripheral nerve, e.g., a large peripheral nerve such as those having a diameter greater than about 2.5 mm, the electrical stimulation can inhibit nerve signal transmission through the myelinated Aδ fibers and/or the unmyelinated C fibers in the peripheral nerve, where the electrical stimulation preserves nerve signal transmission through at least one of the Aβ and Aα fibers, and/or motor fibers. It is contemplated that at least one parameter of the electrical stimulation can be adjusted to selectively inhibit the myelinated Aδ fibers and/or the unmyelinated C fibers, while preserving nerve signal transmission through at least one of the Aβ and Aα fibers, and/or motor fibers.

In another example, the electrical stimulation can inhibit nerve signal transmission through the myelinated Aδ fibers and/or the unmyelinated C fibers in the target peripheral nerve, where the electrical stimulation preserves nerve signal transmission through at least one of the Aβ and Aα fibers, and/or motor fibers in a neighboring nerve or neighboring nerve fascicle. By selectively blocking the painful sensation while allowing nerve signal transmission through the select nerve fibers of neighboring nerves and/or neighboring nerve fascicles the sharpness of the painful sensation can be reduced preventing other large motor fibers from being affected.

In another example, the targeted nervous structure covered by a layer of mucosal tissue, e.g., the gasserian ganglion, sphenopalatine ganglion (SPG). The electrical stimulation can be delivered through the mucosal tissue to modulate nerve single transmission through a particular type of nerve fibers of the underlying nervous structure and adjacent non-neural tissue. Types of nerve fibers including, for example, parasympathetic nerve fibers, sympathetic nerve fibers, the sensory nerve fibers). For example, where the targeted nervous structure includes the sphenopalatine ganglion (SPG), the electrical stimulation selectively inhibits nerve signal transmission through the parasympathetic nerve fibers comprising the SPG, the sympathetic nerve fibers comprising the SPG, and/or the sensory nerve fibers comprising the SPG. It is contemplated that this nerve signal transmission can be inhibited while also selectively preserving function of at least one of the non-selected type of nerve fiber (e.g., parasympathetic, sympathetic, and sensory nerve fibers comprising the SPG).

It is further contemplated that at least one parameter of the electrical stimulation can be adjusted to differentially inhibit function of the myelinated Aδ fibers such that the myelinated Aδ fibers have a larger percentage of fibers inhibited than the unmyelinated C fibers. Nerve signal transmission through myelinated Aδ is typically associated with the sensation of fast, sharp/stabbing pain, while nerve signal transmission through unmyelinated C fibers is typically associated with the sensation of dull/aching pain. Accordingly, the electrical stimulation can be adjusted to differentially inhibit the function of nerve fibers responsible for the sensation of sharp pain, such that those fibers have a larger percentage of fibers inhibited than nerve fibers responsible for the sensation of dull/aching pain Similarly, it is further contemplated that at least one parameter of the electrical stimulation can be adjusted to differentially inhibit function of the unmyelinated C fibers, such that the unmyelinated C fibers have a larger percentage of fibers inhibited than the myelinated Aδ fibers. That is, the electrical stimulation can be adjusted to differentially inhibit the function of nerve fibers responsible for a sensation of dull/aching pain, such that those fibers have a larger percentage of fibers inhibited than nerve fibers responsible for a sensation of fast, sharp/stabbing pain.

In another example, where the targeted nervous structure covered by a layer of mucosal tissue, such as the gasserian ganglion or sphenopalatine ganglion (SPG), the electrical stimulation can be adjusted to differentially inhibit function of the parasympathetic, sympathetic, and/or sensory nerve fibers of the ganglion. For example, the electrical stimulation delivered to the target site can differentially inhibit the function of the parasympathetic nerve fibers of the SPG, where the parasympathetic nerve fibers have a larger percentage of fibers inhibited than non-parasympathetic nerve fibers and the non-neural tissue. Likewise, the electrical stimulation delivered to the target site can differentially inhibit the function of the sympathetic nerve fibers of the SPG, where the sympathetic nerve fibers have a larger percentage of fibers inhibited than non-sympathetic fibers and the non-neural tissue. Similarly, the electrical stimulation delivered to the treatment site can differentially inhibit function of the sensory nerve fibers of the SPG, where the sensory nerve fibers have a larger percentage of fibers inhibited that the parasympathetic, sympathetic and the non-neural tissue.

An additional mechanism of inhibition of perception of pain is when the inhibitory effect is downstream or secondary to the treatment site. For example, where the targeted nervous structure is a large peripheral nerve, e.g., a nerve having a diameter greater than about 2.5 mm, the electrical stimulation can modulate activity or function of neural or non-neural tissues which results in activation of a biochemical signaling cascade which causes a decrease in activation of spinal or cortical neurons representing pain (for example, via modulation of synaptic signaling), while nerve signal transmission through central nervous system and peripheral nervous system neurons involved in detection, transmission, processing, and generation of non-painful touch, motor control, and proprioception are preserved. It is contemplated in this case, that at least one parameter of the electrical stimulation can be adjusted to selectively inhibit downstream or secondary effects of pain originating from Aδ fibers and/or originating from the unmyelinated C fibers, while the function of central nervous system and peripheral nervous system neurons involved in detection, transmission, processing, and generation of non-painful touch, motor control, and proprioception are preserved.

It is further contemplated in this case that at least one parameter of the electrical stimulation can be adjusted to differentially inhibit downstream or secondary effects of pain originating from myelinated Aδ fibers such that the downstream or secondary effects from myelinated Aδ fibers are inhibited to a greater extent than the downstream or secondary effects from unmyelinated C fibers. Similarly, it is further contemplated in this case that at least one parameter of the electrical stimulation can be adjusted to differentially inhibit downstream or secondary effects of pain originating from unmyelinated C fibers, such that the downstream or secondary effects from unmyelinated C fibers are inhibited to a greater extent than the downstream or secondary effects from myelinated Aδ fibers.

Example Electrical Stimulation

As described above, the electrode 120 provides an electrical signal to the treatment site for selectively modulating the neural- and non-neural tissue inhibiting the perception of pain and preserving other sensory and motor function, and proprioception. The electrical signal disrupts the transmission of pain signals by modulating both neural and non-neural tissue. Various parameters of the electrical signal can be adjusted, as outlined below, to modulate function via the nervous structure, including, for example, a stimulation-pulsed waveform shape (also referred to herein simply as "waveform shape"), a stimulation-pulsed frequency (also referred to herein simply as "frequency"), a stimulation-pulsed amplitude (also referred to herein simply as "amplitude"), an electrical field strength generated at the electrode 120, a stimulation-pulsed waveform DC offset, a waveform duty cycle (e.g., a continuous delivery, and/or intermittent delivery through the electrode), a tissue temperature, a cooling mechanism parameter, and a treatment duration. It is contemplated that some parameters may be adjusted individually to produced a desired effect, while others are adjusted in combination with some interdependence on each parameters adjustment in an effort to produce the desired effect. As described above, and in more detail below, various parameters and/or combinations of parameters of the electrical signal are adjusted to selectively and reversibly modulate nerve signal transmission through a select type of nerve fiber and/or through a select region of the nervous structure.

To facilitate the selective and/or reversible inhibition of nervous system activities (e.g., to block acute pain), the stimulation device and system is configured, in some embodiments, to apply a high frequency stimulation directly to the nerve and/or to nearby tissue to invoke sufficient pain inhibition response by the nervous system. The high-frequency stimulation may be applied in pulses over the course of a single treatment/application and in a manner so as to avoid damaging nearby tissue and nerve tissue. It has been observed that a high-frequency stimulation applied at 500 kHz in a series of 20 millisecond pulse at up to 100 V for a few minutes (and up to a temperature of 42° C.) can be applied to invoke a sufficient pain inhibition response that can selectively disrupt sensation of acute pain but not affect other neurological function such as motor control. It has also been observed that the same high-frequency stimulation can be applied to invoke a reversible pain inhibition response in that pain is blocked for a clinically relevant duration that can last from 1 day to 30 days. Without wishing to be bound to a particular theory, it is hypothesized that the selective and reversible effect can be attributed to the particularly high voltage-field that is applied to the tissue while not causing thermal damage at the treatment site, particularly to the nerves.

Figure 7A:
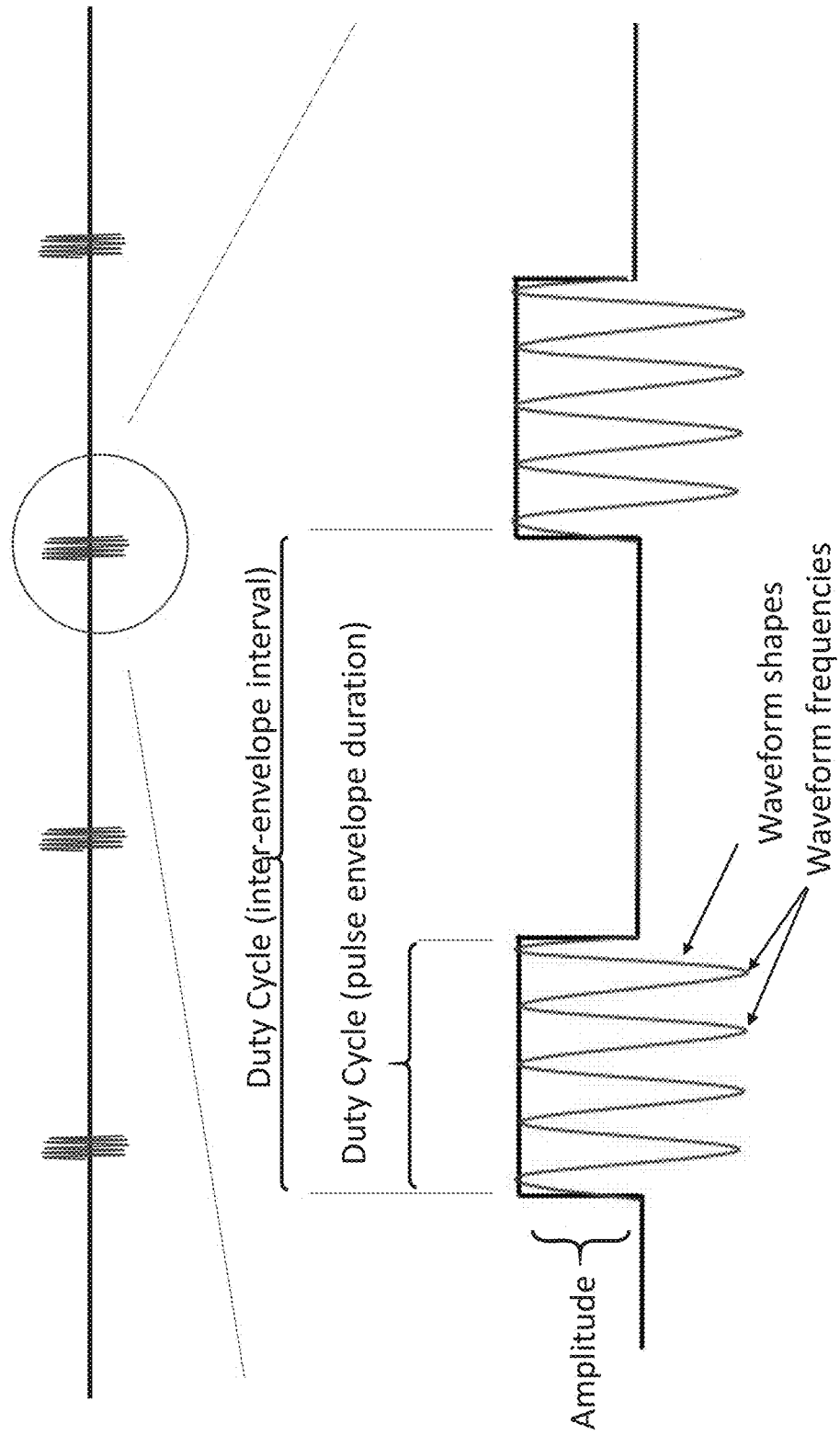
FIG. 7A is an example electrical stimulation, and corresponding control parameters, that can be applied to the nerve and/or nearby tissue to selectively and/or reversibly inhibit nervous system activities.

FIG. 7A shows an example electrical stimulation, and corresponding control parameters, that can be applied to the nerve and/or nearby tissue to selectively and/or reversibly inhibit nervous system activities, in accordance with an illustrative embodiment. As shown in FIG. 7A, the electrical stimulation can be defined via control parameters such as amplitude, pulse duty cycle (e.g., comprising a pulse envelope duration and an inter-envelope interval), stimulation waveform shape, and waveform frequency. In addition to a stimulation frequency of 500 kHz, other stimulation frequency ranges can be applied. In some embodiments, the stimulation device and system is configured to apply an electrical stimulation having a stimulation frequency selected from the group consisting of about 100 kHz, about 150 kHz, about 200 kHz, about 250 kHz, about 300 kHz, about 350 kHz, about 400 kHz, about 450 kHz, about 500 kHz, about 550 kHz, about 600 kHz, about 650 kHz, about 700 kHz, about 800 kHz, about 850 kHz, about 900 kHz, about 950 kHz, and about 1 MHz. Application of an electrical stimulation having a pulse duty cycle can allow for a higher voltage or current amplitude to be outputted and/or higher frequency (to allow for higher voltage field to be generated at the treatment site) while not causing thermal damage at the tissue. Application of an electrical stimulation having a non-sinusoidal waveform can be used to adjust the energy density that is applied in a given electrical stimulation and/or also allowing for higher electrical field to be applied.

Figure 7G:
Figure 7H:
Figure 7I:
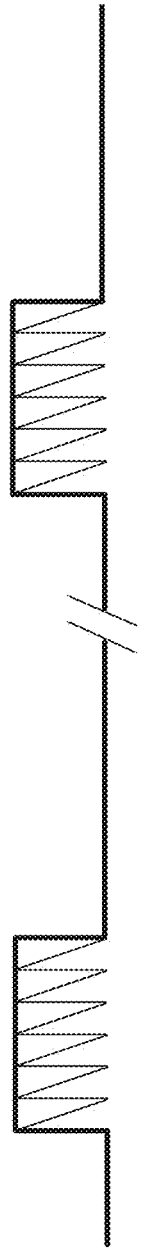
Figure 7J:
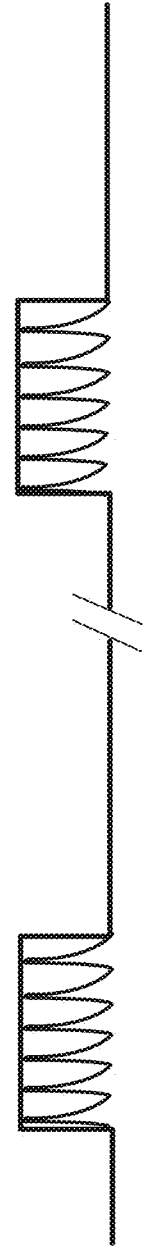
Figure 8:
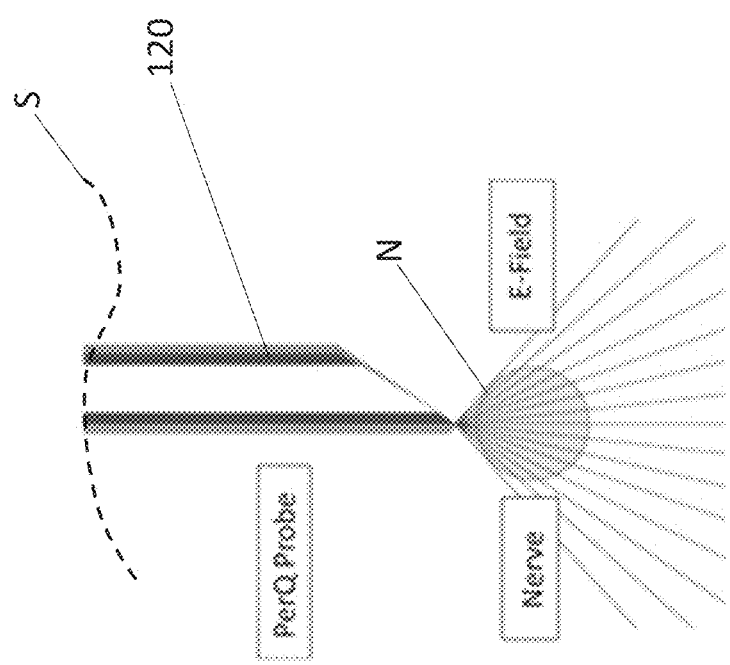
FIG. 8 is a schematic representation of positioning an electrode percutaneously and delivering and electrical stimulation to a target nervous structure.

FIGS. 7B, 7C, 7D, 7E, 7F, 7G, 7H, 7I, 7J, 7K, 7L, 7M, 7N, 7O, and 7P each shows a waveform shape for an electrical stimulation, in accordance with an illustrative embodiment. As shown in FIGS. 7B-7F, in some embodiments, the stimulation waveform is a sinusoidal waveform (FIGS. 7B, 7G), a triangular waveform (FIG. 7C), a square or rectangular waveform (FIG. 7D), a triangular saw-tooth waveform (FIG. 7E), or a complex waveform (FIG. 7F).

In some embodiments, the frequency of a given pulse is varied (e.g., as a chirp, as shown in FIGS. 7K, 7L, and 7M). In some embodiments, the amplitude envelope of the electrical stimulation is varied for a given pulse (FIGS. 7K and 7L).

In some embodiments, the electrical stimulation is a voltage controlled output. In some embodiments, the electrical stimulation is a current controlled output. In some embodiments, the electrical stimulation is a power controlled output.

In some embodiments, the stimulation waveform shape comprises a continuous charge-balanced sinusoid (see, e.g., FIGS. 7B-7F, 7K, 7L, 7M, 7N, and 7P), or an additive combination of sinusoids (e.g., as a sine function (see FIGS. 7N, 7O, and 7P).

The illustrated waveforms are merely illustrative. It is contemplated that other type of waveforms shapes can be generated such as impulses or other shapes. In some embodiments, the stimulation waveform comprises a single pulse having a duration of 1 µs to 10 µs.

Other stimulation pulse control parameters can be controlled, e.g., in a feedback mechanisms, such as electric field strength at the electrode, DC offset, tissue temperature, cooling mechanism parameter, and treatment duration. In some embodiments, the stimulation device and system is configured to control the electrical stimulation based on an observed or measured temporal and/or spatial derivatives of voltage, current, power, and temperature (e.g., the rate-of-change of temperature over time). In some embodiments, two or more of current-controlled stimulation, voltage-controlled stimulation, power-controlled stimulation, and temperature-controlled stimulation can be executed in combination to deliver to the targeted neural- and non-neural tissue of the nervous structure. The parameters of amplitude, waveform shape, frequency, DC offset, duty cycle and duration can be tuned for such current-controlled stimulation, voltage-controlled stimulation, power-controlled stimulation, and/or temperature-controlled stimulation, or a combination thereof.

Indeed, the stimulation parameters can be optimized to selectively inhibit perception of pain while preserving nerve activity responsible for motor activity, low-threshold sensory function, and proprioception. For example, the stimulation parameters can be optimized to attenuate or abolish activity in myelinated Aδ and unmyelinated C fibers while preserving (e.g., without attenuating) nerve activity in the nerve fibers responsible for motor activity, low-threshold sensory function, or proprioception.

The amplitude and other parameters of the stimulation waveform may be tuned to preferentially or optimally modulate activity within a desired region of a nerve (e.g., affect specific regions of a nerve vs. affecting the complete nerve cross-section), as will be described in more detail below. The stimulation waveform can also include parameter changes which influence and reduce onset response (e.g., a pulsing sensation at the nervous structure, motor response in a muscle adjacent the target nerve such as muscle spasm or twitching) and activation of nerve tissue at the onset of stimulation at either the beginning of the continuous waveform or at the onset of each burst of stimulation during intermittent stimulation. The parameters of the stimulation waveform may also be tuned to control the duration and time-course of pain inhibition that will be achieved after the treatment and to ensure that adequate pain inhibition is achieved with a single treatment.

The parameters of the stimulation waveform may be adjusted to enable treatment of larger nerves (for example, with a diameter greater than about 2.5 mm) and larger nervous structures or nervous structures with different shapes, sizes, and neural and non-neural tissue composition, for example by increasing the amplitude or adjusting other parameters of the stimulation waveform which result in an increase in the spatial size and shape electric field. Some nervous structures, such as the spinal cord and some ganglia or plexuses, are large by nature and treatment of these large structures is enabled by adjustment of the waveform parameters.

The parameters of the stimulation waveform may also be adjusted to enable non-damaging treatment and inhibition of pain. Hardware and software may also be included to control the amount of DC current delivered concurrently with the waveform. The controller 130 may include, for example, a current controller or a voltage controller for adjusting the amount of DC current or voltage delivered concurrently with the electrical signal.

The present device and method can be used to selectively and reversibly modulate nerve signal transmission, for example by inhibiting or blocking nerve signal transmission, to inhibit the perception of pain for a period of about 1 day to about 30 days. Preferably, pain perception is inhibited for a period of about 5 days to about 30 days. Reversibility of nerve signal transmission and subsequent recovery of function after the appropriate duration of time from treatment is important, particularly for post-surgical acute pain. The parameters of the stimulation waveform can be adjusted to tune the expected duration of pain inhibition and to ensure that pain inhibition does not last for longer than is desired. In one example, the duty cycle, pulse amplitude, and treatment duration (see e.g., FIGS. 10 and 11) can be adjusted to produce a desired reversibility of the nerve signal inhibition (see e.g., FIGS. 10 and 11). In another example, controlling the temperature at the treatment site can be used to produce a desired selectivity of the modulation of nerve signal transmission (see e.g., FIGS. 10 and 11).

As mentioned above, the device and method of the present invention, including the parameters of the waveform and adjustment thereof, can selectively inhibit acute pain (such as post-surgical pain) for a period of days-to-weeks post-procedure. However, it is also to be understood that the device and method of the present invention, including the parameters of the waveform and adjustment thereof, can also be used to provide therapeutic treatment for chronic pain conditions. The therapeutic treatment for chronic pain may include ongoing preventative delivery of signals, or abortive, on-demand delivery when episodes of chronic pain are experienced. This may be performed via percutaneous, partially-implanted, and implanted approaches.

Compared to other methods of modulating activity of a nervous structure using an electrical signal, the system and method of the present disclosure is able to provide selective and reversible pain relief for periods of days to weeks with a single treatment/application of the electrical signal. Other treatment modalities require repeated treatments over a period of days to provide any meaningful and lasting pain relief, particularly with respect to the treatment of large nerves. For example, pulsed radiofrequency, frequently used to treat pain in small nerves, utilizes intermittent pulses of a 45V radiofrequency signal to stimulate the target nerve. Pulsing is used in this case to avoid temperatures at the treatment site that would damage or destroy the nerve tissue. In contrast, the stimulation parameters of the present disclosure allow for the application of a high voltage, high frequency waveform that does not have the temperature limitations associated with a pulsed RF signal. Adjustment of the parameters of the stimulation waveform enables control of the application of the electric signal to ensure that adequate pain inhibition is achieved with a single application while avoiding damage to the tissue.

For example, a system can be configured to deliver the electrical signal (also referred to herein as "electrical stimulation") to the treatment site with a frequency range between of about 100 kHz to about 1 MHz, between about 200 kHz to about 800 kHz, between about 400 kHz to about 600 kHz, and between about 450 kHz to about 550 kHz. In an example system, the electrical stimulation delivered to the treatment site is at least 500 kHz. The electrical signal delivered to the treatment site has an amplitude range 5 mA (peak-to-center, corresponding to 10 mA peak-to-peak) and ≤1.25 A (peak-to-center, corresponding to 2.5 A peak-to-peak). In an example system, the electrical signal has an amplitude ranging between 50 mA and 500 mA, 500 mA and 1 A, 1 A and 1.5 A, 1.5 A and 2 A, or 2 A and 2.5 A. In an example system where the electrical simulation is delivered transmucosally, the electrical signal has an amplitude ranging between about 10 mA and about 5,000 mA (peak-to-peak). The electrical signal delivered to the treatment site has an amplitude range ≥10 V and ≤500 V (peak-to-center, corresponding to 20-1000 V peak-to-peak). In an example system, the electrical signal has an amplitude ranging between 10 V and 1,000 V, 20 V and 100 V, 100 V and 200 V, 200 V and 300 V, 300 V and 400 V, or 400 V and 500 V. In an example system where the electrical simulation is delivered transmucosally, the electrical signal delivered to the treatment site has an amplitude range ≥10 V and ≤1,000 V (peak-to-peak). In an example system, the electrical stimulation delivered to the treatment site has a power ranging between about 0.1 W and about 1,250 W.

The electrical signal delivered to the treatment site can have a sinusoidal shaped waveform, a square shaped waveform, a triangular shaped waveform, a frequency-modulated waveform, an impulse (e.g., an amplitude-modulated waveform, or an impulse-shaped waveform), and/or additive combinations thereof. An example of a frequency-modulated waveform is a chirp. An example of an amplitude-modulated waveform is a wavelet. In another example system, the electrical signal delivered to the treatment site has an arbitrary waveform. In another example system the electrical signal can have a combination of the waveforms mentioned previously. Repeated delivery of the waveform is implied in which a waveform shape is delivered in repeated fashion at a specified repetition frequency. The waveform of the electrical signal can be delivered continuously or intermittently. Continuous delivery implies that the waveform is delivered at a specified waveform frequency continuously, without breaks. Intermittent delivery implies that the waveform is delivered at a specified waveform frequency during envelopes of time that are separated by breaks during which no stimulation is delivered. For continuous delivery, the duty cycle is 100% (for example, via chirp function). For intermittent delivery, the duty cycle ranges from about 0.1% to about 99%, preferably 0.5% to 25%. The term duty cycle refers to a period that the pulse is on having multiple oscillations with a predefined frequency. For intermittent delivery, the electrical signal has an inter-envelope width of about 1 ms to about 999 ms, preferably 70-999 ms, where the inter-envelope width is defined as the duration of time between then end of an envelope and the start of the next envelope. In one example, the electrical signal has a 30 ms pulse width delivered at 10 kHz.

During an example treatment, the electrical signal is delivered for a treatment duration of ≤30 minutes, preferentially ≤15 minutes. In an example system, the electrical signal is delivered for treatment duration of ≤1 minute, 1 minute to 5 minutes, 5 minutes to 10 minutes, 10 minutes to 15 minutes, 15 minutes to 20 minutes, 20 minutes to 25 minutes, or 25 minutes to 30 minutes.

As described below, the controller 130 is adjustable to apply the electrical stimulation while maintaining the tissue temperature between about 5° C. and about 60° C. That is, the electrical signal can have a tissue temperature that has an amplitude between about 5° C. and about 60° C.

The electrical signal delivered to the treatment site may be current controlled, voltage controlled, power controlled and/or temperature controlled. The electrical signal comprises a continuous charge-balanced waveform or impulse, or additive combination thereof. Alternatively, the electrical signal comprises a not charged-balanced waveform or impulse, or additive combination thereof.

The strength of the electrical field generated at the target site is greater than 10 kV/m. The electrical stimulation delivered to the treatment site generates or induces an electrical field strength at the target site and/or the one or more electrodes between about 20 kV/m and about 2,000 kV/m. The electrical field generated at the target site ranges between 20 kV/m to 2,000 kV/m at its temporal peak, 25 kV/m to 500 kV/m, or 50 kV/m to 400 kV/m. In a transmucosal application, the electrical stimulation generates or induces an electrical field strength at the target site and/or the electrode preferably between about 20 V/m and about 1,000,000 V/m. The strength of the electrical field varies as a function of distance from the electrode, shape of the electrode, and other factors such as the conductivity of the different tissues near the electrode. Tuning of waveform parameters of the stimulation waveform enables control of the spatiotemporal electrical field within the tissue and at the interface of the electrode with the tissue. Tuning of the waveform parameters of the stimulation waveform also enables control of the spatiotemporal thermal field within the tissue and at the interface of the electrode with the tissue. The spatiotemporal variations and levels of the electrical field and the thermal field are important factors in producing the desired selective, reversible inhibition of pain in the target neural structures. Additionally, a cooling mechanism, as will be discussed in detail below, implemented in concert with the waveform and other aspects of the stimulation such as the electrode, enables control and reduction of the spatiotemporal thermal field independent or semi-independent from the electrical field. Separation of these two important variables ultimately enables delivery of a selective, reversible, and tunable treatment that is nondamaging to the neural tissue.

In addition to selectively treating different fiber types, the parameters of the electrical stimulation and the induced electric field and the parameters of the electrical waveform can also be adjusted to preferentially modulate nerve signal transmission within a desired region of the nervous structure, where the desired region of the nervous structure is a portion of the nervous structure less than its complete cross-section.

The electrical stimulation can also be adjusted to reduce onset response (e.g., a pulsing sensation at the nervous structure, motor response in a muscle adjacent the target nerve, such as a muscle spasm or twitching, and activation of the nervous structure during delivery of the electrical stimulation to the nervous structure.

Example Cooling Mechanism

It is also contemplated that the stimulation device 100 can include a cooling mechanism to prevent damage to the patient's tissue during delivery of the electrical stimulation. The cooling mechanism can be integral with the electrode 120 and/or a separate component from the electrode 120 that can is coupled to the electrode or positioned at the treatment site separate from the electrode 120. The cooling mechanism can be controlled by the controller 130 or include a separate controller for directing its operation. The cooling mechanism is used to provide a cooling effect at the contact surface of the stimulation device 100 and/or contact surface of the electrode 120 and/or within the tissue near the treatment site.

It is appreciated by those skilled in the art that delivery of electrical stimulation waveforms to tissue can result in heating of the tissue adjacent the delivery electrode 120. When heating of the tissue is excessive, thermal damage to the tissue can be created. One objective of the present invention is to produce selective and reversible inhibition of pain perception while preserving other sensory and motor function, and proprioception. Thermal lesions of tissue have been deliberately used to ablate or inhibit transmission of nerve action potentials, however, these approaches do not preserve sensory and motor function and proprioception. Additionally, cooling of tissue has been used with thermal ablations, for example with cooled radiofrequency ablations, to enable an increase in power dissipation in the tissue, allowing for an increase in the power of an RF waveform and creation of a larger thermal lesion. However, these cooled RF approaches aim to raise the tissue temperature to at least 60-90° C. in order to create a thermal lesion in the tissue. In contrast, the present disclosure contemplates use of a cooling mechanism that will preserve tissue below thermal damage levels while enabling delivery of an electrical signal that can result in inhibition of pain while preserving sensory, motor and proprioceptive function in the nervous structure.

The cooling mechanism creates a cooling effect that prevents damage to the patient's tissue when the electrical stimulation is delivered by preserving temperatures of the patient's tissue below a destructive tissue temperature, e.g., below temperatures likely to cause thermal damage to the tissue (for example avoiding temperatures that rise above 42-45° C. for a period of multiple seconds). The cooling mechanism maintains the temperature of the contact surface of the stimulation device 100 and/or electrode 120 below a destructive tissue temperature in response to feedback information received from the electrode 120 and/or input from the patient and/or operator. The feedback information includes the measured temperature data received from a temperature sensor 210 coupled to the stimulation device 100. The temperature sensor 210 can measure the temperature of the contact surface of the electrode 120 and/or the temperature of the patient's tissue adjacent the contact surface of the electrode 120. The temperature sensor 210 is electrically coupled to the controller 130 and provides feedback information regarding the measured temperature. As described below, in response to the temperature feedback information, operation of the cooling mechanism and/or parameters of the electrical stimulation can be adjusted to control the temperature at the contact surface of the electrode 120, thereby reducing the temperature of the adjacent patient tissue.

In one example, the cooling mechanism may comprise a pump which circulates a cooling medium such as a gas or pressurized fluid (e.g., carbon dioxide, nitrogen, water, propylene glycol, ethylene glycol, salt water, or mixtures thereof) through the electrode 120 via the conduits 160 provided in the leads (L) (see FIGS. 3A-3E). The circulated gas/fluid serves to remove heat from the electrode 120, tissue of the treatment site and the neighboring tissues. This gas/fluid may be delivered at room temperature or may be cooled below room temperature by use of an incorporated gas/fluid cooling unit or by use of ice or other cooling mechanisms. The cooling of the gas/fluid may be performed before treatment and during treatment. A thermally insulating coating or sheath may also be incorporated around the leads (L) to prevent heating of the cooling medium by heat transfer to the ambient environment.

In another example, the cooling mechanism includes a heat transfer material provided in contact with the tissue of the treatment site and/or the electrode 120. The heat transfer material can be disposed within the electrode 120/leads (L), on an exterior surface of the electrode 120, and/or on an introducer. The heat transfer material acts as a heat sink removing heat from the electrode 120, the tissue of the treatment site and the neighboring tissue. The heat transfer material can include a material with high thermal conductivity (e.g., metal such as aluminum, ceramic material, conductive polymer), a material with a high capability to store heat (e.g., a good thermal mass, such as materials with a high specific heat capacity, high heat capacity per unit mass, high volumetric heat capacity, and/or high heat capacity per unit of volume), and/or one or more Peltier circuits, or combination of these. The heat transfer material can also include a phase change material that can change phase at a temperature between about 40° C. and 100° C. An example phase change material includes a paraffin wax provided in a pathway that extends from the electrode 120/treatment site to the ambient air. Heat exchange between the paraffin wax and the ambient air serves to remove heat from the electrode 120/treatment site and the neighboring tissues. Additional exemplary cooling mechanisms are described in U.S. Application No. 62/403,876, filed Oct. 4, 2016, entitled "Cooled RF Probes," incorporated herein by reference.

In addition to preventing damage to tissue, the cooling mechanism enables selective inhibition of pain. For example, non-selective inhibition of pain, where motor or non-painful sensory or proprioceptive function is also inhibited, can be observed when temperatures are not preserved below a desired threshold (such as 42-45° C. for a period of multiple seconds). Preservation of the target tissue below such a thermal threshold by use of a cooling mechanism enables selective inhibition of pain without modulating or inhibiting other functions of the nervous structure. Thus, the temperature of the electrode and the tissue is an important parameter that can be tuned by means of the cooling mechanism to enable selectivity of inhibition of pain.

Use of the cooling mechanism also enables treatment of nervous structures of various shapes, sizes, and compositions. For example, the size of the spatial electric field generated by the electrical waveform in the tissue may need to be increased in order to encompass larger nervous structures such as large peripheral nerves, cranial nerves, ganglia, autonomic nerves, portions of the spinal cord, and plexuses. One method for increasing the size of the spatial electric field is to increase the amplitude of the electrical waveform. Use of the cooling mechanism enables an electrical waveform to be delivered with higher amplitude while maintaining the tissue at thermal levels that avoid thermal damage. For example, when peripheral nerves with a diameter greater than 2.5 mm are treated by the stimulation device 100, use of the cooling mechanism enables the electrical waveform parameters, including the amplitude, to be adjusted to levels high enough to treat the larger nerve target without producing thermal damage to the nervous structure. In another example, the nervous structure, such as the spinal cord or ganglia (e.g., gasserian ganglion, sphenopalatine ganglion (SPG)), may be composed of and surrounded by various tissues with different thermal and electrical conductivities. In this case, the cooling mechanism enables delivery of a therapeutic waveform which produces the desired selective and reversible inhibition of pain within a desired region of the nervous structure while preventing thermal damage at sites (including the nervous structure and its surrounding tissue) which are more prone to heating.

Furthermore, use of the cooling mechanism enables tuning of the spatial field of tissue treated by the electrical signal to allow modulation of nerve signal transmission within a desired region of the nervous structure, where the desired region of the nervous structure is a portion of the nervous structure less than its complete cross-section. Cooling may be applied to tissues near the electrode 120 or to tissues neighboring the target treatment site to prevent tissue temperatures from exceeding a desired threshold level. For example, stimulation delivered via an electrode without cooling may produce a thermal field within the tissue which would be thermally damaging at some locations in the tissue. Use and placement of the cooling mechanism at locations which are anticipated to produce thermal damage to tissue enables non-damaging treatment and tuning of the spatial field of tissue treated by the electrical signal. In another example, thermal impulses in the tissue may be produced during short (e.g. less than a second) periods of time. The cooling mechanism enables reduction of these thermal impulses below a threshold level at specific locations in the tissue to enable tuning of the spatial field of tissue treated by the electrical signal. In another example, cooling and electrical waveform parameters may be adjusted concurrently to allow for treatment of a nervous structure (either treatment of a portion of the nervous structure less than its complete cross section or treatment of an entire cross section of the nervous structure) without producing thermal damage.

Example Electrode

FIGS. 3A-3G provide schematic representations of various example electrodes 120 for delivering electrical stimulation to the target nervous structure. The electrodes 120 in FIGS. 3A-3E and 3G are in the form of a percutaneous electrode(s) configured for placement nearby (e.g., the electrode is within about 1 cm, within about 5, or less than 2 mm of the nervous system structure, without contacting the nervous system structure), around, and/or contacting a target nerve. The example electrodes are illustrated in FIGS. 3A-3E and 3G in a side perspective view. Exemplary percutaneous electrodes are also described in U.S. patent application Ser. No. 15/501,450, filed Feb. 3, 2017, titled "Selective Nerve Fiber Block Method and System," incorporated herein by reference.

Figure 3B:
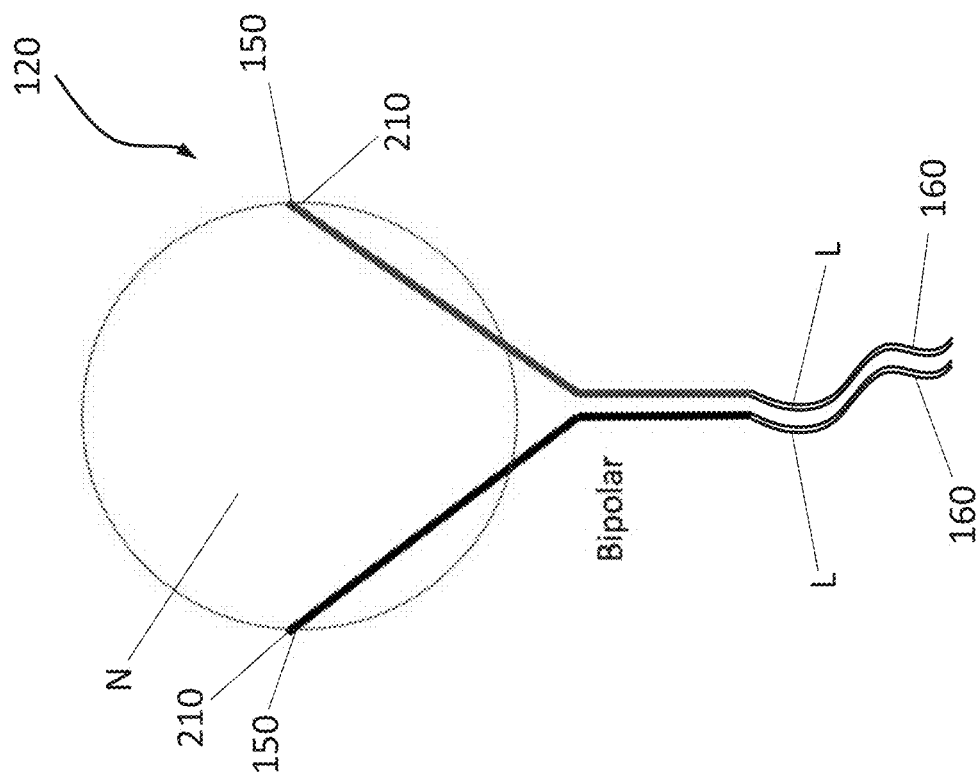
FIGS. 3A-3G are schematic representations of example percutaneous electrodes.
Figure 3A:
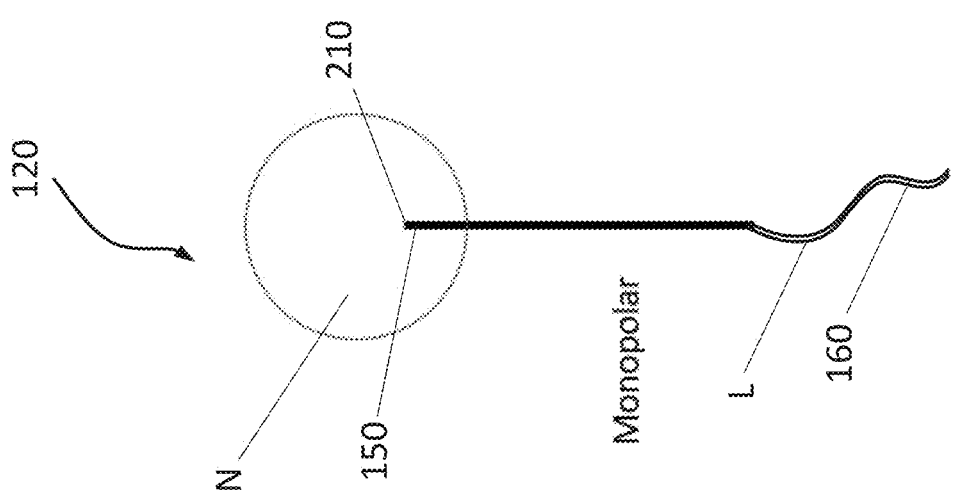
Figure 3E:
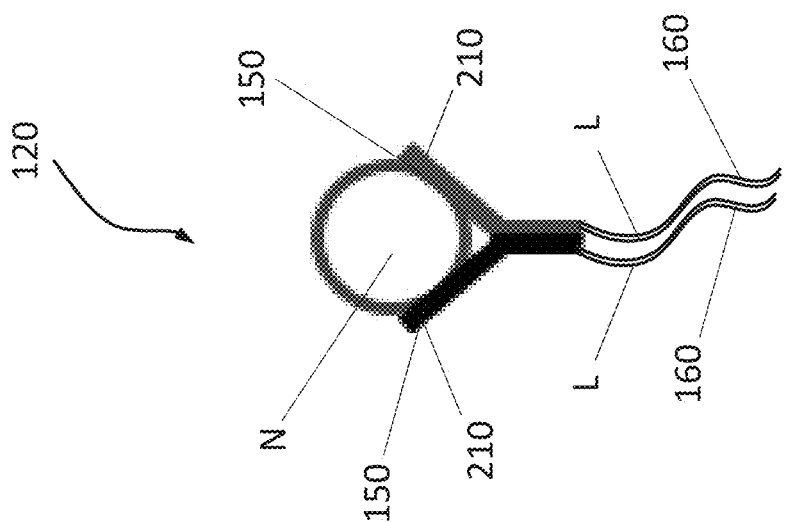
Figure 3D:
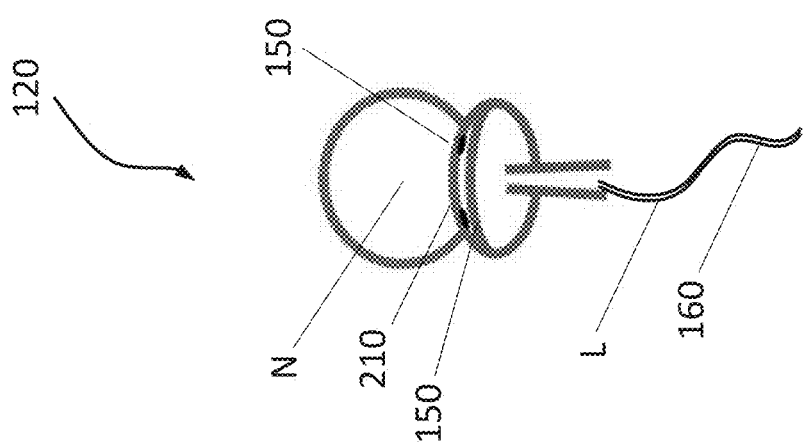
Figure 3C:
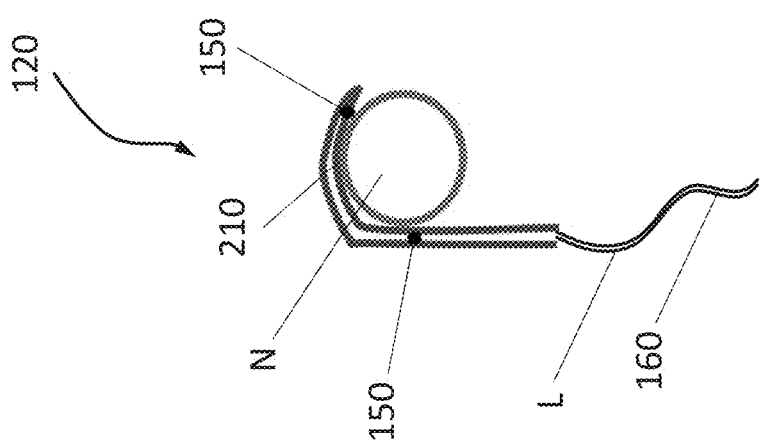

Each electrode used in a bipolar or multi-polar fashion has at least one anode region and at least one cathode region placed nearby/contacting the target nerve "N". The monopolar electrode 120 illustrated in FIG. 3A can include a cathode located nearby a nerve, and a return electrode (e.g., anode) positioned some distance away (e.g., in the form of a patch electrode on the surface of the skin). Bipolar and multipolar electrode configurations, as illustrated in FIG. 3B, have at least one cathode and one anode in the vicinity of the nerve. The electrode shape and size, and inter-electrode spacing are specific to contouring the electrical field and thermal fields surrounding and penetrating the nerve, to enable selective and reversible modulation of the target nervous structure. FIG. 3C provides another example percutaneous electrode 120 having a hook or J-shape. As illustrated in FIG. 3C, the electrode 120 is sized and configured to conform to the target neural structure laterally within the convex portion of the hook shape such that, once positioned, the neural structure is retained near the electrode 120 and contact between the neural structure and the electrode contacts 150 is ensured. As illustrated in FIG. 3C, the electrode 120 includes two electrical contacts, a first contact 150 provided on the curved hook/J-shaped distal tip of the electrode 120 and a second contact 150 provided elongated main body portion of the electrode 120. Such an electrode may be designed to be inserted via an introducer and in such a way that the hook/J-shaped portion of the end of the electrode is bent within the introducer providing a reduced profile. Upon exit from the introducer, the bent portion of the electrode 120 expands and curves around the surface of the nervous structure. FIG. 3D illustrates an example electrode 120 where the electrode tip defines a generally hemi-spherical shape and provides a generally uniform nerve contacting surface. The electrode may include an expandable conductive surface that when inserted through a small-diameter introducer is confined/not expanding and provides a reduced profile. Upon exit from the introducer, the expandable conductive surface is expands to conform around the surface (or a portion of the surface) of the target neural structure. FIG. 3E illustrates an example electrode 120 having a V- or U-shape. As illustrated in FIG. 3E, the electrode 120 is sized and configured to be placed such that the target nervous structure is positioned laterally within the convex portion of the V/U-shape. Once located at the treatment site, the nervous structure is positioned within the electrode 120 convex portion of the electrode to maintain contact with the contacts 150 on longitudinally opposite sides of the nervous structure.

Figure 3F:
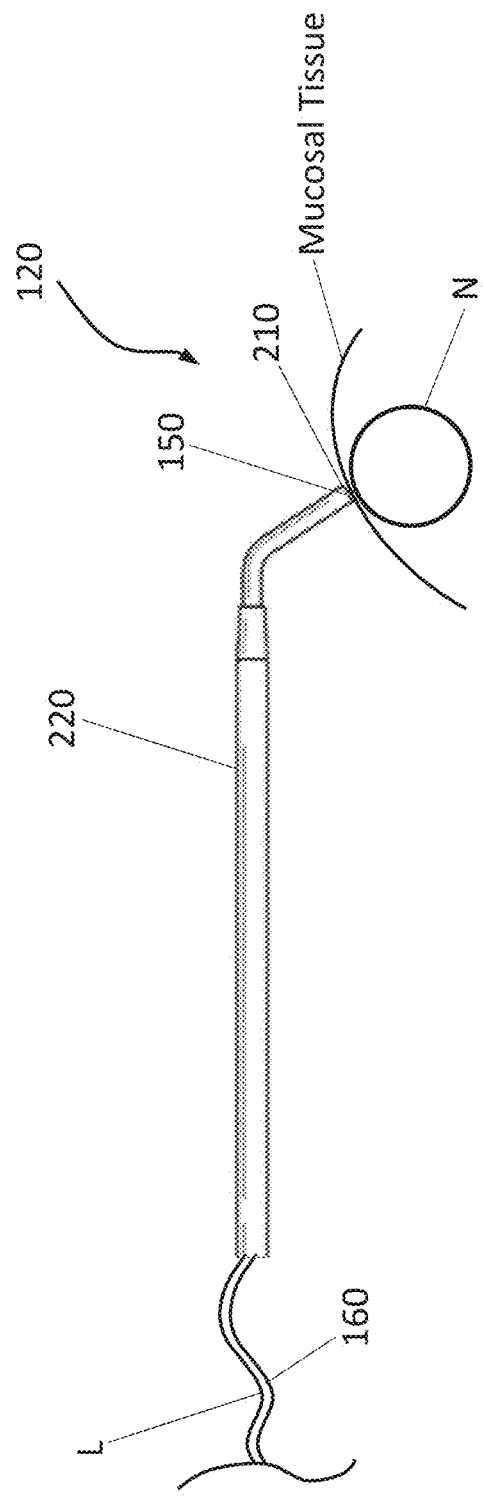
Figure 3G:
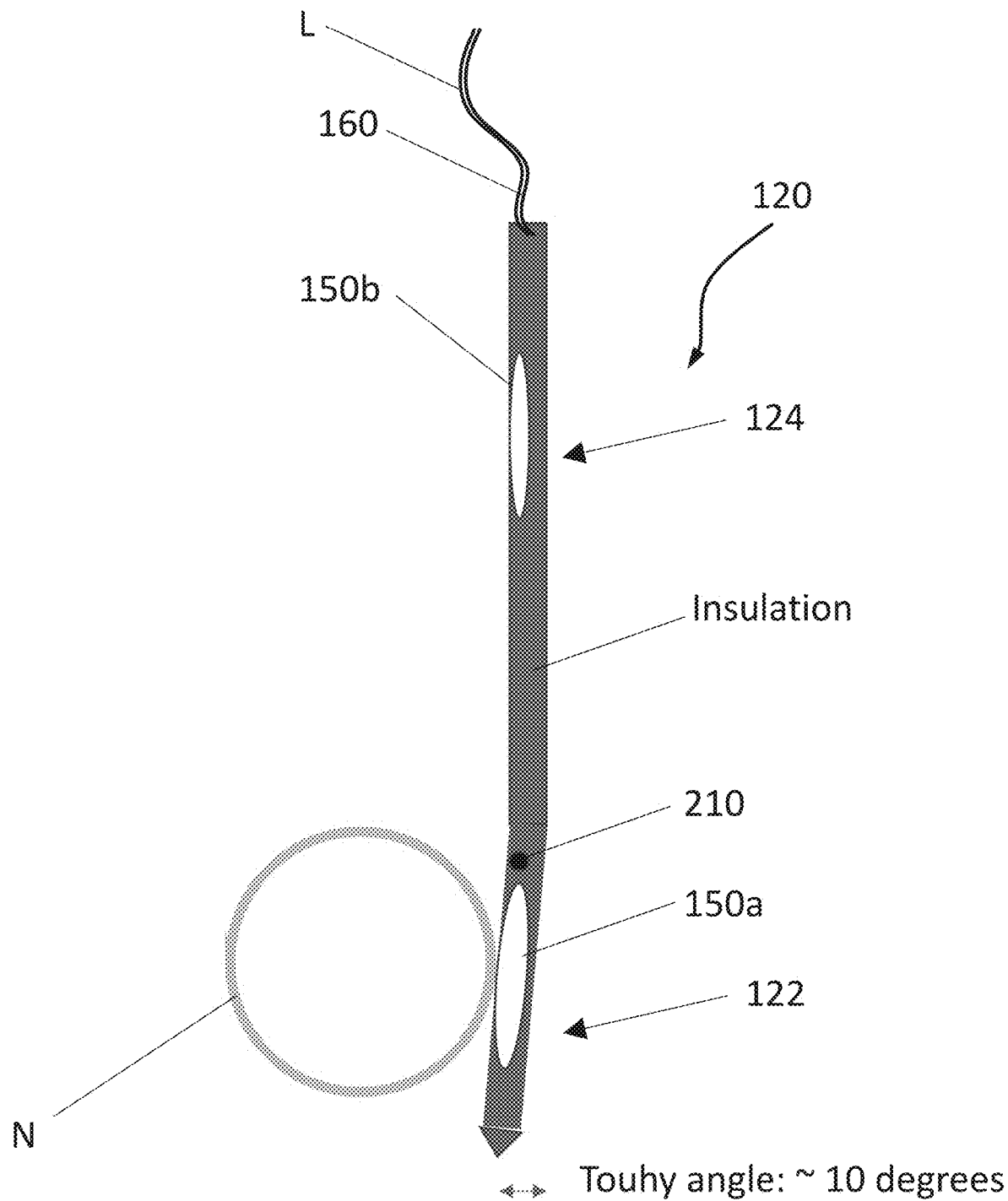

FIG. 3G provides another example percutaneous electrode 120 having distal tip extending at an angle with respect to the main body portion of the electrode 120. This bipolar configuration includes two electrical contacts 150 positioned along the elongated body of the electrode forming a cathode and anode in the vicinity of the nerve (N). As in each of the electrodes depicted in FIGS. 3A-3E and 3G, the length of the electrical contacts can be between 1 and 50 mm long, depending on the size of the target nerve/nervous structure. For example, the length of the electrical contacts can range between about 1 mm and about 30 mm. In another example, the length of the electrical contacts can range between about 2 mm and about 20 mm in length. In another example, the length of the electrical contacts can range between about 2 mm and about 15 mm in length. In a further example, the length of the electrical contacts can range between about 5 mm and 10 mm in length. It is contemplated that the length of each of the electrical contacts 150 included on an electrode 120/elongated body of the electrode 120 can be the same or different. For example, each of the electrical contacts 150 depicted on the electrode 120 of FIG. 3E have the same length to ensure a consistent and uniform electrical field is generated with respect to the nerve. In the example electrode 120 depicted in FIG. 3G, the length of the electrical contacts 150 varies along the electrode 120. In particular, the length of the distal electrical contact 150a located at the distal tip 122 of the electrode 120 is greater than the length of the proximal electrode 150b (positioned along the main body 124 the electrode 120 between the distal electrical contact 150a and a proximal end of the electrode 120). Generally, the distal electrical contact 150a can be at least twice the length of the proximal electrical contact 150b. In one example, the distal electrical contact 150a can be about 10 mm long, and the proximal electrical contact 150b can be about 4 mm long. In another example, the surface area of the distal electrical contact 150a and the proximal electrical contact 150b can be matched, while the length of the electrodes can be different. For example, if the proximal electrical contact has a greater circumference/circumferential width than the distal electrical contact then the proximal electrical contact could achieve a matched surface area by having a shorter length than the distal electrical contact.

As illustrated in FIG. 3G, the electrode 120 having an elongated body where the distal tip 122 of the electrode 120 extends at an angle with respect to the longitudinal axis of the main body portion of the electrode 120. It is contemplated that the angle of the distal tip portion 122 can range between about 0 and about 50 degrees. The angle of the distal tip portion 122 is between about 5 and about 15 degrees with respect to the main body 124/long axis of the electrode 120. The distal tip portion 122 of the electrode 120, beyond the bend, can extend at a straight line (as illustrated in FIG. 3G). It is also contemplated that the distal tip portion 122 can be curved or include a curved surface. As illustrated in FIG. 3G, the distal electrical contact 150a is located along the distal tip portion 122 and the proximal electrical contact 150b is located along the elongated main body portion 124 of the electrode 120. In this orientation, the distal electrical contact 150a is sized and configured to interface with the targeted nerve and the proximal electrical contact 150b is sized and configured to be positioned adjacent subcutaneous tissue, e.g., fat, fascia, muscle. In this configuration, tissue resistance between electrode 120/electrical contacts 150 is increased, resulting in higher voltages being delivered and lower currents, where lower current deliver provides less tissue heating.

FIG. 3F illustrates an example electrode 120 for use in treating a nervous structure and any overlying mucosal tissue. Specifically, the electrode of FIG. 3F is suitable for use in delivering electrical stimulation to the gasserian ganglion and/or the sphenopalatine ganglion (SPG). The stimulation device includes an elongated body portion 220 sized and configured to be advanced through the nostril of the patient and along the superior border of the middle nasal turbinate. One or more electrodes 120 are provided at a distal end of the elongated body portion 220. The electrode 120 has a contact surface having a size corresponding to a size of the SPG such that the electrical stimulation provided at the electrode 120 can modulate the entire SPG simultaneously and also provide a uniform pressure on a mucosal layer proximate/overlaying the SPG. In general, the contact area of the electrode 120 would range between 1.57-56 mm$^2$. With width of the contact surface of the electrode 120 ranges between at least 1 mm and 6 mm. In one example, the contact surface of the electrode 120 has an elongated triangular shape, a ball-tipped, or half-ball, or flat circular shape. As described above, the electrode of FIG. 3F is designed to be advanced through the nasal cavity to a position adjacent the sphenopalatine ganglion (SPG). As such, the elongated body portion 220 ranges from 5 cm long to 20 cm long. The elongated body portion 220 has a contour corresponding to a superior border of the middle nasal turbinate. To ease in delivery and position, it is also contemplated that the elongated body portion 220 is composes of a flexible material. Though not illustrated, it is contemplated that the stimulation device 100 and/or electrode 120 can be sized and configured to be placed in the patient's mouth. For example, the electrode 120 can be located on a mouthpiece fitted around the gums and teeth such that the electrode 120 is positioned on the gingival tissue (e.g., on the gum line). The electrode 120 can be located on the mouthpiece so that, when worn, it is located adjacent at least one of a ganglia or a peripheral nerve, including, for example, a lingual nerve, an alveolar nerve, and a buccal nerve.

As described above, the electrode 120 can include one or more contacts 150 for delivering the electrical stimulation to the treatment area/target nervous structure. A contact 150 is defined as a portion of the electrode 120 which is intended to form the interface between the electrode 120 and the tissue at which the electric stimulation is delivered to the tissue (such as to generate an electric field in the tissue). The electrode 120 and contact 150 configuration can be designed to maximize and direct the electric field and flow of current into the target nervous structure, and deliver a therapeutic dose of the electrical stimulation to nerves of various sizes and shapes and compositions, and without unwanted stimulation of nearby tissue, while ensuring reliable placement of the electrode 120 relative to the neural structure for optimum therapeutic effect.

Relevant design factors of the electrode include contact number, size, geometry, orientation, material, electrolytic medium, delivery fashion (e.g., monopolar, bipolar, multipolar), and return path. Adjustment and tuning of these factors enables the electric field and thermal field to be steered through the appropriate neural structure or portion neural structure to produce selective and reversible inhibition of pain. Additionally, adjustment and tuning of these factors enables the electric field and thermal field to be steered through the appropriate neural structure or portion of the neural structure to allow the therapeutic treatment to be effectively delivered in a single application and to adjust the time-course of reversibility of the treatment effects. Tuning and adjusting these factors also allows for shaping of the electric and thermal fields to treat the entire cross section of large nervous structures such as large peripheral nerves (>2.5 mm diameter), cranial nerves, ganglia, autonomic nerves, plexuses, and the spinal cord, as well as to treat portions of both large and small neural structures. For example, the size and shape of electrical contacts or the number of electrical contacts can be adjusted to optimize surface area contact with a large nerve. Likewise, the size and shape of electrical contacts or the number of electrical contacts can be adjusted to optimize surface area contact/electrical stimulation transmission to a nervous structure underlaying a mucosal tissue.

The electrode contact number, size, geometry, orientation, material, electrolytic medium, delivery fashion (e.g., monopolar, bipolar, multipolar), and return path can also be adjusted to prevent thermal damage to the tissue. These factors influence the thermal field produced by the electrical waveform, including the occurrence of thermal damage at some locations in the tissue relative to the electrodes, and adjustment of these factors, including adjustment in the context of cooling mechanisms and waveform adjustments, enables avoidance of thermal damage to the tissue.

For example, the electrode 120 is sized and configured to maximize and direct the electrical field created by the electrical stimulation delivered to the target nervous structure. The electrical contact 150 of the electrode can have a surface area ranging from about 1 mm$^2$ to about 100 mm$^2$ to accommodate the sizes of electric and thermal fields that are needed to deliver therapeutic treatment to portions of small and large nervous structures as well as to the entire cross section of small and large nervous structures. Preferably the electrode contact 150 has a surface area ranging from about 2.5 mm$^2$ to 45 mm$^2$. Electrical contacts which are too large may include portions of the contact 150 surface which do not contact the neural structure and, as a result, serves as a shunting pathway through which current may flow. When designing electrodes for therapeutic treatment of a nervous structure, shunting current is often discouraged because it increases the necessary current to be supplied from the controller in order to produce the therapeutic effect. As illustrated in FIG. 3G, the electrical contact 150 may also define a smooth curvilinear-shaped perimeter including, for example, circular- or oval-shaped contact surfaces. The sharp edges of rectilinear-shaped contacts, e.g., square- or rectangular-shaped contacts, can result in increased current densities and thermal heating. However, it is contemplated that rectilinear-shaped contacts 150 can be used when particularly sized and located on the electrode 120 to take advantage of the increase current densities and thermal heating. Thus, electrical contact sizes and shapes are optimized based on the desire to target delivery of the therapeutic electric field and thermal field to the nervous structure while maintaining the needed current flow from the controller to produce the therapeutic effects.

In another example, the electrode 120 can include at least two contacts 150 that operate dependently in a multipolar fashion to allow for current-steering and/or current-focusing of the resultant electric field. In another example, the electrode 120 includes at least two contacts 150 (e.g., two contacts 150 on the same electrode 120 or multiple electrodes 120 with their corresponding contacts 150) that operate independently. In this manner, the electrical simulation delivered by each of the electrodes 120 can be interleaved such that the total electrical stimulation delivered to the neural structure is delivered in less (half) the time. Specifically, each of the separate electrodes 120 can deliver an intermittent electrical stimulation signal, where the electrical stimulation of the first electrode is interleaved with the electrical stimulation of the second electrode, e.g., an "on cycle" of the first electrical stimulation delivery occurs during an "off cycle" of the second electrical stimulation and an "on cycle" of the second electrical stimulation delivery occurs during an "off cycle" of the first electrical stimulation.

In another example, the electrode 120 can include multiple electrode contacts 150 that can be selected for steering of the electric and thermal fields by selecting one or more electrode contacts 150 to be used as the anode and one or more other electrode contacts to be used as the cathode. The selection of different electrode contact combinations enables adjustment of the shape and size of the electric field and thermal field. For example, with respect to the electrode 120 of FIG. 3G, the distal and proximal electrical contacts 150a, 150b can be positioned on the same side of the elongated body/electrode 120. As such, the electrical contacts 150a, 150b do not deliver electrical energy circumferentially around the portion of the circumference of the elongated body electrode 120 without electrical contacts (e.g., the electrical contact 150a, 150b do not deliver electrical energy circumferentially to the short-axis of the body of the electrode 120), thereby providing voltage-field shaping and current steering of the delivered electrical stimulation. A brief test pulse of electrical stimulation may be delivered via a subset of contacts to determine proximity and coverage of the nerve, and more contacts may be added until sufficient contact with the nerve is verified (for example by monitoring motor output of the leg via movement or electromyography).

A resistor can be positioned in series with the electrical circuitry of the electrical contacts 150 of the electrode 120. For example, with respect to the electrode 120 of FIG. 3G, a resistor can be positioned in series with one or both of the electrical contacts 150a, 150b. The resistor will increase stimulation impedance and the voltage delivered from the generator 140 at or below the desired set-point temperature (e.g., destructive tissue temperature) and reduce stimulation current and thermal changes. Similarly, the electrical contacts 150 can be constructed from a material with high impedance or with high levels of capacitance. For example, materials with impedance or capacitance higher than that of stainless steel or platinum may be used to reduce stimulation current and thermal changes while still enabling delivery of a high voltage level. This will further increase the stimulation impedance and the voltage delivered from the generator 140 at or below the desired set-point temperature (e.g., destructive tissue temperature) while reducing stimulation current and thermal changes.

Generally speaking, the electrical stimulation may be delivered to the target nervous structure utilizing an electrode 120 that may be in the form of a percutaneous electrode assembly to temporarily and selectively modulate nerve fiber activity in the target nervous structure. For example, the electrode 120 can include an electrode assembly in the form of a paddle, cuff, cylindrical catheter or needle, wire form, or thin probe, configured to be introduced percutaneously through an opening in the patient's skin. In another example, for use in in the treatment of head and face pain (as described in more detail herein), the electrical stimulation may be delivered to the target nervous structure via and electrode 120 placed on a mucosal tissue of a patient, e.g., an electrical probe sized and configured to be advanced transnasally a target site proximate the gasserian ganglion and/or sphenopalatine ganglion (SPG).

Additionally, the electrical stimulation may be delivered to the target nervous structure via an electrode 120 implanted in the patient, for example for the treatment of chronic pain. In this case, the electrode 120 may be surgically implanted, and may be placed in contact or around the neural structure during a surgical procedure or during a minimally-invasive implant procedure. The electrode 120 may be secured to the neural structure and to surrounding tissue using sutures or using anchoring structures built on to the electrode that secure the electrode to neural structures or neighboring tissues.

The lead (L) includes a means for transmitting electrical energy between the electrical stimulation device 100 and the electrode 120, such as via a conductive wire or cable. The lead (L) may be directly attached to the electrode 120 in a permanent fashion or may be attachable and detachable using a conductive connector. In this case, compatible connectors would be present on the electrode 120 and on the lead (L). The lead may be directly attached to the electrical stimulation device 100/signal generator 140 in a permanent fashion or may be attachable and detachable using a conductive connector. In this case, compatible connectors would be present on the electrical stimulation device 100/signal generator 140 and on the lead (L). The lead (L) may also include avenues for transmission of fluid/gas, such as conduits 160 used for transmitting fluid/gas used to cool the electrode(s) 120. Fluid transmission conduits 160 may be connected to the electrode 120 and a cooling device directly or via attachable/detachable connectors. The lead (L) may also be contoured to provide a shape that is optimal for placement of the electrode 120, for example to allow navigation of the electrode into an ideal location near the nervous structure and to navigate around obstacles or tissue presenting a partial barrier between the insertion point and the target neural structure.

The lead (L) and electrode 120 may be placed with the help of lead introducer tools, such as cannulas, guidewires, introducer needles, and trocars. Particularly for percutaneous placement, these lead and electrode introducer tools may be used to navigate through the skin and underlying tissues to a position near the target neural structure. The introducer tool can also be used to allow for introduction/placement of all needed contacts 150 and other electrode components near the target neural structure. The lead (L), electrode, and introducer tools allow for placement of the electrode near both large and small target neural structures, including peripheral nerves, a cranial nerves, ganglia, autonomic nerves, a plexuses, and the spinal cord, and also enable appropriate interfacing between the electrode(s) and these target neural structures, which assists with producing selective and reversible inhibition of pain perception. The lead (L), electrode, and introducer tools also allow placement of the electrode 120 in cases of percutaneous use, for example for acute pain, and for implanted use, for example for chronic pain.

Figures 4A, 4B:
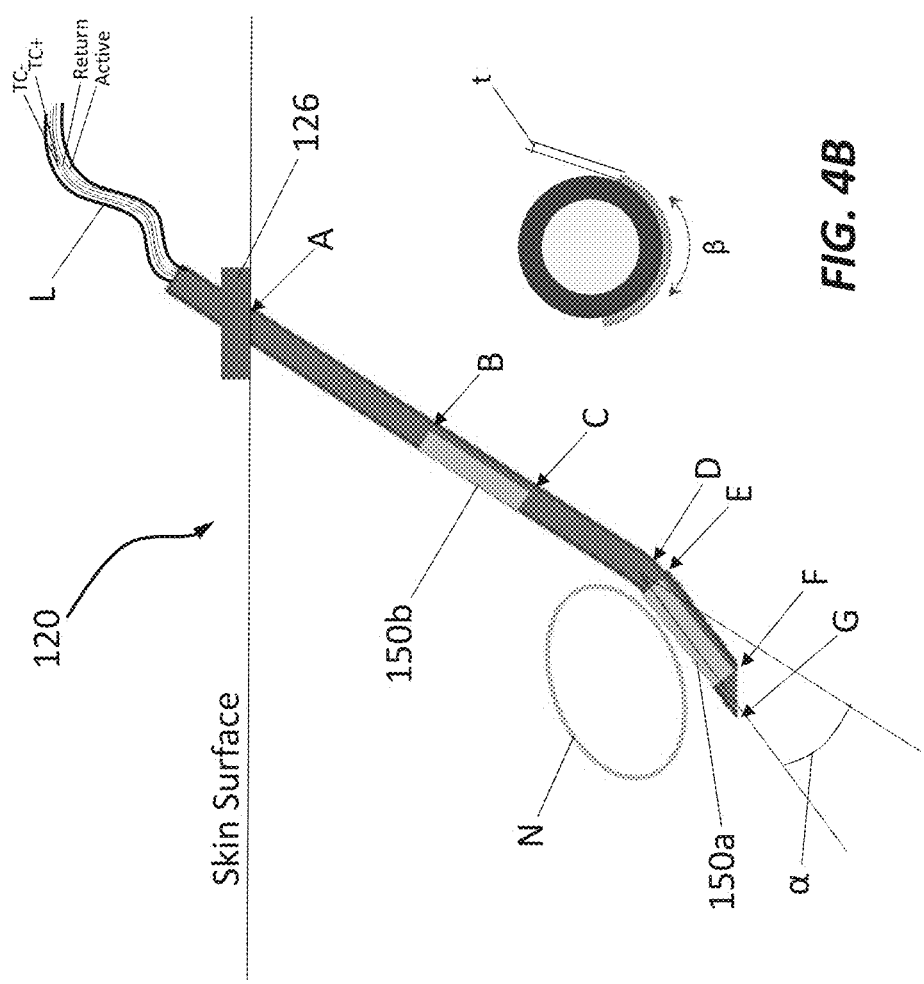
FIG. 4A is a schematic representation of an example percutaneous electrode positioned adjacent a target nerve.
FIG. 4B is a schematic cross-section view of the example electrode of FIG. 4A.

FIG. 4A provides a schematic representation of an example percutaneous electrode 120 (e.g., FIG. 3G) positioned adjacent a target nervous structure, for example, a peripheral nerve through an opening in the patient's skin. The electrode may consist of a single needle-like shaft with two electrical contacts 150. In this example, the distal electrical contact 150a serving as the active electrical contact near the target neural structure (N), and the proximal electrical contact 150b serving as the return electrode. As described above, the material of the shaft of the electrode 120 may be selected based on a desired to maximize thermal conductivity and/or thermal mass (e.g. to enable the electrode 120 to act as a heat sink, which may enable delivery of higher voltage or current treatment waveforms without raising the temperature of the tissue). The electrode 120 shaft material may also be selected based on a desire for the probe to be visible under ultrasound imaging (e.g., an echogenic material) or fluoroscopic imaging.

The distance (A-B) from the skin surface to the proximal electrical contact 150b (return contact) may be optimized to reduce risk of damage to skin or subcutaneous tissues. For example, the distance A-B can range between about 0 to about 40 mm. In another example, the distance A-B can range between about 0 to about 20 mm. In a further example, the distance A-B can range between about 5 mm to about 15 mm. In another example, the distance A-B can range between about 10 mm to about 15 mm. The distance (C-D) between the proximal electrical contact 150b (return contact) and the bend and/or distance (C-E) between the proximal electrical contact 105b and the distal electrical contact 150a (active contact) is selected to optimize treatment outcomes, for example, by shaping the voltage field to be preferentially oriented toward the target neural structure, or for example by focusing thermal energy during pulses of the therapy waveform, e.g., focusing thermal energy away from the target neural structure. In an example system, the distances C-D and C-E will each range between about 2 mm to about 50 mm. Preferably, the distances C-D and C-E will range between about 10 mm to about 30 mm.

The distance (C-D) between the proximal electrical contact 150b (return contact) and the bend and/or the distance (C-E) between the proximal electrical contact 150b (return contact) and the distal electrical contact 150a (active contact) may be selected to enable treatment of various target neural structures of different depths on patients with different anatomical configurations (for example, different thicknesses of muscle, skin, and fat layers, different depths to target neural structures, etc.). For example, the distance between the proximal electrical contact 150b (return contact) and the bend or the distal electrical contact 150a (active contact) (C-D or C-E) may be selected such that the distal electrical contact 150a (active contact) can be placed near a variety of target neural structures on a variety of different patients with a variety of different anatomical configurations, but such that the distance (A-B) between the skin and the proximal electrical contact 150b (return contact) is sufficient to enable efficacious delivery of energy without producing damage to the skin or other subcutaneous tissue. In another example, the electrode can have an adjustable distance (C-D or C-E) such that the proximal electrode contact 150b (return contact) can be repeatably placed in a desired anatomical location (e.g. in the fat layer or at a fixed distance beneath the skin) regardless of the depth of the target neural structure.

The distance (F-G) between the distal electrical contact 150a (active contact) and the distal tip of the electrode 120 may be selected to reduce spatio-temporal thermal spiking during delivery of the treatment waveform by avoiding delivery of current via geometrical structures on the contact 150a that could produce high current densities, such as a sharp, pointy tip. Additionally, the distance (F-G) between the distal electrical contact 150a (active contact) and the tip of the electrode 120 may be selected based on design and manufacturing considerations such as the selection of material for the electrode shaft and tip. For example, if the electrode shaft and tip is made of conductive material and is electrically connected or continuous with the distal electrical contact 150a (active contact), then the distal electrical contact 150a (active contact) may also include the tip of the electrode 120 (for example, because insulation over the sharp tip may be removed upon penetration through tissue). Conversely, if the electrode shaft and tip is made of non-conductive material and is not electrically coupled to the distal electrical contact 150a (active contact), then the distance (F-G) between the active contact and the tip of the electrode may be greater than 0 mm. The selection of this distance (F-G) may also be influenced by desired echogenicity of different probe components. Additionally, the tip of the electrode 120 may be configured to be smooth, non-pointy, or blunt in order to minimize high current densities or to overcome risks of insulation removal upon insertion.

The angle ($\alpha$) of the distal tip 122 of the electrode 120 may be selected to enable steering of the contacts 150 toward the target neural structure (N) during insertion and placement of the electrode 120. This angle ($\alpha$) also helps to direct delivery of the therapeutic waveform toward the target neural structure, for example, by steering the flow of current through the target neural structure, shaping the voltage field to be preferentially oriented toward the target neural structure, and/or focusing thermal energy during pulses of the therapy waveform toward the target neural structure.

The length (E-F) of the distal electrical contact 150a (active contact) may be selected to span the entirety of the diameter of a target neural structure, or to span only a portion of a target neural structure (e.g. a fascicle or group of fascicles). In one embodiment, the length (E-F) of the distal electrical contact 150a (active contact) and the length (B-C) of the proximal electrical contact 150b (return contact) may be identical. In other embodiments, the length (B-C) of the proximal electrical contact 150b (return contact) may be larger than the length (E-F) of the distal electrical contact 150a (active contact). The longer proximal electrical contact 150b (return contact) can ensure that the current density at the return contact is lower than the active contact (distal electrical contact 150a) (e.g. if the area of the return contact is greater than that of the active contact). The longer return contact (proximal electrical contact 150b) can also reduce likelihood of heating at the return contact (proximal electrical contact 150b) or near the skin and subcutaneous tissues. In another embodiment, the length (B-C) of the proximal electrical contact 150b (return contact) may be smaller than the length (E-F) of the distal electrical contact 150a (active contact). The longer active contact (distal electrical contact 150a) can increase the impedance of the therapeutic waveform circuit. A longer active contact (distal electrical contact 150a) can also be used to increase the voltage field at active contact while maintaining or reducing the current delivered to the tissue or the thermal heating of the tissue. Notably, increasing the impedance of the therapeutic waveform circuit may also be achieved, either in whole or in part, by adding a resistive element, as mentioned above, to the active or return pathway in the circuitry of the electrode 120. By adding a resistive element in line with an electrical cable or electrical routing element that connects to an electrical contact 150. The cable itself may also act as a resistive element in the circuit.

FIG. 4B provides a schematic cross-section view of the electrode 120 and electrical contact 150 of FIG. 4B. The active and/or return contact of the electrode 120 may also be oriented to have a contact arc length (β) that is completely circumferential (360) or, as illustrated in FIG. 4B, a contact arc length (β) that is only partially circumferential (<360). In some embodiments, the contact arc length (β) is less than 180. Reduction of the contact arc length (β) may be used to further direct delivery of the therapeutic waveform toward the target neural structure (N), for example, by steering the flow of current through the target neural structure, shaping the voltage field to be preferentially oriented toward the target neural structure, and/or focusing thermal energy during pulses of the therapy waveform toward the target neural structure. Additionally, reduction of the contact arc length (β) may also help to reduce the amount of current that travels through pathways in the tissue that do not include the target neural structure (for example, shunting currents) or to reduce the exposure of non-target-neural-structure tissue to the voltage field provided by the therapeutic waveform. These measures may reduce the power consumption of the system and reduce risks to non-target tissues. In one example, the distal electrical contact 150a (active contact), which is closest to the nerve, has an arc length less than 180° to reduce shunting currents and to preferentially steer current toward the nerve, whereas the proximal electrical contact 105b (return contact), which is most-distant from the nerve, has an arc length greater than 180. In this example, use of a higher arc length for the return electrical contact enables matching of the surface areas of the two contacts while minimizing the (longitudinal) length of the return contact, which may enable optimal separation distance between the two contacts.

The thickness (t) of the electrical contact 150 may also be specified to enable manufacture of electrodes 120 at a specified needle gauge while providing sufficient electrical contact mass to withstand mechanical and electro-chemical stresses on the contact materials that may be incurred during use of the electrode 120. For example, the thickness (t) of the electrical contact 150 can range between 0.01 thousandths of an inch to 50 thousandths of an inch.

An electrode holder 126 may be incorporated into the design to help secure the electrode 120 and minimize movement of the electrode 120 after placement is completed. For example, an electrode holder 126 may help to stabilize the position of the distal electrical contact 150a (active contact) relative to the target neural structure (N) during delivery of the therapeutic waveform. An electrode holder 126 may also allow a user deliver the therapeutic waveform without being required to hold the electrode 120 in place for the duration of the waveform delivery. The lead (L) can include the electrical cables and connectors to the electrode 120 may be used to provide electrical connection to the distal electrical contact 150a (active contact), proximal electrical contact 150b (return contact) and to a temperature sensing element 210 (e.g. TC– and TC+).

Echogenic features, such as laser etched or mechanically etched materials, may also be incorporated at desired positions on the electrode to enable enhanced visualization under ultrasound imaging.

The temperature sensing element 210 (also referred to as temperature sensor) can be selected to provide a desired accuracy (for example +/–2° C., or for example +/–1° C., or for example +/–0.5° C., or for example +/–0.3° C.) and a desired range (for example 0-100° C., or for example 20-80° C., or for example, 30-70° C.). Thermocouple accuracy is impacted by the ambient temperature at any cold junctions as well as manufacturing factors. Additionally, the temperature sensing element 210 and the electrode 120 can be designed to provide a desired response speed in the temperature measurements (for example, a time constant of 0-500 ms, or a time constant of 0-100 ms, or a time constant of 0-10 ms, or a time constant of 0-1 ms). The shape/size of a thermocouple junction as well as the specific heat capacity of the materials used in the electrode 120 and the thermocouple/temperature sensing element 210 can be designed to produce a desired temperature measurement response speed.

Figure 10:
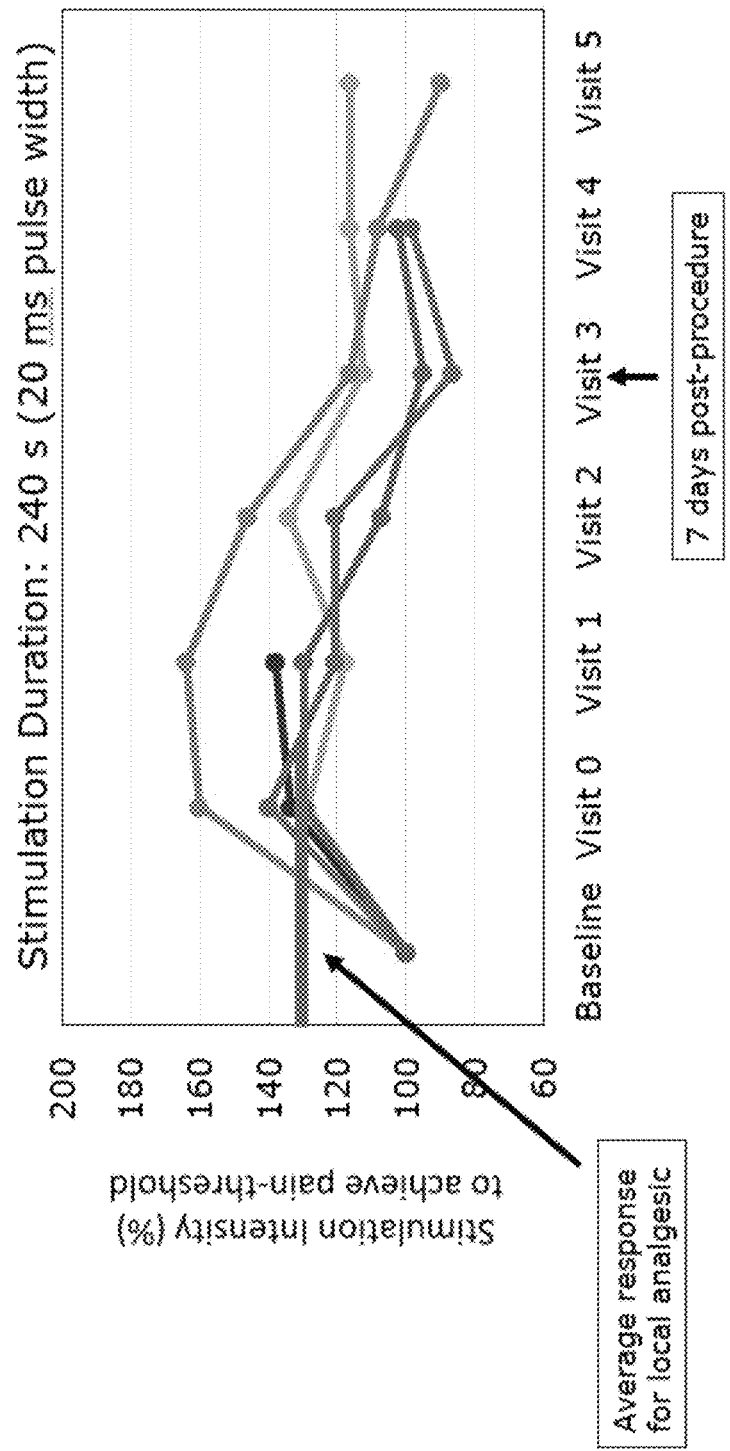
FIG. 10 is a table proving experimental results.

FIG. 10 illustrates various example bipolar electrical contact 150/electrode 120 configurations. As will be described in more detail below, example configurations A-D illustrate a single body electrode 120; example configurations E-H illustrate a single body electrode 120 with a concentric contact structure as described with respect to FIGS. 11A and 11B, the electrode 120 used in conjunction with a windowed introducer cannula 230; example configurations illustrate a flexible electrode 120 used in conjunction with a curved introducer cannula 230; and example configurations K-M illustrate a straight electrode 120 used in conjunction with a straight introducer cannula 210. It is contemplated that any of these configurations, individually or in combination, can be used on any of the electrodes 120 discussed herein.

As will be described below, the example configurations include single-body electrode 120 designs and multi-body electrode 120 designs. For example, configurations A-D and E-H illustrate example single-body configurations, composed of a single electrode 120 shaft including two electrical contacts 150. The tip of the electrode 120 can be rounded and smooth (e.g. A, E-H) or sharp (e.g., B-D). The proximal electrical contact 150b (return contact) may be fully circumferential (e.g. A and B) or partially circumferential (e.g., C-H). The distal electrical contact 150a (active contact) may be shaped in various different geometries based on the desire to include/exclude the electrode 120 tip as an electrical contact and/or to direct the therapeutic waveform toward the target neural structure. A lumen may be incorporated in all designs to allow for injection of fluid through the electrode 120. For example, the lumen can be used to deliver drug therapy to the treatment site (e.g., an analgesic) before, during and/or after delivery of the electrical stimulation. In example D, avoidance of a sharp tip as part of the active contact is achieved by use of a second body which does not have an electrical contact. In this case, a sharp introducer needle which protrudes from the central lumen extending through the electrode 120. Here the sharp introducer needle can be removed after placement of the electrode 120 or when fluid is desired to be injected via the lumen. In examples E-H, a cannula 230 that does not have an electrical contact is used to provide a path for insertion of the single-body electrode 120. This cannula 230 may be placed initially without the single-body electrode, for example with use of a sharp introducer needle. After placement, the introducer needle may be removed and the electrode 120 may be inserted into the cannula 230. The cannula 230 may be used to provide windowed-access 232 to the return or active contacts (e.g. windowed access to the return contact in examples E-F). The cannula may be curved or straight (curved in E-F, straight in G-H). The electrode may also be curved or straight (curved in G-H, straight in E-F).

Multi-body designs, such as the examples shown in I-M, are composed of multiple shafts with electrical contacts 150. In these examples, the return electrical contact 150a is provided on the cannula 230 and a second body 234 with the active electrical contact 150b is inserted through the central lumen of the cannula 230. A multi-body can be used to provide an electrode with an adjustable distance between the active and return electrical contacts. For example, the second body 234 can be moved longitudinally within the cannula 230 until a desired spacing between the active and return electrodes 150b, 150a is reached. Once in a desired position and orientation, the position of the second body 234 within the cannula 230 is fixed.

The cannula 230 may be curved (e.g. I-J) or straight (K-M). The electrode body 234 that includes the active electrical contact 150b may be curved (e.g. K-M) or straight (I-J).

As illustrated in FIG. 10, the active and return electrical contacts 150b, 150a can be combined with various combinations of electrical contact arc lengths. For example, configurations A, B, I, K and L include electrical contacts where both the active and return electrical contacts 150b, 150a extend around a majority of the circumference of the electrode 120 (e.g., more than 180°, 270°, 360°). For example, configuration A illustrates an electrode 120 having active and return electrical contact 150b, 150a extending around the entire circumference of the electrode 120. Configurations E-H, J, M provide example electrodes 120, where the return electrical contact 150a extends around less of the circumference of electrode than the active electrical contact 150b. Likewise, the example configurations illustrate active and return electrical contact 150b, 150a combined with various shape combinations, e.g., configuration J where the return electrical contact 150a has a rectilinear shape, and the active electrical contact 150b has a curvilinear shape. FIG. 10 also illustrates active and return electrical contact 150b, 150a combined in various contact lengths and circumferences, e.g., configurations B and C provide an electrode where the return electrode 150a has is shorter (along the longitudinal axis of the electrode 120) than the active electrode 150b; configurations J and M provide an electrode where the return electrode 150a is longer than the active electrode 150b; configurations I, K illustrate an probe where the return electrode 150a has a circumference greater than the active electrode 150b.

Figure 6B:
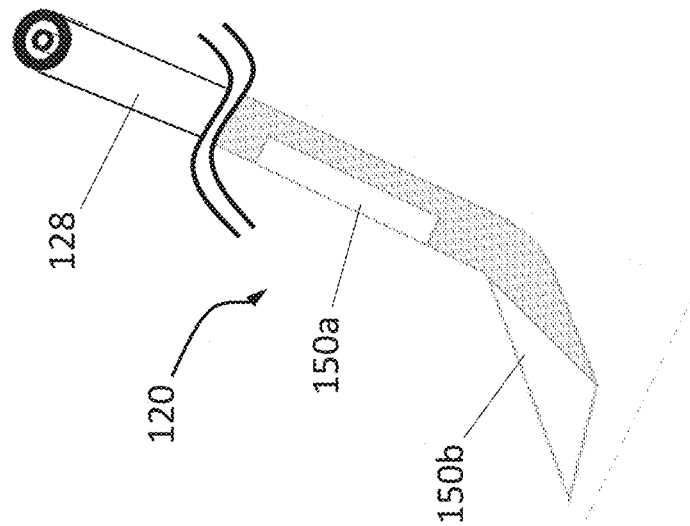
FIGS. 6A and 6B are an example electrode connection.
Figure 6A:
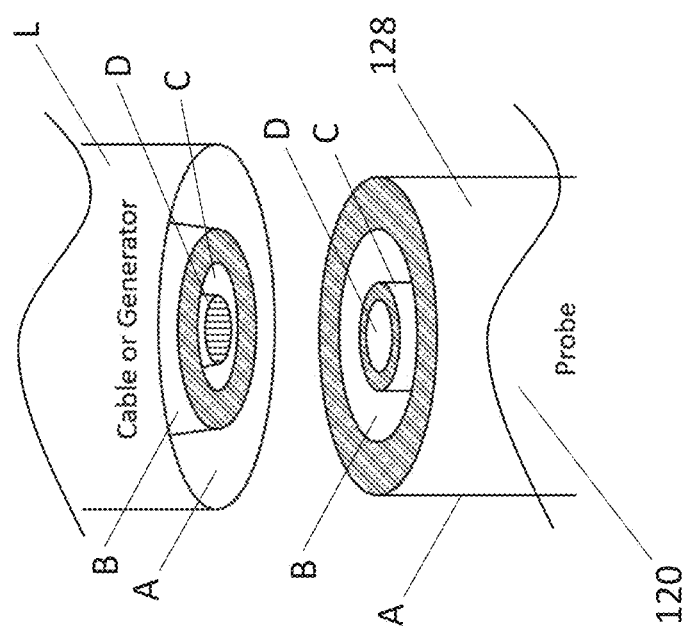

FIGS. 11A and 11B illustrate an example connection between the electrode 120 and the lead (L) electrically coupling the electrode 120 to the generator 140. The connection can be facilitated via the design of the proximal end of the electrode 120 and/or an electrode connector 128 coupled to the proximal end of the electrode 120. As provided in FIG. 6A, the electrode 120 and/or electrode connector 128 can include a concentric design, such that multiple circumferentially-shaped contacts are arranged as layered concentric surfaces around the long axis of the electrode 120. For example, as illustrated in FIG. 6A, contact A is the outer-most conductive surface, contact B an inner conductive surface (oriented facing the long axis of the electrode 120), contact C another inner conductive surface (oriented facing away from the long axis of the electrode 120), and contact D the inner-most conductive surface (oriented facing the long axis of the electrode 120). The concentric surfaces may each be electrically connected to unique components of the electrode 120 (e.g., active electrical contact (distal electrical contact 150a), return electrical contact (proximal electrical contact 150b), and/or temperature sensing element 210). The concentric surfaces can be separated by dielectric layers including, for example, an electrically insulating materials and/or air provided between adjacent conductive surfaces. For example, a dielectric layer that ranges in thickness from 0.01 thousandths of an inch to 50 thousandths of an inch can be provided between the adjacent concentric surfaces. The needle gauge may vary along the shaft of the electrode 120, or may be constant, in order to accommodate concentric designs. Additionally, the needle gauge may be selected to provide for passage of a lumen in addition to the routing of the active, return, and temperature sensing electrical traces/circuitry.

The lead (L) may include a compatible cable and/or connector for electrically coupling the electrode 120 and/or an electrode connector 128 with the generator 140. The lead (L) cable/connector includes concentric surfaces (e.g., A, B, C, D) having a corresponding size and shape and configured to electrically mate with the corresponding concentric surfaces of the electrode 120/connector 128 and provide reliable and consistent electrical connectivity between the generator 140 and the electrode 120.

The concentric surfaces can be designed to compress or expand when suitable mechanical pressure is applied thus enabling a reliable and snug fit between the lead (L) and the electrode 120. For example, the concentric surfaces provided on the lead (L) and/or the electrode 120/connector 128 can include notches in some of the conductive surfaces or the dielectric layers provided between the concentric surfaces. The notches allow for controlled expansion of the concentric surface while maintaining consistent contact with the corresponding surface of the electrode 120 (or lead (L)).

The concentric design of the lead (L) and/or electrode can include a lumen for allowing the passage of fluid through and/or between the lead (L) and the electrode 120. For example, the probe connector 128 can include a lumen extending within in the inner-most concentric layer (and/or between other concentric layers) allowing for the attachment of a syringe or tube to the connector 128 and injection of fluid through the inner-most concentric layer or between other concentric layers.

Additionally, the concentric design may be adopted not only as a component of the connector, but also as a means of routing the electrical circuitry of the electrical contacts and temperature sensing elements from their terminal sites to the proximal end of the electrode 120 for connection to the generator 140. The concentric design, including the conductive surfaces and the dielectric layers may also be used along the electrode 120 shaft. Such a design lends itself to straightforward manufacturing methods and potentially to use of the electrode 120 shaft for providing the connection with the lead (L), i.e., without the use of a connector 128, as illustrated in FIG. 6B.

Additionally, the material type and thickness for the dielectric layers between the concentric surfaces, as well as the material type and thickness of the conductive layers, may be selected to minimize capacitance and/or maximize impedance between conductive layers (e.g. to reduce shunting and parasitic capacitance and to maximize delivery of the therapeutic waveform to the tissue while minimizing power requirements of the electrical generator).

One or more temperature sensors/thermal sensing elements 210 may be included on the electrode 120 to provide feedback regarding the electrode 120 and/or tissue temperature at specified locations. In one example, the temperature sensor(s) 210 are placed at locations which are anticipated to be the sites of highest temperature, for example near locations of highest predicted current density, this includes, for example, sharp pointy tips, edges of contacts, discontinuities or rapid spatial transitions between materials of different electrical conductivities. The selection of these temperature sensor placement locations may be determined based on modeling studies or in-vitro or in-vivo temperature measurements in tissue or in model media such as saline, conductive gel formulations, or egg whites. Temperature sensor traces may be routed in a manner that reduces the level of electromagnetic interference introduced by the waveform delivery into the temperature sensing circuit.

In addition to the concentric arrangement, various other arrangements can be appreciated for routing the active and return electrical contacts and thermal sensing elements from their terminal sites to the position where they connect to the lead (L) cable or generator 140 including, for example, routing of insulated wires, use of dielectric layers with non-insulted wires, and printing electrical traces using electrically conductive ink, etc. Additionally, the materials used for routing the active and return contacts and thermal sensing elements from their terminal sites to the position where they connect to the lead (L) cable or generator 140 may be carefully selected to enable reliable and efficacious transmission of electrical signals without contamination or without shunting. It should also be appreciated that such approaches may be employed for cases where multiple electrical contacts 150 or multiple thermal sensing elements 210 are used on a single electrode 120.

Example Signal Generator

The electrical stimulation device 100 can include a signal generator 140 coupled to the electrode 120 and the controller 130. The signal generator 140 produces the stimulation waveform, including the parameters of the stimulation waveform discussed above. The signal generator 140 includes the necessary software and hardware components to produce the specified stimulation waveform(s) and to allow for modulation of the stimulation waveforms by means of the controller 130. The signal generator 140 also includes the ability to deliver stimulation to the nervous structure via the electrode(s) 120 while electrically isolating the electrode 120 and patient from grounded circuitry and other ground connections, such that the patient is not grounded when the electrode(s) are introduced in the patient's body. This is accomplished, for example, via inductors or via optical isolators. Additionally, the signal generator 140 can include capacitors, inductors, resistors, and other passive circuit components near the output to the electrode 120 which ensure charge balance, reduce DC offset, or otherwise provided the desired regulation of the waveform parameters discussed earlier. Furthermore, feedback monitoring circuitry can be incorporated to collect information regarding the waveform delivered (such as the current, voltage, power) and the temperature (for example as monitored via a temperature monitoring mechanism (e.g., temperature sensor 210) at the electrode 120 or otherwise in the tissue). Parameters of the cooling mechanism such as temperature of the fluid/gas cooling medium, flow rate and pressure of the fluid/gas, the heat transfer rate from the electrode 120 and/or surrounding tissue, etc. may also be gathered.

Example Controller and Power Supply

As described generally above, the controller 130 directs operation of the stimulation device 100/signal generator 140 to provide the electrical stimulation to the target neural structure by means of the electrode 120. The controller 130/signal generator 140 are electrically coupled to a power source 180 that supplies the electrical energy to the stimulation device 100/electrode 120. The power source 180 can include an isolated power supply, such that all the instruments in the system can be powered by an isolated power supply 180 to protect them from ground faults and power spikes carried by the electrical main. The power source 180 can also include one or more batteries, used either for primary or backup power, which would allow the device to be operated without attachment to the electrical main at the facility.

Specifically, the controller 130 directs operation of the signal generator 140 to deliver an electrical stimulation signal to the target nervous structure. The controller 130 may have onboard memory to facilitate high speed data capture, output control, and processing, as well as, independent waveform sample rates and on-line analysis. These components of the controller enable collection of the feedback data needed to understand the waveform delivered via the electrode as well as the parameters of the cooling mechanism and the thermal and electrical state of the tissue. This feedback enables tuning of such treatment parameters in order to provide selective and reversible inhibition of pain.

As illustrated schematically in FIG. 1, the stimulation device can include one or more electrodes 120 connected by to an electrical lead (L) to the controller 130 via the signal generator 140. The controller 130 can include control logic and software designed to deliver the desired electrical stimulation to a patient. The controller 130 can also process analog and digital data, and record waveform data and digital information from the patient monitor system 190 and can generate waveform outputs, analog outputs, and digital outputs simultaneously for real-time control of the electrical stimulation (either real-time automated control, or manual user control). For example, the controller 130 can adjust the electrical stimulation in response to feedback information received from temperature sensors coupled to the electrode 120 and/or the stimulation device 100. For example, the stimulation device 100/electrode 120 can include a thermocouple for measuring the temperature at the contact surface of the stimulation device and/or the electrode contacts, and the patient's tissue adjacent the contact surface of the electrode 120. The temperature sensors are coupled to the controller 130 and provide feedback information regarding a measured temperature at the contact surface of the stimulation device 100 and/or the contact surface of the electrode 120 and/or at other locations in the tissue. The controller 130 or the user can then adjust a parameter of the electrical stimulation in response to the feedback information, the parameters including, for example, a waveform shape, a waveform frequency range, a waveform amplitude range, an electrical field strength generated at the electrode, a waveform DC offset, a waveform duty cycle (e.g., continuous delivery or intermittent delivery) a tissue temperature, a cooling mechanism parameter, and a treatment duration. Additional feedback signals that may be relayed or recorded by the controller or used for feedback control of the electric signal include temperature, contact impedance, the current, voltage, and power of the electric signal, other parameters of the electric signal, information regarding the electric field in the tissue, blood flow, skin conductance, heart rate, muscle activity (such as electromyography), or other physiological signals.

Feedback control of the electrical stimulation is desirable to avoid producing damage in tissue, to tune the sphere of modulation of the electrical stimulation within the target neural structure, and to tune the sphere of modulation of the electrical stimulation to target both small and large nervous structures and a diversity of nervous structures such as peripheral nerves, a cranial nerves, ganglia, autonomic nerves, plexuses, and the spinal cord. Feedback control of the electrical stimulation is also desirable to enable tuning of the time-course of reversibility of the inhibition of perception of pain, to tune the selectivity of the inhibition of perception of pain, and to ensure that adequate inhibition of pain is achieved, for example, with a single treatment.

Whether adjusting the electrical stimulation to selectively modulate nerve signal transmission through a select type of nerve fiber and/or through a select region of the nervous structure, the control and/or operation of the controller 130 can be adjusted varying a parameter of the electrical stimulation based on a measured feedback of the inhibition of nerve signal transmission (e.g., confirmation of no or limited nerve signal transmission from/through the target nerve), and/or a measured feedback of the temperature at the treatment site, and/or feedback from the patient regarding pain perception. Confirmation of no/limited nerve signal transmission can be achieved via intraoperative monitoring techniques including, for example, recorded EMG, direct neural recordings that demonstrate pain fiber response change in latency and/or amplitude or burst area. The controller 130 and the user interface are also used to adjust the parameters of the stimulation waveform and properties of the electrode configurations and the cooling mechanism in response to feedback. For example, the controller 130 is configured to vary the duty cycle and/or stimulation envelope duration of the electrical stimulation in real-time, during treatment, to maximize the voltage delivered to the treatment site while not exceeding a target tissue temperature at the treatment site, i.e., a destructive tissue temperature. Similarly, in some embodiments, the controller is configured to vary the duty cycle and/or the stimulation waveform envelope duration of the electrical stimulation in real-time to maximize current delivered to the treatment site while not exceeding a target tissue temperature at the treatment site, i.e., a destructive tissue temperature. Providing an immediate temperature-responsive feedback loop allows a therapeutic voltage (or current) to be delivered to the target nervous structure for as long as possible without causing damage. By controlling current the user is able to more easily control for tissue temperature and safety. Likewise, voltage control is correlated to treatment efficacy.

Alternatively, a user can manually adjust parameters of the stimulation waveform and properties of the electrode configurations and the cooling mechanism in response to feedback provided via the user interface 170.

Example User Interface

The stimulation device 100 may further include a user interface 170 for receiving input from and providing input to the user (e.g., patient or medical professional). The user may provide input directing operation of the stimulation device 100 including modifications to the electrical signal. The user interface 170 can further include a display providing information to the user regarding the stimulation device 100. For example, the display can provide information regarding a status of the stimulation device 100, e.g., on/off, signal delivery mode, parameter date regarding the electrical signal, etc. The user interface 170 may be integral to the stimulation device 100. It is also contemplated that the user interface 170 may be incorporated into a remote device that is electrically (wire or wireless) coupled to the stimulation device. For example, the user interface 170 may be provided on an external tablet computer or phone. The user interface 170 may be used to allow the user to actively control parameters of the electrical stimulation (in real time) in response to feedback information from the controller 130.

The system can also include a patient monitoring system 190. The patient monitoring system 190 may be used in conjunction with the stimulation device and the user interface 170. The patient monitoring system 190 acquires, amplifies and filters physiological signals, and outputs them to the controller 130 and/or the user interface 170 for feedback. The monitoring system can include a temperature sensor coupled to an outer surface of the patient's skin for measuring changes in the patient's surface body temperature, a blood flow meter coupled to the patient's skin or inserted through the patient's skin, a skin conductance meter coupled to the patient's skin, a heart-rate monitor to collect electrocardiogram signals corresponding to the patient's heart rate, and a muscle activity monitor to collect electromyography signals. A heart-rate monitor may include separate electrocardiogram (ECG) electrodes coupled with an alternating current (AC) amplifier. A muscle activity monitor may include separate EMG electrodes coupled with an AC amplifier. Other types of transducers may also be used. As described, all physiological signals obtained with the patient monitoring system are passed through a signal amplifier/conditioner. The parameters of the electrical stimulation can be adjusted in response to the feedback information received at the patient monitoring system 190 by either the controller 130 or user. For example, at least one parameter of the electrical signal can be adjusted by the controller 130 in response to feedback information received from the temperature sensor, an impedance meter, the blood flow meter, the skin conductance meter, the heart rate monitor, and the muscle activity monitor. Information regarding the stimulation waveform and parameters as well as the electrical the thermal properties of the tissue, the electrode, and the cooling mechanism can also be provided via the user interface 170 and used to adjust at least one parameter of the electrical stimulation or the cooling mechanism or the electrode configuration. The adjusted parameter of the electrical signal can include, for example, a waveform shape, a waveform frequency range, an waveform amplitude range, a waveform envelope duration range (i.e., the period of time the stimulation energy is delivered ("on"), e.g., a continuously delivered stimulation energy has a long envelope duration, and a pulsed stimulation energy has a short envelope), an electrical field strength at the electrode, a waveform DC offset, a waveform duty cycle (e.g., continuous delivery, intermittent delivery), a tissue temperature, a cooling mechanism parameter, and a treatment duration. Additionally, the electrode configuration (e.g. bipolar, multipolar, monopolar, interleaved, etc.) can also be adjusted in response to feedback information.

Example Method

The present disclosure encompasses a method for selectively and reversibly modulating targeted neural- and non-neural tissue of a nervous structure with a single application of electrical energy to inhibit pain perception by a patient. The method of practicing the present invention begins with positioning the patient in a comfortable position. A heart rate monitor (ECG), a muscle activity monitor (EMG), or any other monitor may be utilized to measure the patient's response to the electrical stimulation signal. The patient may be monitored for a period of time to determine a baseline status before the application of the electrical stimulation signal.

Next the targeted nervous structure can be identified and located. If the electrical signal is to be delivered transcutaneously, the targeted nervous structure may be located utilizing a stimulation device such as a nerve locator (e.g., Ambu® Ministim® nerve stimulator and locator), utilizing the electrode 120. The nerve can also be located by passing low-levels of stimulation energy signal through the stimulation device. A stimulus-elicited muscle twitch in a distal muscle group with low stimulation amplitudes (single pulse) will indicate that the stimulation point is close enough for modulating nerve signal transmission.

The electrical stimulation device 100 is then positioned at the treatment site proximate the targeted neural- and non-neural tissue of the nervous structure. Electrode(s) 120 can be positioned near the nervous structure in a percutaneous or transnasal fashion, or by open incision and implantation.

Figure 5:
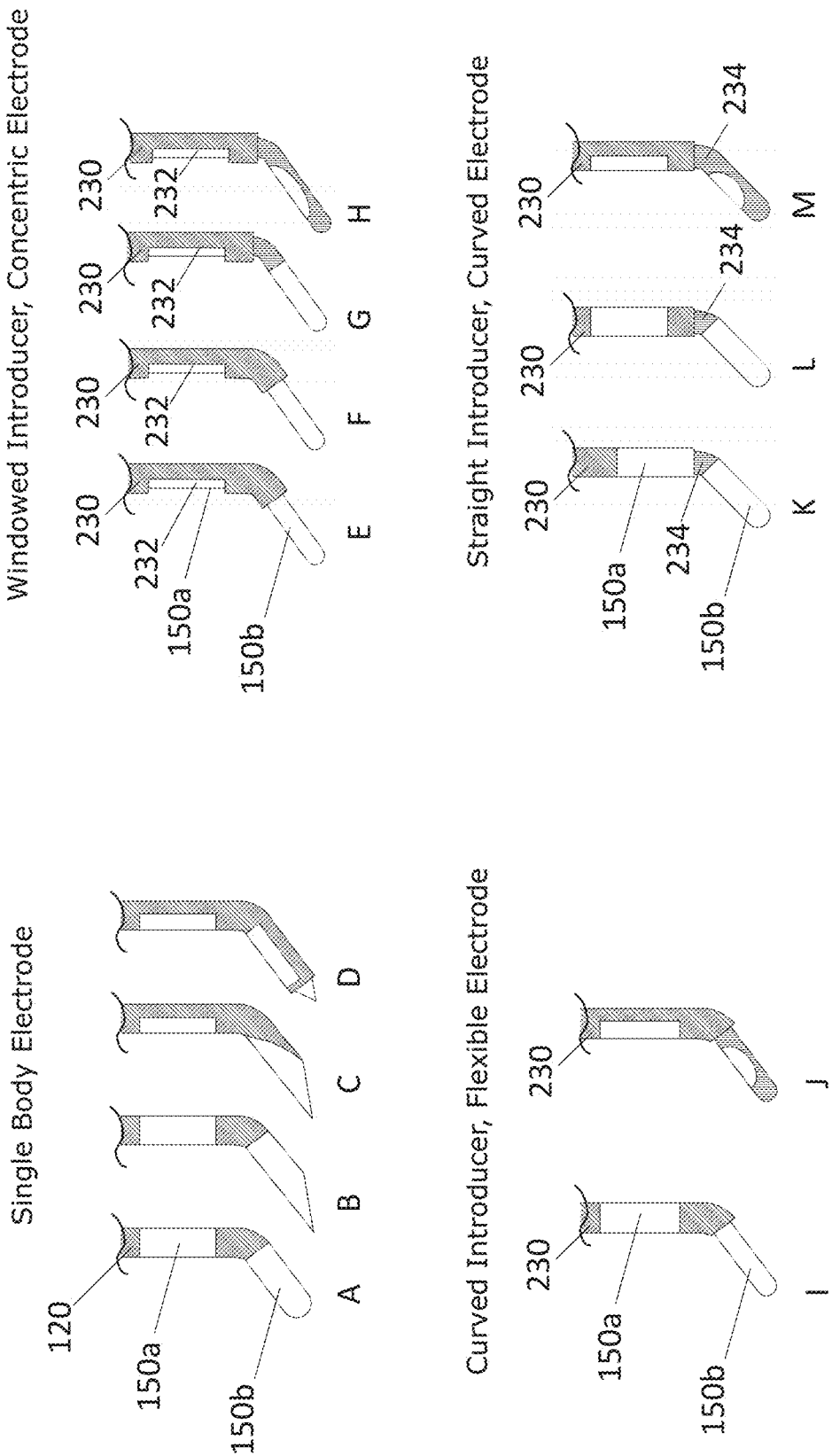
FIG. 5 is various example bipolar electrical contact and electrode configurations.

For example, electrodes 120 can be positioned percutaneously adjacent the nervous structure through an opening in the patient's skin (S) (see e.g., FIG. 5). The (internal) electrodes 120/leads (L) are attached to an external stimulation device/signal generator 140, or can be fixed to a handheld stimulation device. Placement of the electrodes 120 percutaneously may include penetration of the skin and navigation of the electrode 120 and/or lead (L) under imaging guidance (such as with ultrasound) to a location proximate the target neural structure. Additional positioning tools may be used, such as cannulas, guidewires, introducer needles, and trocars to enable navigation of the tissues and eventual placement of the electrode proximate the target neural structure.

Positioning the electrode 120 near the nervous structure may including delivering an initial electrical stimulation (i.e., low level electrical stimulation, <0.5 V) to the treatment site via the electrode 120 and measuring the voltage and/or the current at the electrode 120. Based on the measured voltage and/or current, the position of the electrode 120 at the treatment site (near the target nervous structure) is adjusted. Further initial electrical simulation signals are delivered to the treatment site and the position of the electrode 120 is adjusted, iteratively until the measured voltage and/or current corresponds to a threshold voltage and/or threshold current indicating that the electrode 120 is positioned about the nerve at a location to delivery effective therapy.

Where the electrical signal is delivered percutaneously, the method may further include positioning one or more return electrodes on the outer surface of the patient's skin. Each anode desirably has a skin contacting surface such that the skin contacting surface of the anode has at least the same (or greater) surface area as the contacting surface of the stimulating electrode. One or more return electrode may be positioned on the skin a distance away from one or more stimulating electrodes sufficient to avoid shunting.

The method of practicing the present invention may further include the use of coupling media such as, for example, an electrically conductive liquid, gel or paste that may be applied to the skin in the case of return electrode or disposed within a sheath around the electrode 120 or at the tip of the electrode 120 in the case of the percutaneous placed electrode 120 in order to maximize and direct the electric field, deliver the therapeutic dose of stimulation energy to small and large nerves, and ensure reliable electrode/nerve placement for optimum therapeutic effect. Alternatively and/or additionally, one or more skin moisturizers, humectants, exfoliators or the like may be applied to the skin for the purpose of enhancing the conductivity of the skin and/or lowering impedance of the skin. Example conductive pastes include Ten20™ conductive paste from Weaver and Company, Aurora, Colo., and ELEFIX Conductive Paste from Nihon Kohden with offices at Foothill Ranch, Calif. Examples of conductive gels include Spectra 360 Electrode Gel from Parker Laboratories, Inc., Fairfield, N.J., or Electro-Gel from Electro-Cap International, Inc., Eaton, Ohio. An example exfoliator that can be used to prepare skin prior to application of transcutaneous electrodes is Nuprep skin prep gel from Weaver and company, Aurora, Colo.

In a further example, the electrodes can be implanted within the patient adjacent the treatment site and proximate the target neural structure. The electrodes and the stimulation device can be implanted at or near the target neural structure. In another example the electrodes can be implanted at the treatment site with the leads extending through the patient's skin to the stimulation device. It is also contemplated that the electrodes can be implanted at the treatment site and can be wirelessly activated through the patient's skin. It is also contemplated that a wireless receiver module can be implanted and used to receive input wirelessly from the controller 130, and then communicate with the electrode via lead wires.

Figure 9B:
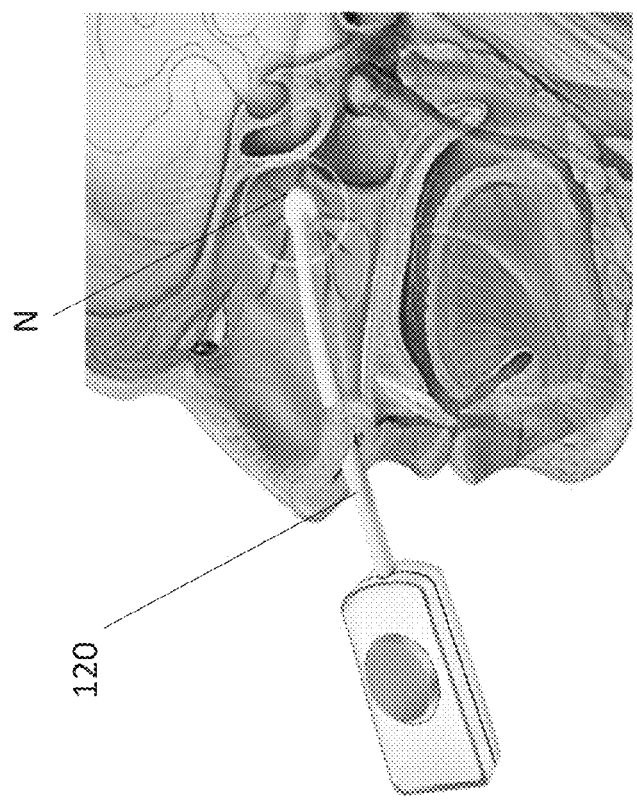
FIGS. 9A and 9B are schematic representations of positioning an electrode and delivering an electrical stimulation the sphenopalatine ganglion.
Figure 9A:
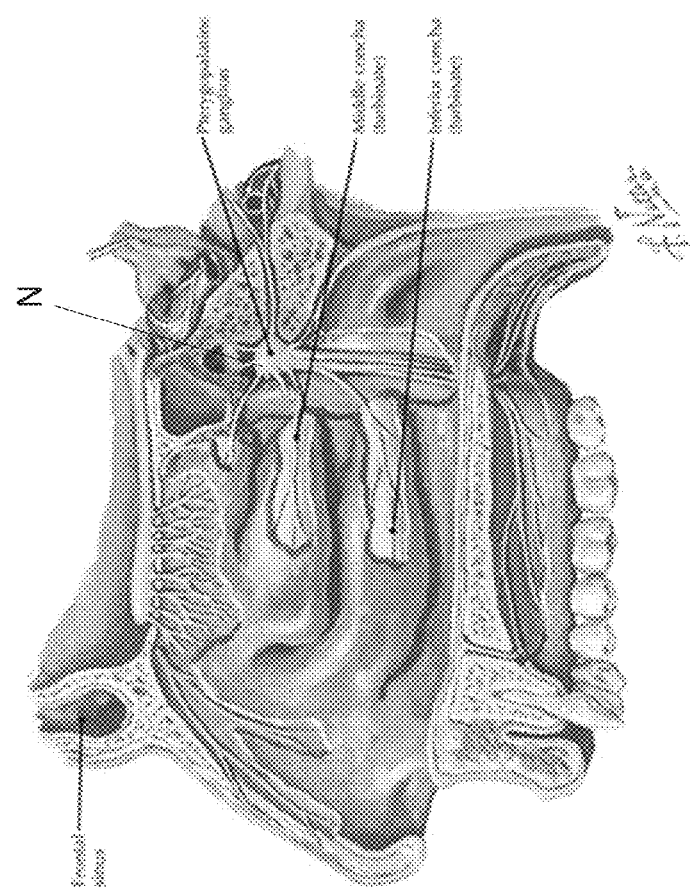

An additional example is placement of the electrode 120 (e.g. FIG. 3F) in a nasal turbinate via a transnasal approach for transmucosal delivery of the electrical signal to the gasserian ganglion and/or sphenopalatine ganglion (SPG). For example, the electrode 120 and lead may be inserted into the patient's nose and placed in a nasal turbinate and held securely in position during delivery of the electrical signal (see e.g., FIGS. 9A and 9B). A method may be used in which the patient's sneeze reflex is suppressed, for example, using chemical block or electrical nerve block or by intentionally evoking a sneeze reflex and then placing the lead and electrode immediately after the sneeze before the patient is able to generate a second sneeze reflex. The intentional initial sneeze reflex may be triggered by the lead and/or electrode or by a separate probe inserted into the nose. It is also contemplated that the electrode 120 can be positioned adjacent the gasserian ganglion and/or sphenopalatine ganglion (SPG) via a percutaneous approach. Whether via a transnasal or percutaneous approach, the position of the SPG may be initially located using, for example, magnetic resonance imaging (MRI), fluoroscopy, and ultrasound imaging.

After electrodes 120 are placed, traditional electrical stimulation can be delivered through the electrodes 120 to assure sufficient tissue/nerve proximity, and impedance measurements can be collected and used similarly. The stimulation device can then be programmed to optimize electrode contact selection, return electrode selection and stimulation parameters, as discussed above. It is contemplated that selection of optimal stimulation parameters can include delivery of different candidate waveforms with different parameter configurations until a suitable outcome is achieved. It is further contemplated that selection of optimal electrode contact 150 configurations and return electrode configurations can include delivery of electric signals via different configurations of electrode contacts 150 and return electrodes until a suitable outcome is achieved. These optimizations may be performed manually by the user or may be delivered by the controller in closed-loop as part of an algorithmic iterative search or a pre-programmed search. If desired, a chemical nerve block agent can also be delivered through the electrode lead prior to delivering the electrical signal. The chemical nerve block can help to mitigate onset response and improve patient comfort.

The stimulation electrical signal can then be delivered to the treatment site proximate targeted nervous structure via the electrode(s) using one or more of the stimulation parameters discussed above. The controller 130, receiving a supply of electrical energy from a power source 180 can direct operation of the stimulation device to provide an electrical signal sufficient to selectively modulate the targeted neural- and non-neural tissue inhibiting the patient's perception of pain while also preserving other sensory and motor function, and proprioception. The user may also control the parameters of the electrical signal in real time in response to feedback provided via the controller 130 to the user interface 170. A single application of the electrical signal to the treatment site can selectively modulate the targeted neural- and non-neural tissue and provide subsequent inhibition of perception of pain, for a period of about 1 day to about 30 days.

Where the electrode comprises at least two electrodes that operate independently, it is contemplated that a first electrical simulation signal may be delivered via the first electrode and a second electrical stimulation signal via the second electrode. The first and second electrical stimulation signals can be intermittently outputted, where the first electrical stimulation is interleaved with respect to the second electrical stimulation. In this configuration, the on cycle of the first electrical stimulation occurs during an off cycle of the second electrical stimulation. Similarly, the on cycle of the second electrical stimulation occurs during an off cycle of the first electrical stimulation.

The perception of pain by the patient is inhibited as the application of the electrical signal to the treatment site selectively modulates the targeted neural- and non-neural tissue modulating the nerve signal transmission through nerve fibers that are responsible for the transmission of pain. Meanwhile, nerve signal transmission through nerve fibers responsible for other sensory and motor function, and proprioception is preserved. The preserved "other" sensory function includes, for example, touch, vision, audition, gustation, olfaction, and balance. Application of the electrical signal can also inhibit and/or disrupt nerve signal transmission through nerve fibers responsible for transmitting signals related to thermoreception, autonomic activity and visceral function.

In its simplest form, the method may rely on a patient's feedback regarding their perception of pain after delivery of nerve blocking stimulation signal to assess the effectiveness of the temporary and selective nerve modulation. In some examples, the patient's sensations, such as heartbeat sensations, tingling, heaviness, and/or deep pressure, experienced during stimulation can be used to direct various simulation parameters including, for example, voltage, current, stimulation impedance and treatment time-course (duty cycle and stimulation time-course; treatment duration and termination time; dosing (stimulation "on" time).

Alternatively and/or additionally, the method may rely on feedback collected by a recording electrode, such as an ECG, galvanic skin response, blood flow meter, skin or body temperature, and/or electromyogram signals to assess the effectiveness of the temporary and selective nerve modulation, since the stimulation may occur before, during, or immediately after a surgical procedure when the patient is not able to provide feedback.

The target nervous structure can comprise a peripheral nerve (large or small), a cranial nerve, a ganglion, an autonomic nerve, a plexus, and a spinal cord. Target neural structures can include a mixture of motor, sensory and/or autonomic neurons, or may include a single type of neural activity (such as motor only, sensory only, autonomic only). Target ganglia can include a dorsal root ganglia, a sympathetic ganglia, a parasympathetic ganglia, a sphenopalatine ganglion, a gasserian ganglion, a plexus, and/or the spinal cord. In one example, the target nervous structure comprises a large peripheral nerve (such as greater than about 2.5 mm) and the electrodes deliver an electrical signal to the nerve that selectively and reversibly inhibits nerve signal activity associated with pain for a period of days to weeks, with preservation of nerve signaling associated with motor function, non-painful sensation, and proprioception. For example, the electrodes 120 can deliver an electrical signal that selectively and reversibly inhibits nerve signal activity in smaller diameter nerve fibers associated with sensory (pain) function for a period of days-to-weeks, with minimal or no change in the functionality of the larger myelinated fibers that are associated with motor function, non-painful sensation, and proprioception. In one example, the application of the electrical signal to the neural- and non-neural tissues of the targeted nervous structure inhibits and/or disrupts nerve signal transmission through at least one of a myelinated Aδ fiber and/or an unmyelinated C fiber provided in the nerve, wherein the electrical signal preserves nerve signal transmission through at least one of the Aβ and Aα fibers, and/or motor fibers. In a further example, various parameters of the electrical signal can be adjusted to selectively inhibit at least one of the myelinated Aδ fibers or the unmyelinated C fibers, e.g., inhibit nerve signal transmission through the myelinated Aδ fibers while preserving nerve signal transmission through the unmyelinated C fibers, and vise-a-versa. In a further example, various parameters of the electrical signal can be adjusted to differentially inhibit nerve signal transmission/function of the myelinated Aδ fibers, such that the myelinated Aδ fibers have a larger percentage of fibers inhibited than the unmyelinated C fibers. Likewise, various parameters of the electrical signal can be adjusted to differentially inhibit nerve signal transmission/function of the unmyelinated C fibers, such that the unmyelinated C fibers have a larger percentage of fibers inhibited than the myelinated Aδ fibers.

In another example, the application of the electrical signal to the neural- and non-neural tissues of the targeted nervous structure modulates neural or non-neural tissue function in a way the results in downstream or secondary effects that result in the inhibition of pain, while preserving motor, non-painful sensory, and proprioceptive activity. For example, various parameter of the electrical signal can be adjusted to selectively modulate function which results in reduction of pain that originated from activity in myelinated Aδ fibers and/or unmyelinated C fibers, while preserving motor, non-painful sensory, and proprioceptive function, such as that transmitted by Aβ and Aα fibers, and/or motor fibers. In a further example, various parameters of the electrical signal can be adjusted to selectively modulate function which results in reduction of pain that originated from activity in myelinated Aδ fibers or the unmyelinated C fibers, e.g., inhibit pain that originated from activity in myelinated Aδ fibers while preserving pain that originated from activity in unmyelinated C fibers, and vise-a-versa. In a further example, various parameters of the electrical signal can be adjusted to differentially modulate function which results in reduction of pain that originated from activity in myelinated Aδ fibers, such that the pain originating from activity in myelinated Aδ fibers has a larger inhibition than the pain originating from activity in unmyelinated C fibers. Likewise, various parameters of the electrical signal can be adjusted to differentially modulate function which results in reduction of pain that originated from activity in unmyelinated C fibers, such that the pain originating from activity in unmyelinated C fibers has a larger inhibition than the pain originating from activity in myelinated Aδ fibers.

In another example, certain parameters of the electrical signal can be adjusted to preferentially modulate nerve signal transmission/function within a desired region of the nervous structure. Generally, the desired region is that portion of the nervous structure including the sensory components responsible for transmitting a sense of pain. For example, with respect to the femoral nerve, topography of the femoral nerve indicates that portions of sensory components innervating the knee are collected together in a region of the nerve cross-section. Accordingly, it is contemplated that the electrical signal can be adjusted to preferentially modulate nerve signal transmission through the portion of the nerve cross-section corresponding to these target sensory components.

The various, modifiable parameters of the electrical signal include, for example, a waveform, a frequency, an amplitude, a waveform envelope duration, an intensity, an electrical field strength, a waveform offset (DC offset), a continuous delivery, and/or intermittent delivery through the electrode 120. For example, the controller 130 adjusts the duty cycle and/or waveform envelope duration in real-time to maximize voltage delivered to the treatment site, while not exceeding a target tissue temperature at the treatment site, e.g., modulating the stimulation duty cycle and/or stimulation envelope to maximize the voltage delivered to the treatment site in real-time while ensuring the tissue at the treatment site does not exceed a destructive tissue temperature. Similarly, in some embodiments, the controller 130 adjusts the duty cycle and/or waveform envelope duration in real-time to maximize current delivered to the treatment site, while not exceeding a target tissue temperature at the treatment site, e.g., modulating the stimulation duty cycle and/or stimulation envelope to maximize current without exceeding a destructive tissue temperature.

In another example, the stimulation amplitude of the electrical stimulation can be slowly ramped to a plateau. Ramping the electrical stimulation to plateau can eliminate and/or reduce the magnitude of sensations experienced by the patient during delivery of the electrical stimulation (e.g., tingling sensation in the experienced in the receptive field of the nerve when the stimulation energy is continuous; intermittent tingling sensations experienced when stimulation energy is delivered as pulses).

The disclosed method encompasses inhibiting the perception of pain associated with acute pain (including surgical pain, post-surgical pain, trauma pain), neuropathic pain, chronic pain, and head-and-face pain. Where the pain is acute pain, the method for selectively and reversibly modulating targeted neural- and non-neural tissue to inhibit the perception of pain may include applying the electrical signal immediately before the surgical procedure. The electrical signal can also be applied intraoperatively and/or immediately following a surgical procedure to inhibit the perception of pain associated with the surgical procedure and recovery. The electrical signal may also be applied hours and/or days in advance of a procedure. For example, the electrical signal may be applied at least 24 hours prior to a surgical procedure. Delivery of the electrical signal in advance of a procedure, such as a surgical procedure, helps to reduce pain and patient discomfort as the patient prepares for the procedure. Delivery of the electrical signal in advance of a procedure can also be configured to enable peak pain relief effect to occur at the time of the procedure. It is also contemplated that multiple nervous structures may be targeted to enable more-comprehensive coverage of a target area. For example, where the pain is post-surgical acute pain following a knee arthroplasty procedure (including a total knee arthroplasty procedure), the electrical stimulation can be applied to the femoral nerve, the sciatic nerve, the obturator nerve, and the lateral cutaneous nerve and nerve branches, or a combination thereof. In another example, where the pain is shoulder pain, the electrical stimulation can be applied to the brachial plexus, the axillary nerve, the suprascapular nerve and lateral pectoral nerve, or a combination thereof. Where the pain is associated with a medical procedure and/or trauma to the arm and/or hand, the electrical stimulation can be applied to the medial, ulnar and radial nerves individually and/or the brachial plexus. Where the pain is associated with a medical procedure and/or trauma to the ankle and/or foot, the electrical stimulation can be applied to the tibial, peroneal/sural and saphenous nerves, or a combination thereof. Where the pain is associated with a hip arthroplasty, the electrical stimulation can be applied to the femoral, sciatic, or obturator (e.g., common obturator before branching into anterior and posterior) nerves and/or plexus, or a combination thereof. Where the pain is associated with repair of the anterior cruciate ligament (ACL), the electrical stimulation can be applied to the femoral, or sciatic nerve, or a combination thereof.

Where the pain is neuropathic pain or chronic pain, the method for modulating the neural- and non-neural tissue of the target nervous structure may include the user (such as a physician or a patient) applying the electrical signal as part of a pre-determined schedule for preventative care, and/or as needed by the patient to provide an on-demand bolus of therapeutic treatment/pain relief.

The method for selectively and reversibly modulating targeted neural- and non-neural tissue to inhibit the perception of pain may further include measuring, at a temperature sensor 210, the temperature the contact surface of the stimulation device 100 (e.g., electrode 120 contact surface) and/or the temperature of the patient's tissue adjacent the stimulation device contact surface during delivery of the electrical signal. The feedback information regarding the measured temperature is provided to the stimulation device. If the feedback information indicates that the temperature of the contact surface of the stimulation device is above a device threshold temperature and/or if the temperature of the patient's tissue is above a tissue threshold temperature, the stimulation device/controller or the user can adjust the operation of the stimulation device and the parameters of the electrical signal and/or a cooling mechanism to produce a cooling effect and reduce the temperature at the contact surface and tissue. Reducing the temperature of the contact surface and/or the patient's tissue prevents damage to the patient's tissue. In some examples, the system may include a cooling mechanism coupled to and/or integrated into the stimulation device 100 and/or electrodes 120. If the feedback information indicate that the temperature of the contact surface of the stimulation device 100 is above a device threshold temperature and/or if the temperature of the patient's tissue is above a tissue threshold temperature, the stimulation device 100/controller 130 and/or the user, may activate and control operation of the cooling mechanism to cool the contact surface of the stimulation device 100/electrode 120 where cooling the contact surface prevents damage to the patient's tissue when the electrical signal is delivered by preserving temperatures of the patient's tissue below a tissue threshold temperature. Likewise, the stimulation device 100/controller 130 and/or the user, may activate and control operation of the cooling mechanism to maintain the temperature of the contact surface of the stimulation device 100/electrode 120 below a threshold temperature in response to feedback information regarding the measured temperature received from the temperature sensor 210.

After the electrical signal has been delivered, and the perception of pain has been inhibited while preserving other sensory and motor function, and proprioception, the percutaneous and/or transcutaneous electrodes 120 can be removed. Meanwhile, implanted electrodes 120 (if any) can remain inside the body for further usage and ongoing treatment.

Example 1

In this example, able-bodied subjects were recruited from the community and consented for the study using IRB-approved consent forms. High-dose opioid users were excluded from the study. Two types of sensory assessment were performed at multiple time-points in each subject: 1) mechanical vibration testing to assess the subject's sensitivity to non-painful touch sensation, and 2) pain-evoking electrical stimulation testing to assess the subject's sensitivity to evoked pain. At the beginning of the first session, mechanical vibration testing and pain-evoking electrical stimulation assessments were performed on each leg. These were referred to as the baseline assessments. The subject then received treatment using the electrical stimulation waveform via a percutaneously-placed electrode on the left leg. After the treatment, the mechanical and vibration testing was again assessed on each leg. Subjects returned in subsequent visits for mechanical vibration testing and pain-evoking electrical stimulation testing.

Mechanical vibration testing: Subjects donned scrubs and were seated in a comfortable chair. The right leg was secured in a straight position to a stand with foam padding to restrict movement. A vibration device was placed in contact with the skin within the saphenous nerve distribution. Vibration trials were then performed in which a series of two epochs were provided to the subject, one including a vibration via the vibration device and the other not including a vibration. For each trial, the selection of which epoch in which vibration was delivered was determined randomly and the subject was requested to indicate verbally which epoch was the epoch during which he or she believed the vibration had been delivered. If the subject selected the correct epoch, a duplicate trial was delivered until successful selection had been made for three sequential trials, after which the vibration amplitude was decreased for the next trial. If the subject selected the incorrect epoch, the next trial was delivered at a higher amplitude of stimulation. In this fashion the threshold amplitude was identified based on the combined performance from 3 sets of 50 trials on each leg. The threshold amplitude was identified for each leg in each session.

Pain-evoking electrical stimulation testing: Electrical stimulation was delivered via sticky surface electrodes placed over the saphenous nerve near the medial malleolus. The stimulation duration was 1 ms for single pulses. The amplitude of stimulation was increased gradually until the subject first perceived sensation. The stimulation was then delivered in a train of 9 pulses at 500 Hz and the stimulation amplitude was gradually increased until the subject perceived a transition from non-painful sensation to painful sensation. The pain threshold was identified via both ascending and descending limit tests and the average pain threshold for that session was documented. This threshold was identified for each leg in each session.

Electrical stimulation treatment: Electrical stimulation treatment was delivered in a single treatment to each subject in the left leg only. After the baseline mechanical vibration testing and the baseline pain-evoking electrical stimulation testing, the subject was prepared for delivery of the electrical stimulation treatment.

The subject was placed supine on a procedure table and the skin was prepped at a site over the saphenous nerve several centimeters distal and medial to the tibial tuberosity. A surface return electrode was placed on the contralateral leg over the gastrocnemius muscles. Ultrasound was used to identify the saphenous nerve and a radiofrequency probe (22-gauge, 4-mm exposed tip) was inserted through the skin. The position of the radiofrequency probe active tip was manipulated while stimulation (1 ms duration, 2 Hz) was delivered at progressively lower amplitudes. Manipulation of the probe position was performed until a sensory threshold was achieved at less than 0.2 V.

The electrical stimulation treatment was then delivered to the subject at 2 Hz, 20 ms, for 240 s. The amplitude of the stimulation was adjusted in real time to maintain a probe tip temperature of 42° C. After completion of the stimulation the probe was removed and the subject again underwent mechanical vibration testing and pain-evoking electrical stimulation testing, referred to as visit 0.

Subjects returned for follow-up assessment in subsequent visits. Vibration thresholds were plotted over time to assess the effect of the electrical stimulation treatment on touch sensation, such as sensation transmitted via large-diameter myelinated fibers. Pain thresholds were normalized to the baseline level and plotted over time to assess the effect of the electrical stimulation treatment on painful sensation, such as sensation transmitted via small-diameter fibers.

FIG. 10 shows the normalized pain thresholds over time for five subjects which received 240-s-duration electrical stimulation treatments. The green line shows the average response for local analgesics such as lidocaine or bupivacaine, which provide analgesia for a period of less than a day. An increase in pain thresholds was evident for all subjects, indicating a decreased sensitivity to pain. Return to baseline was evident by seven days post-procedure.

Figure 11:
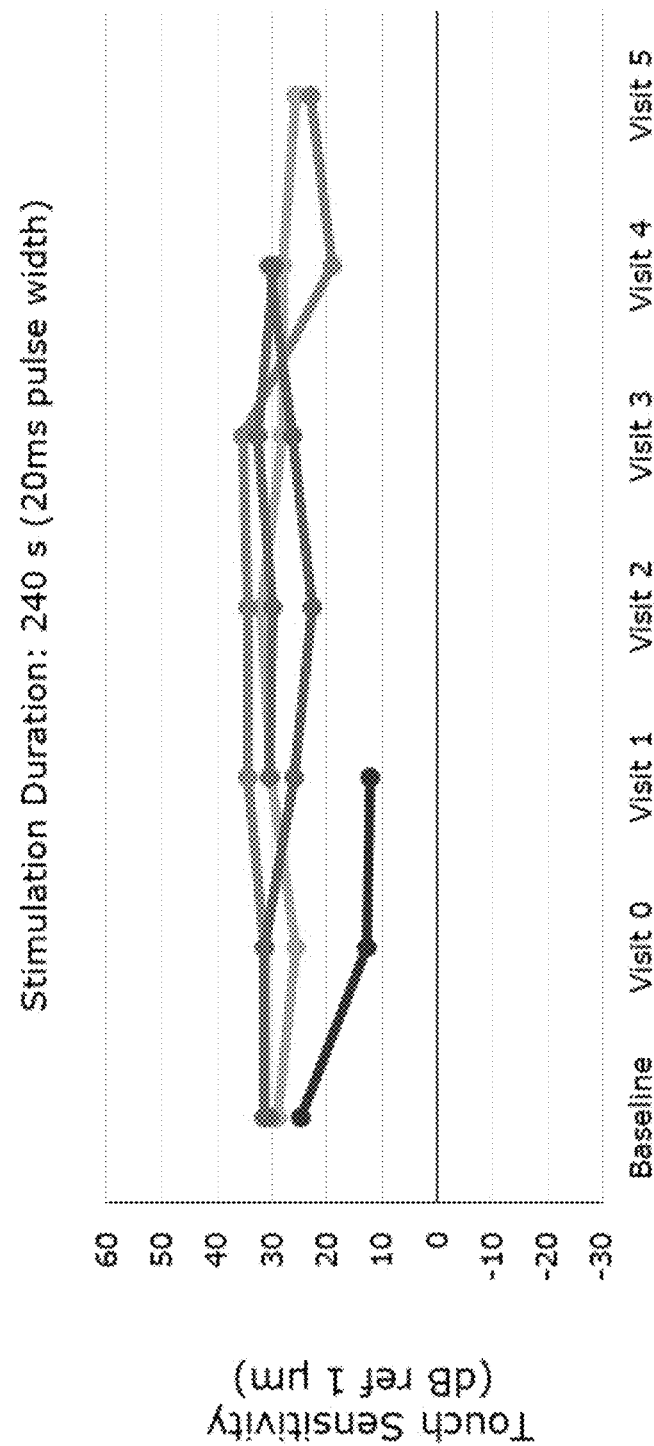
FIG. 11 is a table proving experimental results.

FIG. 11 shows the mechanical vibration thresholds over time for the same five subjects (240-s-duration electrical stimulation treatments). No systematic change in mechanical vibration thresholds was evident, suggesting selectivity of the treatment toward pain perception. Additionally, results of a clinical exam also did not indicate any sensory deficits on the treated leg.

These results suggest that the electrical stimulation treatment selectively and reversibly increases the threshold to perception of pain via a treated nerve with full reversibility within 7 days after treatment.

Example Computing System

While the methods and systems have been described in connection with preferred embodiments and specific examples, it is not intended that the scope be limited to the particular embodiments set forth, as the embodiments herein are intended in all respects to be illustrative rather than restrictive.

As used herein, "computing device" may include a plurality of computers. The computers may include one or more hardware components such as, for example, a processor, a random access memory (RAM) module, a read-only memory (ROM) module, a storage, a database, one or more input/output (I/O) devices, and an interface. Alternatively, and/or additionally, controller may include one or more software components such as, for example, a computer-readable medium including computer executable instructions for performing a method associated with the exemplary embodiments. It is contemplated that one or more of the hardware components listed above may be implemented using software. For example, storage may include a software partition associated with one or more other hardware components. It is understood that the components listed above are exemplary only and not intended to be limiting.

Processor may include one or more processors, each configured to execute instructions and process data to perform one or more functions associated with a computer for indexing images. Processor may be communicatively coupled to RAM, ROM, storage, database, I/O devices, and interface. Processor may be configured to execute sequences of computer program instructions to perform various processes. The computer program instructions may be loaded into RAM for execution by processor. As used herein, processor refers to a physical hardware device that executes encoded instructions for performing functions on inputs and creating outputs.

A processor can be microcontrollers, microprocessors, or logic circuits such as ASICs (Application Specific Integrated Circuit), CPLDs (Complex Programmable Logic Device), FPGA (Field Programmable Gate Array), or other programmable logic integrated circuits. In some embodiments, a processor is configured to execute instruction stored in a memory of the device.

RAM and ROM may each include one or more devices for storing information associated with operation of processor. For example, ROM may include a memory device configured to access and store information associated with controller, including information for identifying, initializing, and monitoring the operation of one or more components and subsystems. RAM may include a memory device for storing data associated with one or more operations of processor. For example, ROM may load instructions into RAM for execution by processor.

Storage may include any type of mass storage device configured to store information that processor may need to perform processes consistent with the disclosed embodiments. For example, storage may include one or more magnetic and/or optical disk devices, such as hard drives, CD-ROMs, DVD-ROMs, or any other type of mass media device.

Database may include one or more software and/or hardware components that cooperate to store, organize, sort, filter, and/or arrange data used by controller and/or processor. For example, database may store hardware and/or software configuration data associated with input-output hardware devices and controllers, as described herein. It is contemplated that database may store additional and/or different information than that listed above.

I/O devices may include one or more components configured to communicate information with a user associated with controller. For example, I/O devices may include a console with an integrated keyboard and mouse to allow a user to maintain a database of images, update associations, and access digital content. I/O devices may also include a display including a graphical user interface (GUI) for outputting information on a monitor. I/O devices may also include peripheral devices such as, for example, a printer for printing information associated with controller, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface may include one or more components configured to transmit and receive data via a communication network, such as the Internet, a local area network, a workstation peer-to-peer network, a direct link network, a wireless network, or any other suitable communication platform. For example, interface may include one or more modulators, demodulators, multiplexers, demultiplexers, network communication devices, wireless devices, antennas, modems, and any other type of device configured to enable data communication via a communication network.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed:

1. A system for selectively and reversibly modulating targeted neural- and non-neural tissue of a nervous system structure, the system comprising:
   an electrical stimulation device comprising one or more electrodes that delivers an electrical stimulation to a treatment site proximate the targeted neural- and non-neural tissue of the nervous system structure, at least one of the one or more electrodes comprising:
      an electrode in the form of an elongated body including two electrical contacts positioned thereon, the electrical contacts including a distal electrical contact adjacent a distal end of the elongated body and a proximal electrical contact located along the elongated body at a location between the distal electrical contact and a proximal end of the electrode, wherein the distal end of the elongated body includes a bend such that a distal tip portion of the elongated body extends at a predefined non-zero degree angle with respect to a longitudinal axis of the elongated body, wherein the distal electrical contact is provided on the distal tip portion of the elongated body and the proximal electrical contact is provided along the elongated body between the distal tip portion and the proximal end of the electrode;
   a controller configured to connect to the one or more electrodes of the electrical stimulation device and to a power source for supplying electrical energy to the one or more electrodes, where the controller is configured to direct operation of the electrical stimulation device and to apply the electrical stimulation to the treatment site through the one or more electrodes; and a temperature sensor coupled to the electrode for measuring a temperature of a contact surface of the electrode proximate the electrical contacts, the temperature sensor coupled to the controller and provides thermal feedback information regarding a measured temperature, wherein the application of the electrical stimulation to the treatment site selectively modulates the targeted neural- and non-neural tissue inhibiting pain and preserving other sensory and motor function, and proprioception, wherein at least one of the one or more electrodes includes two electrical contacts sized and configured to be positioned near the nervous system structure during treatment, wherein the controller is adjustable to modulate the electrical stimulation in response to the thermal feedback information to maintain a temperature of the contact surface of the stimulation device below a destructive tissue temperature.

2. The system claim 1, wherein the electrical stimulation device comprises a device body configured to be implanted within the patient at a location adjacent the treatment site.

3. The system of claim 1, wherein the controller comprises a stimulator, the stimulator being coupled to both the one or more electrodes at an interface of the controller, where operation of the stimulator is directed by the controller to provide the electrical stimulation to the one or more electrodes.

4. The system of claim 1, wherein the one or more electrodes comprise an electrode in the form of a paddle, cuff, cylindrical catheter or needle, wire form, or thin probe, wherein the one or more electrodes are sized and shaped to maximize and direct the electrical field toward the nervous system structure, wherein the electrode has an electrical contact surface area ranging from about 1 mm$^2$ to about 100 mm$^2$.

5. The system of claim 1, wherein the controller is configured to independently operate each of the two electrical contacts in a multipolar manner to direct current of the resultant electric field.

6. The system claim 1, wherein the length of each of the electrical contacts is different.

7. The system of claim 1, wherein at least one of the one or more electrodes is electrically coupled to the controller via a circumferentially-shaped electrical contact surface provided on the at least one of the one or more electrodes and a corresponding circumferentially-shaped contact surface provided on a lead electrically coupled to the controller, wherein the circumferentially-shaped contact surface includes more than one circumferentially-shaped contact surfaces arranged concentrically around the longitudinal axis of the electrode, wherein a lead electrically coupled between the electrode and the generator includes a corresponding more than one circumferentially-shaped contact surfaces arranged concentrically around a longitudinal axis of the lead.

8. The system of claim 7, wherein the circumferentially-shaped contact surfaces are separated by a dielectric layer, wherein the circumferentially-shaped contact surfaces of the lead are separated by a dielectric layer.

9. The system of claim 7, wherein electrical circuitry of at least one of the one or more electrodes extends within the circumferentially-shaped contact surfaces of the one or more electrodes.

10. The system of claim 1, wherein the controller is adjustable to vary at least one of the current and voltage of the electrical stimulation to maintain the temperature of the contact surface of the stimulation device below the destructive tissue temperature.

11. The system of claim 1, wherein the controller is adjustable to vary the duty cycle or waveform envelope duration of the electrical stimulation to maximize at least one of a voltage and a current delivered to the treatment site while not exceeding the destructive tissue temperature.

12. The system of claim 1, wherein the controller is adjustable to vary at least one parameter of the electrical stimulation to maintain a temperature of the contact surface of the stimulation device below a destructive tissue temperature, wherein the at least one parameter is selected from the group consisting of a waveform shape, a waveform frequency, a waveform amplitude, a waveform envelope duration an electrical field strength generated at the one or more electrodes, a waveform DC offset, a waveform duty cycle, a tissue temperature, a cooling mechanism parameter, and a treatment duration.

13. The system of claim 1, wherein the electrical stimulation delivered to the treatment site comprises a sinusoidal waveform.

14. An electrode for delivering electrical stimulation to a treatment site proximate for modulating targeted neural- and non-neural tissue of a nervous system structure, the electrode comprising:

an electrode in the form of an elongated body including two electrical contacts positioned thereon sized and configured to be positioned near the nervous system structure during treatment, the electrical contacts including a distal electrical contact adjacent a distal end of the elongated body and a proximal electrical contact located along the elongated body at a location between the distal electrical contact and a proximal end of the electrode, and a temperature sensor coupled to the electrode for measuring a temperature of a contact surface of the electrode proximate the electrical contacts, where the temperature sensor coupled to a controller and provides thermal feedback information regarding a measured temperature, wherein the distal end of the elongated body includes a bend such that a distal tip portion of the elongated body extends at a predefined non-zero degree angle with respect to a longitudinal axis of the elongated body, wherein the distal electrical contact is provided on the distal tip portion of the elongated body and the proximal electrical contact is provided along the elongated body between the distal tip portion and the proximal end of the electrode, wherein the application of the electrical stimulation to the treatment site selectively modulates the targeted neural- and non-neural tissue inhibiting pain and preserving other sensory and motor function, and proprioception, wherein the controller is adjustable to vary at least one parameter of the electrical stimulation in response to the thermal feedback information received from the temperature sensor to adjust a temperature of the contact surface and maintain the temperature of the contact surface of the stimulation device below the destructive tissue temperature.

15. The system of claim 14, wherein the angle of the distal tip portion with respect to the longitudinal axis of the elongated body is between 0 and about 50 degrees.

16. The system of claim 15, wherein the distal tip portion of the elongated body is curved,
wherein the angle of the distal tip portion with respect to the longitudinal axis of the elongated body is ranges from about 5 to about 15 degrees.

17. The system of claim 14,
wherein each of the electrical contacts are between about 1 and 50 mm in length,
wherein a length of the distal electrical contact is greater than a length of the proximal electrical contact.

18. The system of claim 14,
wherein at least a portion of each of the electrical contacts is located on a same side of the elongated body,
wherein the distal electrical contact is sized and configured to interface with targeted neural- and non-neural tissue of the nervous system structure,
wherein the proximal electrical contact is sized and configured to be positioned in subcutaneous tissue.

19. The system of claim 14, wherein conductive regions of each of the electrical contacts are on the same side of the elongated body and do not deliver electrical energy circumferentially to a portion of a circumference of the elongated body without electrical contacts.

20. The system of claim 14, further including a resistor positioned electrically in series with at least one of the electrical contacts.

21. The system of claim 14, wherein at least one of the electrical contacts extends only partially around a circumference of the electrode,
wherein an arc length of the at least one electrical contact around the circumference of the electrode is less than 180 degrees such that the at least one electrical contact extends around less than half of the circumference of the electrode.

22. The electrode of claim 14, wherein the temperature sensor further measures a temperature of the patient's tissue adjacent the contact surface,
wherein the controller is further adjustable to vary least one parameter of the electrical stimulation in response to the thermal feedback information received from the temperature sensor corresponding to the temperature of the patient's tissue to maintain the temperature of the patient's tissue below a destructive tissue temperature,
a cooling mechanism configured to provide a cooling effect at the treatment site and prevent damage at the treatment site by preserving temperatures of the patient's tissue below a destructive tissue temperature.

23. The electrode of claim 14, wherein the electrode is electrically coupled to a controller and to a power source for supplying electrical energy to the electrode, where the controller is configured to direct operation of the electrical stimulation device and to apply the electrical stimulation to the treatment site through the one or more electrodes.

24. The electrode of claim 23, wherein the controller is configured to independently operate each of the two electrical contacts in a multipolar manner to direct current of the resultant electric field.

* * * * *